US010857530B2

(12) United States Patent
Johns et al.

(10) Patent No.: US 10,857,530 B2
(45) Date of Patent: Dec. 8, 2020

(54) OLEFIN METATHESIS CATALYSTS

(71) Applicants: Umicore AG & Co. KG, Hanau-Wolfgang (DE); California Institute of Technology, Pasadena, CA (US)

(72) Inventors: Adam M. Johns, Claremont, CA (US); T. Patrick Montgomery, Pasadena, CA (US); Tonia S. Ahmed, Pasadena, CA (US); Robert H. Grubbs, South Pasadena, CA (US); Richard L. Pederson, San Gabriel, CA (US)

(73) Assignees: Umicore AG & Co. KG, Hanau-Wolfgang (DE); California Institute of Technology, Pasadena, CA (US)

(*) Notice: Subject to any disclaimer, the term of this patent is extended or adjusted under 35 U.S.C. 154(b) by 50 days.

(21) Appl. No.: 16/060,466

(22) PCT Filed: Dec. 9, 2016

(86) PCT No.: PCT/US2016/065844
§ 371 (c)(1),
(2) Date: Jun. 8, 2018

(87) PCT Pub. No.: WO2017/100585
PCT Pub. Date: Jun. 15, 2017

(65) Prior Publication Data
US 2018/0361371 A1 Dec. 20, 2018

Related U.S. Application Data

(60) Provisional application No. 62/377,337, filed on Aug. 19, 2016, provisional application No. 62/265,575, filed on Dec. 10, 2015.

(51) Int. Cl.
*B01J 31/22* (2006.01)
*C07C 6/06* (2006.01)
*C07C 6/04* (2006.01)

(52) U.S. Cl.
CPC ......... *B01J 31/2278* (2013.01); *B01J 31/226* (2013.01); *B01J 31/2273* (2013.01); *B01J 31/2295* (2013.01); *C07C 6/04* (2013.01); *C07C 6/06* (2013.01); *B01J 2231/54* (2013.01); *B01J 2531/821* (2013.01)

(58) Field of Classification Search
None
See application file for complete search history.

(56) References Cited

U.S. PATENT DOCUMENTS

| | | | |
|---|---|---|---|
| 8,394,965 B2 | 3/2013 | Mauduit et al. | |
| 8,716,488 B2 | 5/2014 | Jensen et al. | |
| 9,457,347 B2 | 10/2016 | Jensen et al. | |
| 2002/0022741 A1 | 2/2002 | Pederson et al. | |
| 2002/0198426 A1 | 12/2002 | Morgan et al. | |
| 2005/0261451 A1 | 11/2005 | Ung et al. | |
| 2008/0064891 A1 | 3/2008 | Lee | |
| 2014/0371454 A1 | 12/2014 | Hoveyda et al. | |

FOREIGN PATENT DOCUMENTS

| | | |
|---|---|---|
| WO | WO-2008065187 A1 | 6/2008 |
| WO | WO-2009094201 A2 | 7/2009 |
| WO | WO-2012097379 A2 | 7/2012 |
| WO | WO-2014093687 A1 | 6/2014 |
| WO | WO-2014186631 A1 | 11/2014 |
| WO | WO 2014/201300 * | 12/2014 |
| WO | WO-2014201300 A1 | 12/2014 |

OTHER PUBLICATIONS

Ahmed et al., "Fast-Initiating, Ruthenium-based Catalysts for Improved Activity in Highly E-Selective Cross Metathesis", Journal of the American Chemical Society, XXXX, XXX, XXX-XXX (Oct. 31, 2016).
Binder et al., "Olefin Metathesis for Chemical Biology", Curr. Opin. Chem. Biol., vol. 12, No. 6, pp. 767-773 (2008).
Endo et al., "Chelated Ruthenium Catalysts for Z-Selective Olefin Metathesis", J. Am. Chem. Soc., vol. 133, pp. 8525-8527 (2011).
Flook et al., "Z-Selective Olefin Metathesis Processes Catalyzed by a Molybdenum Hexaisopropylterphenoxide Monopyrrolide Complex", J. Am. Chem. Soc., vol. 131, pp. 7962-7963 (2009).
Fürstner, "Olefin Metathesis and Beyond", Agnew. Chem. Int. Ed., vol. 39, pp. 3012-3043 (2000).
Grubbs, "Handbook of Metathesis", 442 pages (2003).
Jiang et al., "Highly Z-Selective Metathesis Homocoupling of Terminal Olefins", J. Am. Chem. Soc., vol. 131, pp. 16630-16631 (2009).
Johns et al., "High Trans Kinetic Selectivity in Ruthenium-Based Olefin Cross-Metathesis through Stereoretention", Org. Lett., vol. 18, pp. 772-775 (2016).
Keitz et al., "Improved Ruthenium Catalysts for Z-Selective Olefin Metathesis", J. Am. Chem. Soc., vol. 134, pp. 693-699 (2012).
Keitz et al., "Z-Selective Homodimerization of Terminal Olefins with a Ruthenium Metathesis Catalyst", J. Am. Chem. Soc., vol. 133, pp. 9686-9688 (2011).
Khan et al., "Readily Accessible and Easily Modifiable Ru-Based Catalysts for Efficient and Z-Selective Ring-Opening Metathesis Polymerization and Ring-Opening/Cross-Metathesis", J. Am. Chem. Soc., vol. 135, pp. 10258-10261 (2013).
Koh et al., "High-Value Alcohols and Higher-Oxidation-State Compounds by Catalytic Z-Selective Cross-Metathesis", Nature, vol. 517, pp. 181-234 (2015).
Leitgeb et al., "The ROMP Toolbox Upgraded", Polymer, vol. 51, pp. 2927-2946 (2010).

(Continued)

Primary Examiner — Yun Qian
(74) Attorney, Agent, or Firm — Faegre Drinker Biddle & Reath LLP

(57) ABSTRACT

This invention relates generally to metathesis catalysts and the use of such catalysts in the metathesis of olefins and olefin compounds, more particularly, in the use of such catalysts in Z and E selective olefin metathesis reactions. The invention has utility in the fields of organometallics and organic synthesis.

17 Claims, No Drawings

(56) References Cited

OTHER PUBLICATIONS

Liu et al., "Olefin Metathesis on Nanostructures", Journal of Organometallic Chemistry, vol. 691, pp. 5148-5154 (2006).
Meek et al., "Catalytic Z-Selective Olefin Cross-Metathesis for Natural Production Synthesis", Nature, vol. 471, pp. 461-466 (2011).
Mikus et al., "Controllable ROMP Tacticity by Harnessing the Fluxionality of Steriogenic-at-Ruthenium Complexes", Angew. Chem. Int. Ed., vol. 55, pp. 4997-5002 (2016).
Samojiowicz et al., "Ruthenium-Based Olefin Metathesis Catalysts Bearing N-Heterocycle Carbene Ligands", Chem. Rev., vol. 109, pp. 3708-3742 (2009).
Schrock et al., "Molybdenum and Tungsten Imido Alkylidene Complexes as Efficient Olefin-Metathesis Catalysts", Angew. Chem. Int. Ed., vol. 42, pp. 4592-4633 (2003).
Schrock, "High Oxidation State Multiple Metal-Carbon Bonds", Chem. Rev., vol. 102, pp. 145-179 (2002).
Sutthasupa et al., "Recent Advances in Ring-Opening Metathesis Polymerization, and Application to Synthesis of Functional Materials", Polymer Journal, pp. 1-11 (2010).
Trnka et al., "The Development of $L_2X_2Ru=CHR$ Olefin Metathesis Catalysts: An Organometallic Success Story", Acc. Chem. Res., vol. 34, pp. 18-29 (2001).
Vougioukalakis et al., "Ruthenium-Based Heterocycle Carbene—Carbene-Coordinated Olefin Metathesis Catalysts", Chem. Rev., vol. 110, pp. 1746-1787 (2010).
International Search Report for PCT/US2016/065844 dated Mar. 2, 2017.
Written Opinion of the International Searching Authority for PCT/US2016/065844 dated Mar. 2, 2017.
Third Party Submission in the prosectuion of the EP equivalent EP 3386936, dated May 13, 2020.

\* cited by examiner

OLEFIN METATHESIS CATALYSTS

CROSS-REFERENCE TO RELATED APPLICATIONS

This application is a national stage application (under 35 U.S.C. § 371) of PCT/US2016/065844, filed Dec. 9, 2016, which claims benefit of U.S. Application Nos. 62/265,575, filed Dec. 10, 2015, and 62/377,337, filed Aug. 19, 2016, all of which are incorporated herein by reference in their entirety.

TECHNICAL FIELD

This invention relates generally to metathesis catalysts and the use of such catalysts in the metathesis of olefins and olefin compounds, more particularly, in the use of such catalysts in Z or E selective olefin metathesis reactions, particularly Z or E selective cross metathesis reactions. The invention has utility in the fields of organometallics and organic synthesis.

BACKGROUND

The transition-metal catalyzed olefin metathesis reaction is an important methodology for the construction of new carbon-carbon double bonds (see (a) Fürstner, A. *Angew. Chem., Int. Ed.* 2000, 39, 3013. (b) Trnka, T. M.; Grubbs, R. H. *Acc. Chem. Res.* 2001, 34, 18. (c) Schrock, R. R. *Chem. Rev.* 2002, 102, 145. (d) Schrock, R. R.; Hoveyda, A. H. *Angew. Chem., Int. Ed.* 2003, 42, 4592. (e) Vougioukalakis, G.; Grubbs, R. H. *Chem. Rev.* 2009, 110, 1746. (f) Samojlowicz, C.; Bieniek, M.; Grela, K. *Chem. Rev.* 2009, 109, 3708).

Since its discovery metathesis has been employed with success in a number of fields, including biochemistry, materials science, and green chemistry (see (a) Binder, J. B.; Raines, R. T. *Curr. Opin. Chem. Biol.* 2008, 12, 767; (b) Leitgeb, A.; Wappel, J.; Slugovc, C. *Polymer* 2010, 51, 2927; (c) Sutthasupa, S.; Shiotsuki, M.; Sanda, F. *Polym. J.* 2010, 42, 905; (d) Liu, X.; Basu, A. *J. Organomet. Chem.* 2006, 691, 5148).

However, an ongoing challenge in cross metathesis (CM) reactions has been the control of stereoselectivity, particularly the retention of the stereoselectivity of the Z or E olefin, as metathesis catalysts generally favor formation of the thermodynamically preferred E-olefin (see Grubbs, R. H. *Handbook of Metathesis*; Wiley-VCH: Weinheim, 2003).

Work by Schrock and Hoveyda et. al. resulted in the development of Z-selective metathesis catalysts using molybdenum and tungsten, allowing for the synthesis of Z-olefins via metathesis (see (a) Flook, M. M.; Jiang, A. J.; Schrock, R. R.; Müller, P.; Hoveyda, A. H. *J. Am. Chem. Soc.* 2009, 131, 7962. (b) Marinescu, S. C.; Schrock, R. R.; Müller, P.; Takase, M. K.; Hoveyda, A. H. *Organometallics* 2011, 30, 1780. (c) Meek, S. J.; O'Brien, R. V.; Llaveria, J.; Schrock, R. R.; Hoveyda, A. H. *Nature* 2011, 471, 461. (d) Jiang, A. J.; Zhao, Y.; Schrock, R. R.; Hoveyda, A. H. *J. Am. Chem. Soc.* 2009, 131, 16630. (e) WO 2009/094201 A2).

Work by Grubbs et al. resulted in the development of Z-selective ruthenium metathesis catalysts containing a chelating N-heterocyclic carbene (NHC) ligand, allowing for the synthesis of Z-olefins via metathesis (see (a) Endo, K.; Grubbs, R. H. *J. Am. Chem. Soc.* 2011, 133, 8525. (b) Keitz, B. K.; Endo, K.; Herbert, M. B.; Grubbs, R. H. *J. Am. Chem. Soc.* 2011, 133, 9686. (c) Keitz, B. K.; Endo, K.; Patel, P. R.; Herbert, M. B.; Grubbs, R. H. *J. Am. Chem. Soc.* 2011, 134, 693. (d) WO 2012/097379 A2. (e) WO 2014/093687 A1).

Work by Hoveyda et al. resulted in the development of Z-selective ruthenium metathesis catalysts containing a NHC ligand and a bidentate anionic ligand, allowing for the synthesis of Z-olefins via metathesis (see (a) Khan, R. K. M.; Torker, S.; Hoveyda, A. H. *J. Am. Chem. Soc.* 2013, 135, 10258. (b) WO 2014/201300 A1. (c) Koh, M. J.; Khan, K. M.; Torker, S.; Yu, M.; Mikus, M. S.; Hoveyda, A. M. *Nature* 2015, 517, 181).

Despite the advances achieved, a continuing need exists for improved catalysts, particularly stereoselective and stereoretentive olefin metathesis catalysts which provide improved activity and Z or E selectivity in olefin metathesis reactions, particularly in cross metathesis reactions. The invention is directed to addressing one or more of the aforementioned concerns.

SUMMARY

In the course of evaluating Z-selective olefin metathesis catalysts for selective reactions with mixtures of cis and trans 5-tetradecene (5C14) (14:86 Z:E), C765 was found to afford a thermodynamic distribution of products after 5 hours (Scheme 1). Prompted by this unusual apparent lack of selectivity, a more thorough investigation into this family of catalysts was initiated.

Scheme 1
Self-metathesis of 5-Tetradecene

5C14 (14:86 Z:E) →[1000 ppm C765 / THF [0.5M], 40° C., 5 h] 5C10 + 9C18

| %5C14 (Z/E) | %5C10 (Z/E) | %9C18 |
|---|---|---|
| 52 (14/86) | 24 (14/86) | 24 |

In one embodiment, the invention provides a compound of Formula (I):

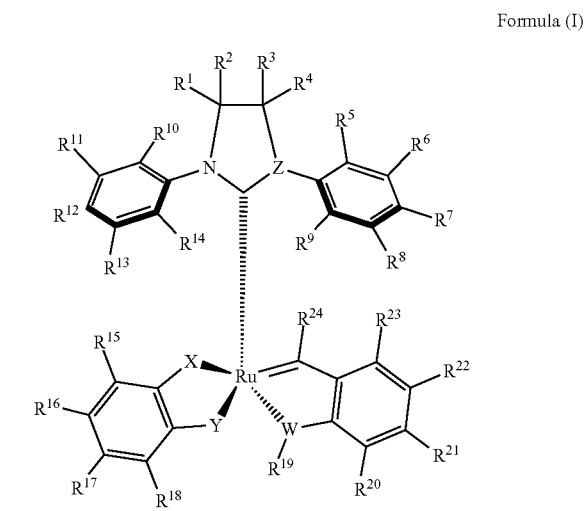

Formula (I)

wherein:
X is O or S;
Y is O or S;
Z is N or CR$^{32}$;
W is O, NR$^{33}$ or S;

$R^1$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^2$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl, optionally substituted $C_{3-8}$ cycloalkenyl or together with $R^3$ may form a polycyclic ring;

$R^3$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl or together with $R^2$ may form a polycyclic ring;

$R^4$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^5$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^6$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^7$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^8$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^9$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{10}$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{11}$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{12}$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{13}$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{14}$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{15}$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl, or together with $R^{16}$ may form an optionally substituted polycyclic ring;

$R^{16}$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl, or together with $R^{15}$ may form an optionally substituted polycyclic ring;

$R^{17}$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl, or together with $R^{18}$ may form an optionally substituted polycyclic ring;

$R^{18}$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl, or together with $R^{17}$ may form an optionally substituted polycyclic ring;

$R^{19}$ is hydrogen, optionally substituted $C_{1-24}$ alkyl, —C(O)$R^{25}$, optionally substituted heterocycle, optionally substituted $C_{3-8}$ cycloalkyl, optionally substituted $C_{5-24}$ aryl or optionally substituted $C_{3-8}$ cycloalkenyl;

$R^{20}$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{21}$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{22}$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{23}$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{24}$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{25}$ is OH, O$R^{30}$, N$R^{27}R^{28}$, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl, $R^{26}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{27}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{28}$ is H, optionally substituted $C_{1-8}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{29}$ is hydrogen, optionally substituted $C_{1-24}$ alkyl, O$R^{26}$, —N$R^{27}R^{28}$, optionally substituted heterocycle, optionally substituted $C_{3-8}$ cycloalkyl, optionally substituted $C_{5-24}$ aryl or optionally substituted $C_{3-8}$ cycloalkenyl;

$R^{30}$ is optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{31}$ is hydrogen, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{32}$ is hydrogen, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{33}$ is hydrogen, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl; and m is 1 or 2.

In one embodiment, the invention provides a method for performing a cross metathesis reaction, comprising: contacting a first internal olefin reactant with a second internal olefin reactant in the presence of a compound of Formula (I), under conditions effective to promote the formation of at least one cross metathesis product, where the first internal olefin reactant and the second internal olefin reactant may be the same or different, where the first internal olefin reactant and the second internal olefin reactant are each in a Z-configuration; and where the at least one cross metathesis product is greater than about 80% Z.

In one embodiment, the invention provides a method for performing a cross metathesis reaction, comprising: contacting a first internal olefin reactant with a second internal olefin reactant in the presence of a compound of Formula (I), under conditions effective to promote the formation of at least one cross metathesis product, where the first internal olefin reactant and the second internal olefin reactant may be the same or different, where the first internal olefin reactant and the second internal olefin reactant are each in a Z-configuration; and where the at least one cross metathesis product is greater than about 90% Z.

In one embodiment, the invention provides a method for performing a cross metathesis reaction, comprising: contacting a first internal olefin reactant with a second internal olefin reactant in the presence of a compound of Formula (I), under conditions effective to promote the formation of at least one cross metathesis product, where the first internal olefin reactant and the second internal olefin reactant may be the same or different, where the first internal olefin reactant and the second internal olefin reactant are each in a Z-configuration; and where the at least one cross metathesis product is greater than about 95% Z.

In one embodiment, the invention provides a method for performing a cross metathesis reaction, comprising: contacting a first internal olefin reactant with a second internal olefin reactant in the presence of a compound of Formula (I), under conditions effective to promote the formation of at least one cross metathesis product, where the first internal olefin reactant and the second internal olefin reactant may be the same or different, where the first internal olefin reactant and the second internal olefin reactant are each in a Z-configuration; and where the at least one cross metathesis product is greater than about 99% Z.

In one embodiment, the invention provides a method for performing a cross metathesis reaction, comprising: contacting a first internal olefin reactant with a second internal olefin reactant in the presence of a compound of Formula (I), under conditions effective to promote the formation of at least one cross metathesis product, where the first internal olefin reactant and the second internal olefin reactant may be the same or different, where the first internal olefin reactant and the second internal olefin reactant are each in an E-configuration; and where the at least one cross metathesis product is greater than about 80% E.

In one embodiment, the invention provides a method for performing a cross metathesis reaction, comprising: contacting a first internal olefin reactant with a second internal olefin reactant in the presence of a compound of Formula (I), under conditions effective to promote the formation of at least one cross metathesis product, where the first internal olefin reactant and the second internal olefin reactant may be the same or different, where the first internal olefin reactant and the second internal olefin reactant are each in an E-configuration; and where the at least one cross metathesis product is greater than about 90% E.

In one embodiment, the invention provides a method for performing a cross metathesis reaction, comprising: contacting a first internal olefin reactant with a second internal olefin reactant in the presence of a compound of Formula (I), under conditions effective to promote the formation of at least one cross metathesis product, where the first internal olefin reactant and the second internal olefin reactant may be the same or different, where the first internal olefin reactant and the second internal olefin reactant are each in an E-configuration; and where the at least one cross metathesis product is greater than about 95% E.

In one embodiment, the invention provides a method for performing a cross metathesis reaction, comprising: contacting a first internal olefin reactant with a second internal olefin reactant in the presence of a compound of Formula (I), under conditions effective to promote the formation of at least one cross metathesis product, where the first internal olefin reactant and the second internal olefin reactant may be the same or different, where the first internal olefin reactant and the second internal olefin reactant are each in an E-configuration; and where the at least one cross metathesis product is greater than about 99% E.

In one embodiment, the invention provides a method for performing a cross metathesis reaction, comprising: contacting a first internal olefin reactant with a second terminal olefin reactant in the presence of a compound of Formula (I), under conditions effective to promote the formation of at least one cross metathesis product, where the first internal olefin reactant is in a Z-configuration; and where the at least one cross metathesis product is greater than about 80% Z.

In one embodiment, the invention provides a method for performing a cross metathesis reaction, comprising: contacting a first internal olefin reactant with a second terminal olefin reactant in the presence of a compound of Formula (I), under conditions effective to promote the formation of at least one cross metathesis product, where the first internal olefin reactant is in a Z-configuration; and where the at least one cross metathesis product is greater than about 90% Z.

In one embodiment, the invention provides a method for performing a cross metathesis reaction, comprising: contacting a first internal olefin reactant with a second terminal olefin reactant in the presence of a compound of Formula (I), under conditions effective to promote the formation of at least one cross metathesis product, where the first internal olefin reactant is in a Z-configuration; and where the at least one cross metathesis product is greater than about 95% Z.

In one embodiment, the invention provides a method for performing a cross metathesis reaction, comprising: contacting a first internal olefin reactant with a second terminal olefin reactant in the presence of a compound of Formula (I), under conditions effective to promote the formation of at least one cross metathesis product, where the first internal olefin reactant is in a Z-configuration; and where the at least one cross metathesis product is greater than about 99% Z.

In one embodiment, the invention provides a method for performing a cross metathesis reaction, comprising: contacting a first internal olefin reactant with a second terminal olefin reactant in the presence of a compound of Formula (I), under conditions effective to promote the formation of at least one cross metathesis product, where the first internal olefin reactant is in an E-configuration; and where the at least one cross metathesis product is greater than about 80% E.

In one embodiment, the invention provides a method for performing a cross metathesis reaction, comprising: contacting a first internal olefin reactant with a second terminal olefin reactant in the presence of a compound of Formula (I), under conditions effective to promote the formation of at least one cross metathesis product, where the first internal olefin reactant is in an E-configuration; and where the at least one cross metathesis product is greater than about 90% E.

In one embodiment, the invention provides a method for performing a cross metathesis reaction, comprising: contacting a first internal olefin reactant with a second terminal olefin reactant in the presence of a compound of Formula (I), under conditions effective to promote the formation of at least one cross metathesis product, where the first internal olefin reactant is in an E-configuration; and where the at least one cross metathesis product is greater than about 95% E.

In one embodiment, the invention provides a method for performing a cross metathesis reaction, comprising: contacting a first internal olefin reactant with a second terminal olefin reactant in the presence of a compound of Formula (I), under conditions effective to promote the formation of at least one cross metathesis product, where the first internal olefin reactant is in an E-configuration; and where the at least one cross metathesis product is greater than about 99% E.

In one embodiment, the invention provides for use of a compound of Formula (I) in olefin metathesis. In one embodiment, the invention provides for use of a compound of Formula (I) in an olefin metathesis reaction. In one embodiment, the invention provides for use of a compound of Formula (I) in a Z-selective olefin metathesis reaction. In one embodiment, the invention provides for use of a compound of Formula (I) in a Z-selective cross metathesis reaction.

In one embodiment, the invention provides for use of a compound of Formula (I) in olefin metathesis. In one embodiment, the invention provides for use of a compound of Formula (I) in an olefin metathesis reaction. In one embodiment, the invention provides for use of a compound of Formula (I) in an E-selective olefin metathesis reaction. In one embodiment, the invention provides for use of a compound of Formula (I) in an E-selective cross metathesis reaction.

In one embodiment, the invention provides a method for performing a Z-selective olefin metathesis reaction. In one embodiment, the invention provides a method for performing a Z-selective cross metathesis reaction.

In one embodiment, the invention provides a method for performing an E-selective olefin metathesis reaction. In one embodiment, the invention provides a method for performing an E-selective cross metathesis reaction.

These and other aspects of the invention will be apparent to the skilled artisan in light of the following detailed description and examples.

DETAILED DESCRIPTION

Terminology and Definitions

Unless otherwise indicated, the invention is not limited to specific reactants, reaction conditions, or the like, as such may vary. It is also to be understood that the terminology used herein is for the purpose of describing particular embodiments and is not to be interpreted as being limiting.

As used in the specification and the appended claims, the singular forms "a," "an," and "the" include plural referents unless the context clearly dictates otherwise. Thus, for example, reference to "an α-olefin" includes a single α-olefin as well as a combination or mixture of two or more α-olefins, reference to "a substituent" encompasses a single substituent as well as two or more substituents, and the like.

As used in the specification and the appended claims, the terms "for example," "for instance," "such as," or "including" are meant to introduce examples that further clarify more general subject matter. Unless otherwise specified, these examples are provided only as an aid for understanding the invention, and are not meant to be limiting in any fashion.

In this specification and in the claims that follow, reference will be made to a number of terms, which shall be defined to have the following meanings.

The term "alkyl" as used herein refers to a linear, branched, or cyclic saturated hydrocarbon group typically although not necessarily containing 1 to about 24 carbon atoms, preferably 1 to about 12 carbon atoms, such as methyl (Me), ethyl (Et), n-propyl (Pr or n-Pr), isopropyl (i-Pr), n-butyl (Bu or n-Bu), isobutyl (i-Bu), t-butyl (t-Bu), octyl (Oct), decyl, and the like, as well as cycloalkyl groups such as cyclopentyl (Cp), cyclohexyl (Cy) and the like. Generally, although again not necessarily, alkyl groups herein contain 1 to about 8 carbon atoms. The term "lower alkyl" refers to an alkyl group of 1 to 6 carbon atoms, and the specific term "cycloalkyl" refers to a cyclic alkyl group, typically having 3 to 8, preferably 5 to 7, carbon atoms. The term "substituted alkyl" refers to alkyl substituted with one or more substituent groups, and the terms "heteroatom-containing alkyl" and "heteroalkyl" refer to alkyl in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl, respectively.

The term "alkylene" as used herein refers to a difunctional linear, branched, or cyclic alkyl group, where "alkyl" is as defined above.

The term "alkenyl" as used herein refers to a linear, branched, or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Preferred alkenyl groups herein contain 2 to about 12 carbon atoms. The term "lower alkenyl" refers to an alkenyl group of 2 to 6 carbon atoms, and the specific term "cycloalkenyl" refers to a cyclic alkenyl group, preferably having 3 to 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkenylene" as used herein refers to a difunctional linear, branched, or cyclic alkenyl group, where "alkenyl" is as defined above.

The term "alkynyl" as used herein refers to a linear or branched hydrocarbon group of 2 to about 24 carbon atoms containing at least one triple bond, such as ethynyl, n-propynyl, and the like. Preferred alkynyl groups herein contain 2 to about 12 carbon atoms. The term "lower alkynyl" refers to an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkynylene" as used herein refers to a difunctional alkynyl group, where "alkynyl" is as defined above.

The term "alkoxy" as used herein refers to an alkyl group bound through a single, terminal ether linkage; that is, an "alkoxy" group may be represented as —O-alkyl where alkyl is as defined above. A "lower alkoxy" group refers to an alkoxy group containing 1 to 6 carbon atoms. Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain 5 to 24 carbon atoms, and particularly preferred aryl groups contain 6 to 10 carbon atoms. Exemplary aryl groups contain one aromatic ring or two fused or linked aromatic rings, e.g., phenyl (Ph), naphthyl, biphenyl, diphenylether, diphenylamine, benzophenone, phenanthryl and the like. "Substituted aryl" refers to an aryl moiety substituted with one or more substituent groups, and the terms "heteroatom containing aryl" and "heteroaryl" refer to aryl substituents in which at least one carbon atom is replaced with a heteroatom, as will be described in further detail herein.

The term "aryloxy" as used herein refers to an aryl group bound through a single, terminal ether linkage, wherein "aryl" is as defined above. An "aryloxy" group may be represented as —O-aryl where aryl is as defined above. Preferred aryloxy groups contain 5 to 24 carbon atoms, and particularly preferred aryloxy groups contain 6 to 10 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Preferred alkaryl and aralkyl groups contain 6 to 24 carbon atoms, and particularly preferred alkaryl and aralkyl groups contain 6 to 16 carbon atoms. Alkaryl groups include, without limitation, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. The terms "alkaryloxy" and "aralkyloxy" refer to substituents of the formula —OR wherein R is alkaryl or aralkyl, respectively, as just defined.

The term "acyl" refers to substituents having the formula —(CO)-alkyl, —(CO)-aryl, —(CO)-aralkyl, —(CO)-alkaryl, —(CO)-alkenyl, or —(CO)-alkynyl, and the term "acyloxy" refers to substituents having the formula —O(CO)-alkyl, —O(CO)-aryl, —O(CO)-aralkyl, —O(CO)-alkaryl, —O(CO)-alkenyl, or —(CO)-alkynyl wherein "alkyl," "aryl", "aralkyl", "alkaryl", "alkenyl", and "alkynyl" are as defined above. The acetoxy group (—O (CO)CH$_3$; often abbreviated as —OAc) is a common example of an acyloxy group.

The terms "cyclic" and "ring" refer to alicyclic or aromatic groups that may or may not be substituted and/or heteroatom containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic or polycyclic.

The terms "polycyclic ring" refer to alicyclic or aromatic groups that may or may not be substituted and/or heteroatom containing, and that have at least two closed rings tethered, fused, linked via a single bond or bridged. Polycyclic rings include without limitation naphthyl, biphenyl, phenanthryl and the like.

The terms "halo" and "halogen" and "halide" are used in the conventional sense to refer to a fluoro, chloro, bromo, or iodo substituent.

"Hydrocarbyl" refers to univalent hydrocarbyl radicals containing 1 to about 30 carbon atoms, preferably 1 to about 24 carbon atoms, most preferably 1 to about 12 carbon atoms, including linear, branched, cyclic, saturated and unsaturated species, such as alkyl groups, alkenyl groups, alkynyl groups, aryl groups, and the like. The term "lower hydrocarbyl" refers to a hydrocarbyl group of 1 to 6 carbon atoms, preferably 1 to 4 carbon atoms, and the term "hydrocarbylene" refers to a divalent hydrocarbyl moiety containing 1 to about 30 carbon atoms, preferably 1 to about 24 carbon atoms, most preferably 1 to about 12 carbon atoms, including linear, branched, cyclic, saturated and unsaturated species. The term "lower hydrocarbylene" refers to a hydrocarbylene group of 1 to 6 carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatom-containing hydrocarbylene" and heterohydrocarbylene" refer to hydrocarbylene in which at least one carbon atom is replaced with a heteroatom. Unless otherwise indicated, the term "hydrocarbyl" and "hydrocarbylene" are to be interpreted as including substituted and/or heteroatom-containing hydrocarbyl and hydrocarbylene moieties, respectively.

The term "heteroatom-containing" as in a "heteroatom-containing hydrocarbyl group" refers to a hydrocarbon molecule or a hydrocarbyl molecular fragment in which one or more carbon atoms is replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and "heteroaromatic" respectively refer to "aryl" and "aromatic" substituents that are heteroatom-containing, and the like. It should be noted that a "heterocyclic" group or compound may or may not be aromatic, and further that "heterocycles" may be monocyclic, bicyclic, or polycyclic as described above with respect to the term "aryl." Examples of heteroalkyl groups include without limitation alkoxyaryl, alkylsulfanyl-substituted alkyl, N-alkylated amino alkyl, and the like. Examples of heteroaryl substituents include without limitation pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups include without limitation pyrrolidino, morpholino, piperazino, piperidino, etc.

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with one or more non-hydrogen substituents. Examples of such substituents include, without limitation: functional groups referred to herein as "Fn," such as halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{24}$ aryloxy, $C_6$-$C_{24}$ aralkyloxy, $C_6$-$C_{24}$ alkaryloxy, acyl (including $C_2$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl (—(CO)—O-alkyl), $C_6$-$C_{24}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO"), carbamoyl (—(CO)—$NH_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_1$-$C_{24}$ haloalkyl)-substituted carbamoyl (—(CO)—NH($C_1$-$C_{24}$ haloalkyl)), di-($C_1$-$C_{24}$ haloalkyl)-substituted carbamoyl (—(CO)—N($C_1$-$C_{24}$ haloalkyl)$_2$), mono-($C_5$-$C_{24}$ aryl)-substituted carbamoyl (—(CO)—NH-aryl), di-($C_5$-$C_{24}$ aryl)-substituted carbamoyl (—(CO)—N($C_5$-$C_{24}$ aryl)$_2$), di-N—($C_1$-$C_{24}$ alkyl), N—($C_5$-$C_{24}$ aryl)-substituted carbamoyl (—(CO)—N($C_1$-$C_{24}$ alkyl)($C_5$-$C_{24}$ aryl), thiocarbamoyl (—(CS)—$NH_2$), mono-($C_1$-$C_{24}$ alkyl)-substituted thiocarbamoyl (—(CS)—NH($C_1$-$C_{24}$ alkyl)), di-($C_1$-$C_{24}$ alkyl)-substituted thiocarbamoyl (—(CS)—N($C_1$-$C_{24}$ alkyl)$_2$), mono-($C_5$-$C_{24}$ aryl)-substituted thiocarbamoyl (—(CS)—NH-aryl), di-($C_5$-$C_{24}$ aryl)-substituted thiocarbamoyl (—(CS)—N($C_5$-$C_{24}$ aryl)$_2$), di-N—($C_1$-$C_{24}$ alkyl), N—($C_5$-$C_{24}$ aryl)-substituted thiocarbamoyl (—(CS)—N($C_1$-$C_{24}$ alkyl)($C_5$-$C_{24}$ aryl), carbamido (—NH—(CO)—$NH_2$), cyano(—C≡N), cyanato (—O—C≡N), thiocyanato (—S—C≡N), isocyanate (—NisCisO), thioisocyanate (—NisCisS), formyl (—(CO)—H), thioformyl (—(CS)—H), amino (—$NH_2$), mono-($C_1$-$C_{24}$ alkyl)-substituted amino (—NH($C_1$-$C_{24}$ alkyl), di-($C_1$-$C_{24}$ alkyl)-substituted amino ((—N($C_1$-$C_{24}$ alkyl)$_2$), mono-($C_5$-$C_{24}$ aryl)-substituted amino (—NH($C_5$-$C_{24}$ aryl), di-($C_5$-$C_{24}$ aryl)-substituted amino (—N($C_5$-$C_{24}$ aryl)$_2$), $C_2$-$C_{24}$ alkylamido (—NH—(CO)-alkyl), $C_6$-$C_{24}$ arylamido (—NH—(CO)-aryl), imino (—CRisNH where, R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), $C_2$-$C_{20}$ alkylimino (—CRisN(alkyl), where R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CRisN(aryl), where R includes without limitation hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—$NO_2$), nitroso (—NO), sulfo (—$SO_2$—OH), sulfonato (—$SO_2$—O—), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—$SO_2$-alkyl), $C_1$-$C_{24}$ monoalkylaminosulfonyl (—$SO_2$—N(H) alkyl), $C_1$-$C_{24}$ dialkylaminosulfonyl (—$SO_2$—N(alkyl)$_2$), $C_5$-$C_{24}$ arylsulfonyl (—$SO_2$-aryl), boryl (—$BH_2$), borono (—B(OH)$_2$), boronato (—B(OR)$_2$ where R includes without limitation alkyl or other hydrocarbyl), phosphono (—P(O)(OH)$_2$), phosphonato (—P(O)(O")$_2$), phosphinato (—P(O)(O)), phospho (—$PO_2$), phosphino (—$PH_2$), silyl (—$SiR_3$ wherein R is hydrogen or hydrocarbyl), and silyloxy (—O-silyl); and the hydrocarbyl moieties $C_1$-$C_{24}$ alkyl (preferably $C_1$-$C_{12}$ alkyl, more preferably $C_1$-$C_6$ alkyl), $C_2$-$C_{24}$ alkenyl (preferably $C_2$-$C_{12}$ alkenyl, more preferably $C_2$-$C_6$ alkenyl), $C_2$-$C_{24}$ alkynyl (preferably $C_2$-$C_{12}$ alkynyl, more preferably $C_2$-$C_6$ alkynyl), $C_5$-$C_{24}$ aryl (preferably $C_5$-$C_{14}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl).

By "functionalized" as in "functionalized hydrocarbyl," "functionalized alkyl," "functionalized olefin," "functionalized cyclic olefin," and the like, is meant that in the hydrocarbyl, alkyl, olefin, cyclic olefin, or other moiety, at least one hydrogen atom bound to a carbon (or other) atom is replaced with one or more functional groups such as those described hereinabove. The term "functional group" is meant to include any functional species that is suitable for the uses described herein. In particular, as used herein, a functional group would necessarily possess the ability to react with or bond to corresponding functional groups on a substrate surface.

In addition, the aforementioned functional groups may, if a particular group permits, be further substituted with one or more additional functional groups or with one or more hydrocarbyl moieties such as those specifically enumerated above. Analogously, the above mentioned hydrocarbyl moieties may be further substituted with one or more functional groups or additional hydrocarbyl moieties such as those specifically mentioned above. Analogously, the above-mentioned hydrocarbyl moieties may be further substituted with one or more functional groups or additional hydrocarbyl moieties as noted above.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The term "internal olefin" as used herein means an olefin wherein each of the olefinic carbons (i.e., the carbons of the carbon-carbon double bond) is substituted by at least one non-hydrogen substituent. The internal olefin may be di-substituted, tri-substituted, or tetra-substituted (e.g., $R^{1'}HC$ is $CHR^{2'}$; $R^{3'}R^{4'}C$ is $CHR^{5'}$; $R^{6'}R^{7'}C$ is $CR^{8'}R^{9'}$; where $R^{1'}$, $R^{2'}$, $R^{3'}$, $R^{4'}$, $R^{5'}$, $R^{6'}$, $R^{7'}$, $R^{8'}$, and $R^{9'}$ may be the same or different and are each independently optionally substituted hydrocarbyl, optionally substituted heteroatom-containing hydrocarbyl, or a functional group).

The term "terminal olefin" as used herein means an olefin wherein one of the olefinic carbons (i.e., the carbons of the carbon-carbon double bond) is substituted by at least one non-hydrogen substituent and the other olefinic carbon is unsubstituted. The terminal olefin may be di-substituted or mono-substituted (e.g., $CH_2$ is $CHR^{10'}$ or $CH_2$ is $CR^{11'}R^{12'}$; where $R^{10'}$, $R^{11'}$, and $R^{12'}$ may be the same or different and are each independently optionally substituted hydrocarbyl, optionally substituted heteroatom-containing hydrocarbyl, or a functional group).

The term "reactant internal olefin" as used herein means an internal olefin present in an olefin compound used in a cross metathesis reaction with another olefin compound to form a cross metathesis product. The "reactant internal olefin" may be di-substituted, tri-substituted, or tetra-substituted. The "reactant internal olefin" may have an E-configuration or a Z-configuration.

The term "product internal olefin" as used herein means an internal olefin present in a cross metathesis product formed by a cross metathesis reaction, wherein each of the olefinic carbons (i.e., the carbons of the carbon-carbon double bond) of the internal olefin is substituted by at least one non-hydrogen substituent. The "product internal olefin" may be di-substituted, tri-substituted, or tetra-substituted. The "product internal olefin" may have an E configuration or a Z-configuration.

The term "nil", as used herein, means absent or nonexistent.

The term "hydroxyl" as used herein, represents a group of formula "—OH".

The term "carbonyl" as used herein, represents a group of formula "—C(O)—".

The term "ketone" as used herein, represents an organic compound having a carbonyl group linked to a carbon atom such as —$C(O)R^x$ wherein $R^x$ can be alkyl, aryl, cycloalkyl, cycloalkenyl, heterocycle as defined above.

The term "ester" as used herein, represents an organic compound having a carbonyl group linked to a carbon atom such as —$C(O)OR^x$ wherein $R^x$ can be alkyl, aryl, cycloalkyl, cycloalkenyl, heterocycle as defined above.

The term "amine" as used herein, represents a group of formula "—$NR^xR^y$," wherein $R^x$ and $R^y$ can be the same or independently H, alkyl, aryl, cycloalkyl, cycloalkenyl, heterocycle as defined above.

The term "carboxyl" as used herein, represents a group of formula "—C(O)O—".

The term "sulfonyl" as used herein, represents a group of formula "—$SO_2$".

The term "sulfate" as used herein, represents a group of formula "—O—$S(O)_2$—O—".

The term "sulfonate" as used herein, represents a group of the formula "—$S(O)_2$—O—".

The term "carboxylic acid" as used herein, represents a group of formula "—C(O)OH".

The term "nitro" as used herein, represents a group of formula "—$NO_2$".

The term "cyano" as used herein, represents a group of formula "—CN".

The term "amide" as used herein, represents a group of formula "—$C(O)NR^xR^y$," wherein $R^x$ and $R^y$ can be the same or independently H, alkyl, aryl, cycloalkyl, cycloalkenyl, heterocycle as defined above.

The term "sulfonamide" as used herein, represents a group of formula "—$S(O)_2NR^xR^y$" wherein $R^x$ and $R^y$ can be the same or independently H, alkyl, aryl, cycloalkyl, cycloalkenyl, heterocycle as defined above.

The term "sulfoxide" as used herein, represents a group of formula "—S(O)—".

The term "phosphonic acid" as used herein, represents a group of formula "—$P(O)(OH)_2$".

The term "phosphoric acid" as used herein, represents a group of formula "—$OP(O)(OH)_2$".

The term "sulphonic acid" as used herein, represents a group of formula "—$S(O)_2OH$".

The formula "H", as used herein, represents a hydrogen atom.

The formula "O", as used herein, represents an oxygen atom.

The formula "N", as used herein, represents a nitrogen atom.

The formula "S", as used herein, represents a sulfur atom.

Functional groups may be protected in cases where the functional group interferes with the metathesis catalyst, and any of the protecting groups commonly used in the art may be employed. Acceptable protecting groups may be found, for example, in Greene et al., Protective Groups in Organic Synthesis, 3rd Ed. (New York: Wiley, 1999). Examples of protecting groups include acetals, cyclic acetals, boronate esters (boronates), cyclic boronate esters (cyclic boronates), carbonates, or the like. Examples of protecting groups include cyclic acetals or cyclic boronate esters.

Olefin Metathesis Catalysts

In one embodiment, the invention provides a compound of Formula (I):

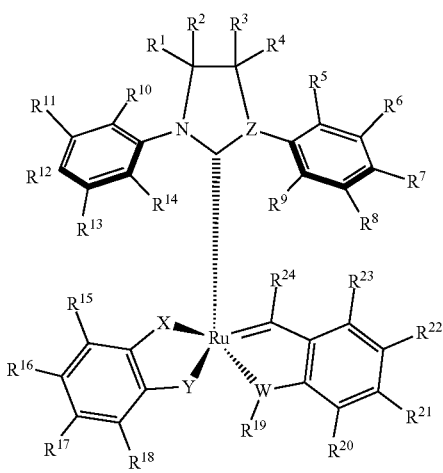

Formula (I)

X is O or S;
Y is O or S;
Z is N or $CR^{32}$;
W is O, $NR^{33}$ or S;
$R^1$ is hydrogen, optionally substituted $C_{1-24}$ alkyl, halogen, —$C(O)R^{25}$, —$OR^{26}$, CN, —$NR^{27}R^{28}$, $NO_2$, —$CF_3$, —$S(O)_m$ $R^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl or optionally substituted $C_{3-8}$ cycloalkenyl;
$R^2$ is hydrogen, optionally substituted $C_{1-24}$ alkyl, halogen, —$C(O)R^{25}$, —$OR^{26}$, CN, —$NR^{27}R^{28}$, $NO_2$, —$CF_3$, —$S(O)_m$ $R^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl, optionally substituted $C_{3-8}$ cycloalkenyl or together with $R^3$ may form a polycyclic ring;
$R^3$ is hydrogen, optionally substituted $C_{1-24}$ alkyl, halogen, —$C(O)R^{25}$, —$OR^{26}$, CN, —$NR^{27}R^{28}$, $NO_2$, —$CF_3$, —$S(O)_m$ $R^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl or optionally substituted $C_{3-8}$ cycloalkenyl or together with $R^2$ may form a polycyclic ring;
$R^4$ is hydrogen, optionally substituted $C_{1-24}$ alkyl, halogen, —$C(O)R^{25}$, —$OR^{26}$, CN, —$NR^{27}R^{28}$, $NO_2$, —$CF_3$, —$S(O)_m$ $R^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl or optionally substituted $C_{3-8}$ cycloalkenyl;
$R^5$ is hydrogen, optionally substituted $C_{1-24}$ alkyl, halogen, —$C(O)R^{25}$, —$OR^{26}$, CN, —$NR^{27}R^{28}$, $NO_2$, —$CF_3$, —$S(O)_m$ $R^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl or optionally substituted $C_{3-8}$ cycloalkenyl;
$R^6$ is hydrogen, optionally substituted $C_{1-24}$ alkyl, halogen, —$C(O)R^{25}$, —$OR^{26}$, CN, —$NR^{27}R^{28}$, $NO_2$, —$CF_3$, —$S(O)_m$ $R^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl or optionally substituted $C_{3-8}$ cycloalkenyl;
$R^7$ is hydrogen, optionally substituted $C_{1-24}$ alkyl, halogen, —$C(O)R^{25}$, —$OR^{26}$, CN, —$NR^{27}R^{28}$, $NO_2$, —$CF_3$, —$S(O)_m$ $R^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl or optionally substituted $C_{3-8}$ cycloalkenyl;
$R^8$ is hydrogen, optionally substituted $C_{1-24}$ alkyl, halogen, —$C(O)R^{25}$, —$OR^{26}$, CN, —$NR^{27}R^{28}$, $NO_2$, —$CF_3$, —$S(O)_m$ $R^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl or optionally substituted $C_{3-8}$ cycloalkenyl;
$R^9$ is hydrogen, optionally substituted $C_{1-24}$ alkyl, halogen, —$C(O)R^{25}$, —$OR^{26}$, CN, —$NR^{27}R^{28}$, $NO_2$, —$CF_3$, —$S(O)_m$ $R^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl or optionally substituted $C_{3-8}$ cycloalkenyl;
$R^{10}$ is hydrogen, optionally substituted $C_{1-24}$ alkyl, halogen, —$C(O)R^{25}$, —$OR^{26}$, CN, —$NR^{27}R^{28}$, $NO_2$, —$CF_3$, —$S(O)_m$ $R^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl or optionally substituted $C_{3-8}$ cycloalkenyl;
$R^{11}$ is hydrogen, optionally substituted $C_{1-24}$ alkyl, halogen, —$C(O)R^{25}$, —$OR^{26}$, CN, —$NR^{27}R^{28}$, $NO_2$, —$CF_3$, —$S(O)_m$ $R^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl or optionally substituted $C_{3-8}$ cycloalkenyl;
$R^{12}$ is hydrogen, optionally substituted $C_{1-24}$ alkyl, halogen, —$C(O)R^{25}$, —$OR^{26}$, CN, —$NR^{27}R^{28}$, $NO_2$, —$CF_3$, —$S(O)_m$ $R^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl or optionally substituted $C_{3-8}$ cycloalkenyl;
$R^{13}$ is hydrogen, optionally substituted $C_{1-24}$ alkyl, halogen, —$C(O)R^{25}$, —$OR^{26}$, CN, —$NR^{27}R^{28}$, $NO_2$, —$CF_3$, —$S(O)_m$ $R^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl or optionally substituted $C_{3-8}$ cycloalkenyl;
$R^{14}$ is hydrogen, optionally substituted $C_{1-24}$ alkyl, halogen, —$C(O)R^{25}$, —$OR^{26}$, CN, —$NR^{27}R^{28}$, $NO_2$, —$CF_3$, —$S(O)_m$ $R^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl or optionally substituted $C_{3-8}$ cycloalkenyl;
$R^{15}$ is hydrogen, optionally substituted $C_{1-24}$ alkyl, halogen, —$C(O)R^{25}$, —$OR^{26}$, CN, —$NR^{27}R^{28}$, $NO_2$, —$CF_3$, —$S(O)_m$ $R^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl or optionally substituted $C_{3-8}$ cycloalkenyl, or together with $R^{16}$ may form an optionally substituted polycyclic ring;
$R^{16}$ is hydrogen, optionally substituted $C_{1-24}$ alkyl, halogen, —$C(O)R^{25}$, —$OR^{26}$, CN, —$NR^{27}R^{28}$, $NO_2$, —$CF_3$, —$S(O)_m$ $R^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl or optionally substituted $C_{3-8}$ cycloalkenyl, or together with $R^{15}$ may form an optionally substituted polycyclic ring;
$R^{17}$ is hydrogen, optionally substituted $C_{1-24}$ alkyl, halogen, —$C(O)R^{25}$, —$OR^{26}$, CN, —$NR^{27}R^{28}$, $NO_2$, —$CF_3$, —$S(O)_m$ $R^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl or optionally substituted $C_{3-8}$ cycloalkenyl, or together with $R^{18}$ may form an optionally substituted polycyclic ring;

$R^{18}$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl, or together with $R^{18}$ may form an optionally substituted polycyclic ring;

$R^{19}$ is hydrogen, optionally substituted $C_{1-24}$ alkyl, —C(O)$R^{25}$, optionally substituted heterocycle, optionally substituted $C_{3-8}$ cycloalkyl, optionally substituted $C_{5-24}$ aryl or optionally substituted $C_{3-8}$ cycloalkenyl;

$R^{20}$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{21}$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{22}$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{23}$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{24}$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{25}$ is OH, O$R^{30}$, N$R^{27}R^{28}$, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl, $R^{26}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{27}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{28}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{29}$ is hydrogen, optionally substituted $C_{1-24}$ alkyl, O$R^{26}$, —N$R^{27}R^{28}$, optionally substituted heterocycle, optionally substituted $C_{3-8}$ cycloalkyl, optionally substituted $C_{5-24}$ aryl or optionally substituted $C_{3-8}$ cycloalkenyl;

$R^{30}$ is optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{31}$ is hydrogen, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{32}$ is hydrogen, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{33}$ is hydrogen, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl; and m is 1 or 2.

In another embodiment, the invention provides a catalyst represented by Formula (I) wherein:

X is O or S;
Y is O or S;
Z is N or C$R^{32}$;
W is O, N$R^{33}$ or S;

$R^1$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^2$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl, optionally substituted $C_{3-8}$ cycloalkenyl or together with $R^3$ may form a polycyclic ring;

$R^3$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl or together with $R^2$ may form a polycyclic ring;

$R^4$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^5$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^6$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^7$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^8$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^9$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{10}$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{11}$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{12}$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{13}$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{14}$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{15}$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{16}$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{17}$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl, or together with $R^{18}$ may form a polycyclic ring;

$R^{18}$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl, or together with $R^{17}$ may form a polycyclic ring;

$R^{19}$ is hydrogen, optionally substituted $C_{1-24}$ alkyl, —C(O)$R^{25}$, optionally substituted heterocycle, optionally substituted $C_{3-8}$ cycloalkyl, optionally substituted $C_{5-24}$ aryl or optionally substituted $C_{3-8}$ cycloalkenyl;

$R^{20}$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{21}$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{22}$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{23}$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{24}$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{25}$ is OH, O$R^{30}$, N$R^{27}R^{28}$, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl, $R^{26}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{27}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{28}$ is H, optionally substituted $C_{1-8}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{29}$ is hydrogen, optionally substituted $C_{1-24}$ alkyl, O$R^{26}$, —N$R^{27}R^{28}$, optionally substituted heterocycle, optionally substituted $C_{3-8}$ cycloalkyl, optionally substituted $C_{5-24}$ aryl or optionally substituted $C_{3-8}$ cycloalkenyl;

$R^{30}$ is optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{31}$ is hydrogen, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{32}$ is hydrogen, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{33}$ is hydrogen, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl; and m is 1 or 2.

In another embodiment, the invention provides a catalyst represented by Formula (I) wherein:

X is S;
Y is S;
Z is N or $CR^{32}$;
W is O;

$R^1$ is hydrogen, optionally substituted $C_{1-24}$ alkyl, halogen, —$C(O)R^{25}$, —$OR^{26}$, CN, —$NR^{27}R^{28}$, $NO_2$, —$CF_3$, —$S(O)_m R^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^2$ is hydrogen, optionally substituted $C_{1-24}$ alkyl, halogen, —$C(O)R^{25}$, —$OR^{26}$, CN, —$NR^{27}R^{28}$, $NO_2$, —$CF_3$, —$S(O)_m R^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl, optionally substituted $C_{3-8}$ cycloalkenyl or together with $R^3$ may form a polycyclic ring;

$R^3$ is hydrogen, optionally substituted $C_{1-24}$ alkyl, halogen, —$C(O)R^{25}$, —$OR^{26}$, CN, —$NR^{27}R^{28}$, $NO_2$, —$CF_3$, —$S(O)_m R^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl or optionally substituted $C_{3-8}$ cycloalkenyl or together with $R^2$ may form a polycyclic ring;

$R^4$ is hydrogen, optionally substituted $C_{1-24}$ alkyl, halogen, —$C(O)R^{25}$, —$OR^{26}$, CN, —$NR^{27}R^{28}$, $NO_2$, —$CF_3$, —$S(O)_m R^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^5$ is hydrogen, optionally substituted $C_{1-24}$ alkyl, halogen, —$C(O)R^{25}$, —$OR^{26}$, CN, —$NR^{27}R^{28}$, $NO_2$, —$CF_3$, —$S(O)_m R^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^6$ is hydrogen, optionally substituted $C_{1-24}$ alkyl, halogen, —$C(O)R^{25}$, —$OR^{26}$, CN, —$NR^{27}R^{28}$, $NO_2$, —$CF_3$, —$S(O)_m R^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^7$ is hydrogen, optionally substituted $C_{1-24}$ alkyl, halogen, —$C(O)R^{25}$, —$OR^{26}$, CN, —$NR^{27}R^{28}$, $NO_2$, —$CF_3$, —$S(O)_m R^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^8$ is hydrogen, optionally substituted $C_{1-24}$ alkyl, halogen, —$C(O)R^{25}$, —$OR^{26}$, CN, —$NR^{27}R^{28}$, $NO_2$, —$CF_3$, —$S(O)_m R^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^9$ is hydrogen, optionally substituted $C_{1-24}$ alkyl, halogen, —$C(O)R^{25}$, —$OR^{26}$, CN, —$NR^{27}R^{28}$, $NO_2$, —$CF_3$, —$S(O)_m R^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{10}$ is hydrogen, optionally substituted $C_{1-24}$ alkyl, halogen, —$C(O)R^{25}$, —$OR^{26}$, CN, —$NR^{27}R^{28}$, $NO_2$, —$CF_3$, —$S(O)_m R^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{11}$ is hydrogen, optionally substituted $C_{1-24}$ alkyl, halogen, —$C(O)R^{25}$, —$OR^{26}$, CN, —$NR^{27}R^{28}$, $NO_2$, —$CF_3$, —$S(O)_m R^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{12}$ is hydrogen, optionally substituted $C_{1-24}$ alkyl, halogen, —$C(O)R^{25}$, —$OR^{26}$, CN, —$NR^{27}R^{28}$, $NO_2$, —$CF_3$, —$S(O)_m R^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{13}$ is hydrogen, optionally substituted $C_{1-24}$ alkyl, halogen, —$C(O)R^{25}$, —$OR^{26}$, CN, —$NR^{27}R^{28}$, $NO_2$, —$CF_3$, —$S(O)_m R^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{14}$ is hydrogen, optionally substituted $C_{1-24}$ alkyl, halogen, —$C(O)R^{25}$, —$OR^{26}$, CN, —$NR^{27}R^{28}$, $NO_2$, —$CF_3$, —$S(O)_m R^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{15}$ is hydrogen, optionally substituted $C_{1-24}$ alkyl, halogen, —$C(O)R^{25}$, —$OR^{26}$, CN, —$NR^{27}R^{28}$, $NO_2$, —$CF_3$, —$S(O)_m R^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl or optionally substituted $C_{3-8}$ cycloalkenyl, or together with $R^{16}$ may form an optionally substituted polycyclic ring;

$R^{16}$ is hydrogen, optionally substituted $C_{1-24}$ alkyl, halogen, —$C(O)R^{25}$, —$OR^{26}$, CN, —$NR^{27}R^{28}$, $NO_2$, —$CF_3$, —$S(O)_m R^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl or optionally substituted $C_{3-8}$ cycloalkenyl, or together with $R^{15}$ may form an optionally substituted polycyclic ring;

$R^{17}$ is hydrogen, optionally substituted $C_{1-24}$ alkyl, halogen, —$C(O)R^{25}$, —$OR^{26}$, CN, —$NR^{27}R^{28}$, $NO_2$, —$CF_3$, —$S(O)_m R^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl or optionally substituted $C_{3-8}$ cycloalkenyl, or together with $R^{18}$ may form an optionally substituted polycyclic ring;

$R^{18}$ is hydrogen, optionally substituted $C_{1-24}$ alkyl, halogen, —$C(O)R^{25}$, —$OR^{26}$, CN, —$NR^{27}R^{28}$, $NO_2$, —$CF_3$, —$S(O)_m R^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl or optionally substituted $C_{3-8}$ cycloalkenyl, or together with $R^{17}$ may form an optionally substituted polycyclic ring;

$R^{19}$ is hydrogen, optionally substituted $C_{1-24}$ alkyl, —$C(O)R^{25}$, optionally substituted heterocycle, optionally substituted $C_{3-8}$ cycloalkyl, optionally substituted $C_{5-24}$ aryl or optionally substituted $C_{3-8}$ cycloalkenyl;

$R^{20}$ is hydrogen, optionally substituted $C_{1-24}$ alkyl, halogen, —$C(O)R^{25}$, —$OR^{26}$, CN, —$NR^{27}R^{28}$, $NO_2$, —$CF_3$, —$S(O)_m R^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{21}$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{22}$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{23}$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{24}$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{25}$ is OH, O$R^{30}$, N$R^{27}R^{28}$, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl, $R^{26}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{27}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{28}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{29}$ is hydrogen, optionally substituted $C_{1-24}$ alkyl, O$R^{26}$, —N$R^{27}R^{28}$, optionally substituted heterocycle, optionally substituted $C_{3-8}$ cycloalkyl, optionally substituted $C_{5-24}$ aryl or optionally substituted $C_{3-8}$ cycloalkenyl;

$R^{30}$ is optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{31}$ is hydrogen, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{32}$ is hydrogen, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl; and m is 1 or 2.

In another embodiment, the invention provides a catalyst represented by Formula (I) wherein:
X is S;
Y is S;
Z is N;
W is O;
$R^1$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^2$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl, optionally substituted $C_{3-8}$ cycloalkenyl or together with $R^3$ may form a polycyclic ring;

$R^3$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl or together with $R^2$ may form a polycyclic ring;

$R^4$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^5$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^6$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^7$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^8$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^9$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{10}$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{11}$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{12}$ is hydrogen, optionally substituted $C_{1-24}$ alkyl, halogen, $-C(O)R^{25}$, $-OR^{26}$, CN, $-NR^{27}R^{28}$, $NO_2$, $-CF_3$, $-S(O)_m R^{29}$, $-P(O)(OH)_2$, $-OP(O)(OH)_2$, $-SR^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{13}$ is hydrogen, optionally substituted $C_{1-24}$ alkyl, halogen, $-C(O)R^{25}$, $-OR^{26}$, CN, $-NR^{27}R^{28}$, $NO_2$, $-CF_3$, $-S(O)_m R^{29}$, $-P(O)(OH)_2$, $-OP(O)(OH)_2$, $-SR^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{14}$ is hydrogen, optionally substituted $C_{1-24}$ alkyl, halogen, $-C(O)R^{25}$, $-OR^{26}$, CN, $-NR^{27}R^{28}$, $NO_2$, $-CF_3$, $-S(O)_m R^{29}$, $-P(O)(OH)_2$, $-OP(O)(OH)_2$, $-SR^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{15}$ is hydrogen, optionally substituted $C_{1-24}$ alkyl, halogen, $-C(O)R^{25}$, $-OR^{26}$, CN, $-NR^{27}R^{28}$, $NO_2$, $-CF_3$, $-S(O)_m R^{29}$, $-P(O)(OH)_2$, $-OP(O)(OH)_2$, $-SR^{31}$, optionally substituted heterocycle, optionally substituted $C_{3-8}$ cycloalkyl, optionally substituted $C_{5-24}$ aryl or optionally substituted $C_{3-8}$ cycloalkenyl, or together with $R^{16}$ may form an optionally substituted polycyclic ring;

$R^{16}$ is hydrogen, optionally substituted $C_{1-24}$ alkyl, halogen, $-C(O)R^{25}$, $-OR^{26}$, CN, $-NR^{27}R^{28}$, $NO_2$, $-CF_3$, $-S(O)_m R^{29}$, $-P(O)(OH)_2$, $-OP(O)(OH)_2$, $-SR^{31}$, optionally substituted heterocycle, optionally substituted $C_{3-8}$ cycloalkyl, optionally substituted $C_{5-24}$ aryl or optionally substituted $C_{3-8}$ cycloalkenyl, or together with $R^{15}$ may form an optionally substituted polycyclic ring;

$R^{17}$ is hydrogen, optionally substituted $C_{1-24}$ alkyl, halogen, $-C(O)R^{25}$, $-OR^{26}$, CN, $-NR^{27}R^{28}$, $NO_2$, $-CF_3$, $-S(O)_m R^{29}$, $-P(O)(OH)_2$, $-OP(O)(OH)_2$, $-SR^{31}$, optionally substituted heterocycle, optionally substituted $C_{3-8}$ cycloalkyl, optionally substituted $C_{5-24}$ aryl or optionally substituted $C_{3-8}$ cycloalkenyl, or together with $R^{18}$ may form an optionally substituted polycyclic ring;

$R^{18}$ is hydrogen, optionally substituted $C_{1-24}$ alkyl, halogen, $-C(O)R^{25}$, $-OR^{26}$, CN, $-NR^{27}R^{28}$, $NO_2$, $-CF_3$, $-S(O)_m R^{29}$, $-P(O)(OH)_2$, $-OP(O)(OH)_2$, $-SR^{31}$, optionally substituted heterocycle, optionally substituted $C_{3-8}$ cycloalkyl, optionally substituted $C_{5-24}$ aryl or optionally substituted $C_{3-8}$ cycloalkenyl, or together with $R^{17}$ may form an optionally substituted polycyclic ring;

$R^{19}$ is hydrogen, optionally substituted $C_{1-24}$ alkyl, $-C(O)R^{25}$, optionally substituted heterocycle, optionally substituted $C_{3-8}$ cycloalkyl, optionally substituted $C_{5-24}$ aryl or optionally substituted $C_{3-8}$ cycloalkenyl;

$R^{20}$ is hydrogen, optionally substituted $C_{1-24}$ alkyl, halogen, $-C(O)R^{25}$, $-OR^{26}$, CN, $-NR^{27}R^{28}$, $NO_2$, $-CF_3$, $-S(O)_m R^{29}$, $-P(O)(OH)_2$, $-OP(O)(OH)_2$, $-SR^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{21}$ is hydrogen, optionally substituted $C_{1-24}$ alkyl, halogen, $-C(O)R^{25}$, $-OR^{26}$, CN, $-NR^{27}R^{28}$, $NO_2$, $-CF_3$, $-S(O)_m R^{29}$, $-P(O)(OH)_2$, $-OP(O)(OH)_2$, $-SR^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{22}$ is hydrogen, optionally substituted $C_{1-24}$ alkyl, halogen, $-C(O)R^{25}$, $-OR^{26}$, CN, $-NR^{27}R^{28}$, $NO_2$, $-CF_3$, $-S(O)_m R^{29}$, $-P(O)(OH)_2$, $-OP(O)(OH)_2$, $-SR^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{23}$ is hydrogen, optionally substituted $C_{1-24}$ alkyl, halogen, $-C(O)R^{25}$, $-OR^{26}$, CN, $-NR^{27}R^{28}$, $NO_2$, $-CF_3$, $-S(O)_m R^{29}$, $-P(O)(OH)_2$, $-OP(O)(OH)_2$, $-SR^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{24}$ is hydrogen, optionally substituted $C_{1-24}$ alkyl, halogen, $-C(O)R^{25}$, $-OR^{26}$, CN, $-NR^{27}R^{28}$, $NO_2$, $-CF_3$, $-S(O)_m R^{29}$, $-P(O)(OH)_2$, $-OP(O)(OH)_2$, $-SR^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{25}$ is OH, $OR^{30}$, $NR^{27}R^{28}$, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl, $R^{26}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{27}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{28}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{29}$ is hydrogen, optionally substituted $C_{1-24}$ alkyl, $OR^{26}$, $-NR^{27}R^{28}$, optionally substituted heterocycle, optionally substituted $C_{3-8}$ cycloalkyl, optionally substituted $C_{5-24}$ aryl or optionally substituted $C_{3-8}$ cycloalkenyl;

$R^{30}$ is optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{31}$ is hydrogen, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{32}$ is hydrogen, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl; and m is 1 or 2.

In one embodiment, the invention provides a catalyst represented by Formula (I) wherein:

X is S;
Y is S;
Z is $CR^{32}$;
W is O;
$R^1$ is hydrogen, optionally substituted $C_{1-24}$ alkyl, halogen, $-C(O)R^{25}$, $-OR^{26}$, CN, $-NR^{27}R^{28}$, $NO_2$, $-CF_3$, $-S(O)_m R^{29}$, $-P(O)(OH)_2$, $-OP(O)(OH)_2$, $-SR^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^2$ is hydrogen, optionally substituted $C_{1-24}$ alkyl, halogen, $-C(O)R^{25}$, $-OR^{26}$, CN, $-NR^{27}R^{28}$, $NO_2$, $-CF_3$, $-S(O)_m R^{29}$, $-P(O)(OH)_2$, $-OP(O)(OH)_2$, $-SR^{31}$, optionally substituted heterocycle, optionally substituted $C_{3-8}$ cycloalkyl, optionally substituted $C_{5-24}$ aryl, optionally substituted $C_{3-8}$ cycloalkenyl or together with $R^3$ may form a polycyclic ring;

$R^3$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl or together with $R^2$ may form a polycyclic ring;

$R^4$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^5$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^6$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^7$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^8$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^9$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{10}$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{11}$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{12}$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{13}$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{14}$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{15}$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl, or together with $R^{16}$ may form an optionally substituted polycyclic ring;

$R^{16}$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl, or together with $R^{15}$ may form an optionally substituted polycyclic ring;

$R^{17}$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl, or together with $R^{18}$ may form an optionally substituted polycyclic ring;

$R^{18}$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl, or together with $R^{17}$ may form an optionally substituted polycyclic ring;

$R^{19}$ is hydrogen, optionally substituted $C_{1-24}$ alkyl, —C(O)$R^{25}$, optionally substituted heterocycle, optionally substituted $C_{3-8}$ cycloalkyl, optionally substituted $C_{5-24}$ aryl or optionally substituted $C_{3-8}$ cycloalkenyl;

$R^{20}$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{21}$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{22}$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{23}$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{24}$ is hydrogen, optionally substituted $C_{1-24}$ alkyl, halogen, —C(O)$R^{25}$, —O$R^{26}$, CN, —N$R^{27}R^{28}$, NO$_2$, —CF$_3$, —S(O)$_m$ $R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{25}$ is OH, $OR^{30}$, $NR^{27}R^{28}$, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl, $R^{26}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{27}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{28}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{29}$ is hydrogen, optionally substituted $C_{1-24}$ alkyl, $OR^{26}$, $—NR^{27}R^{28}$, optionally substituted heterocycle, optionally substituted $C_{3-8}$ cycloalkyl, optionally substituted $C_{5-24}$ aryl or optionally substituted $C_{3-8}$ cycloalkenyl;

$R^{30}$ is optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{31}$ is hydrogen, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{32}$ is hydrogen, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl; and m is 1 or 2.

In one embodiment, the invention provides a catalyst represented by Formula (I) wherein: X is S; Y is S; Z is N; W is O; $R^1$ is hydrogen or optionally substituted $C_{1-8}$ alkyl; $R^2$ is hydrogen or optionally substituted $C_{1-8}$ alkyl; $R^3$ is hydrogen or optionally substituted $C_{1-8}$ alkyl; $R^4$ is hydrogen or optionally substituted $C_{1-8}$ alkyl; $R^5$ is hydrogen, optionally substituted $C_{1-8}$ alkyl or halogen; $R^6$ is hydrogen, optionally substituted $C_{1-8}$ alkyl or halogen; $R^7$ is hydrogen, optionally substituted $C_{1-8}$ alkyl or halogen; $R^8$ is hydrogen, optionally substituted $C_{1-8}$ alkyl or halogen; $R^9$ is hydrogen, optionally substituted $C_{1-8}$ alkyl or halogen; $R^{10}$ is hydrogen, optionally substituted $C_{1-8}$ alkyl or halogen; $R^{11}$ is hydrogen, optionally substituted $C_{1-8}$ alkyl or halogen; $R^{12}$ is hydrogen, optionally substituted $C_{1-8}$ alkyl or halogen; $R^{13}$ is hydrogen, optionally substituted $C_{1-8}$ alkyl or halogen; $R^{14}$ is hydrogen, optionally substituted $C_{1-8}$ alkyl or halogen; $R^{15}$ is hydrogen, optionally substituted $C_{1-8}$ alkyl or halogen, or together with $R^{16}$ may form an optionally substituted polycyclic ring; $R^{16}$ is hydrogen, optionally substituted $C_{1-8}$ alkyl or halogen, or together with $R^{15}$ may form an optionally substituted polycyclic ring; $R^{17}$ is hydrogen, optionally substituted $C_{1-8}$ alkyl, halogen, or together with $R^{18}$ may form an optionally substituted polycyclic ring; $R^{18}$ is hydrogen, optionally substituted $C_{6-10}$ aryl, optionally substituted $C_{1-8}$ alkyl, halogen, or together with $R^{17}$ may form an optionally substituted polycyclic ring; $R^{19}$ is optionally substituted $C_{1-8}$ alkyl; $R^{20}$ is hydrogen or optionally substituted $C_{6-10}$ aryl; $R^{21}$ is hydrogen; $R^{22}$ is hydrogen; $R^{23}$ is hydrogen; and $R^{24}$ is hydrogen.

In one embodiment, the invention provides a catalyst represented by Formula (I) wherein: X is S; Y is S; Z is N; W is O; $R^1$ is hydrogen or optionally substituted $C_{1-8}$ alkyl; $R^2$ is hydrogen or optionally substituted $C_{1-8}$ alkyl; $R^3$ is hydrogen; $R^4$ is hydrogen; $R^5$ is hydrogen, optionally substituted $C_{1-8}$ alkyl or halogen; $R^6$ is hydrogen or optionally substituted $C_{1-8}$ alkyl; $R^7$ is hydrogen, optionally substituted $C_{1-8}$ alkyl or halogen; $R^8$ is hydrogen or optionally substituted $C_{1-8}$ alkyl; $R^9$ is hydrogen, optionally substituted $C_{1-8}$ alkyl or halogen; $R^{10}$ is hydrogen, optionally substituted $C_{1-8}$ alkyl or halogen; $R^{11}$ is hydrogen or optionally substituted $C_{1-8}$ alkyl; $R^{12}$ is hydrogen, optionally substituted $C_{1-8}$ alkyl or halogen; $R^{13}$ is hydrogen or optionally substituted $C_{1-8}$ alkyl; $R^{14}$ is hydrogen, optionally substituted $C_{1-8}$ alkyl or halogen; $R^{15}$ is hydrogen or halogen; $R^{16}$ is hydrogen; $R^{17}$ is hydrogen or together with $R^{18}$ may form a polycyclic ring; $R^{18}$ is optionally substituted $C_{6-10}$ aryl, halogen or together with $R^{17}$ may form a polycyclic ring; $R^{19}$ is optionally substituted $C_{1-8}$ alkyl; $R^{20}$ is hydrogen or optionally substituted $C_{6-10}$ aryl; $R^{21}$ is hydrogen; $R^{22}$ is hydrogen; $R^{23}$ is hydrogen; and $R^{24}$ is hydrogen.

In one embodiment, the invention provides a catalyst represented by Formula (I) wherein: X is S; Y is S; Z is N; W is O; $R^1$ is hydrogen or optionally substituted $C_{1-8}$ alkyl; $R^2$ is hydrogen or optionally substituted $C_{1-8}$ alkyl; $R^3$ is hydrogen; $R^4$ is hydrogen; $R^5$ is hydrogen, optionally substituted $C_{1-8}$ alkyl or halogen; $R^6$ is hydrogen or optionally substituted $C_{1-8}$ alkyl; $R^7$ is hydrogen, optionally substituted $C_{1-8}$ alkyl or halogen; $R^8$ is hydrogen or optionally substituted $C_{1-8}$ alkyl; $R^9$ is hydrogen, optionally substituted $C_{1-8}$ alkyl or halogen; $R^{10}$ is hydrogen, optionally substituted $C_{1-8}$ alkyl or halogen; $R^{11}$ is hydrogen or optionally substituted $C_{1-8}$ alkyl; $R^{12}$ is hydrogen, optionally substituted $C_{1-8}$ alkyl or halogen; $R^{13}$ is hydrogen or optionally substituted $C_{1-8}$ alkyl; $R^{14}$ is hydrogen, optionally substituted $C_{1-8}$ alkyl or halogen; $R^{15}$ is hydrogen or halogen, or together with $R^{16}$ may form an optionally substituted polycyclic ring; $R^{16}$ is hydrogen, or together with $R^{15}$ may form an optionally substituted polycyclic ring; $R^{17}$ is hydrogen or together with $R^{18}$ may form an optionally substituted polycyclic ring; $R^{18}$ is optionally substituted $C_{6-10}$ aryl, halogen or together with $R^{17}$ may form an optionally substituted polycyclic ring; $R^{19}$ is optionally substituted $C_{1-8}$ alkyl; $R^{20}$ is hydrogen or optionally substituted $C_{6-10}$ aryl; $R^{21}$ is hydrogen; $R^{22}$ is hydrogen; $R^{23}$ is hydrogen; and $R^{24}$ is hydrogen.

In one embodiment, the invention provides a catalyst represented by Formula (I) wherein: X is S; Y is S; Z is N; W is O; $R^1$ is hydrogen; $R^2$ is hydrogen; $R^3$ is hydrogen; $R^4$ is hydrogen; $R^5$ is hydrogen, halogen or optionally substituted $C_{1-8}$ alkyl; $R^6$ is hydrogen or optionally substituted $C_{1-8}$ alkyl; $R^7$ is hydrogen or optionally substituted $C_{1-8}$ alkyl; $R^8$ is hydrogen or optionally substituted $C_{1-8}$ alkyl; $R^9$ is hydrogen, halogen or optionally substituted $C_{1-8}$ alkyl; $R^{10}$ is hydrogen, halogen or optionally substituted $C_{1-8}$ alkyl; $R^{11}$ is hydrogen or optionally substituted $C_{1-8}$ alkyl; $R^{12}$ is hydrogen or optionally substituted $C_{1-8}$ alkyl; $R^{13}$ is hydrogen or optionally substituted $C_{1-8}$ alkyl; $R^{14}$ is hydrogen, halogen or optionally substituted $C_{1-8}$ alkyl; $R^{15}$ is hydrogen or halogen, or together with $R^{16}$ may form an optionally substituted polycyclic ring; $R^{16}$ is hydrogen, or together with $R^{15}$ may form an optionally substituted polycyclic ring; $R^{17}$ is hydrogen or together with $R^{18}$ may form an optionally substituted polycyclic ring; $R^{18}$ is optionally substituted $C_{6-10}$ aryl, halogen, or together with $R^{17}$ may form an optionally substituted polycyclic ring; $R^{19}$ is optionally substituted $C_{1-8}$ alkyl; $R^{20}$ is hydrogen or optionally substituted $C_{6-10}$ aryl; $R^{21}$ is hydrogen; $R^{22}$ is hydrogen; $R^{23}$ is hydrogen; and $R^{24}$ is hydrogen.

In one embodiment, the invention provides a catalyst represented by Formula (I) wherein: X is S; Y is S; Z is N; W is O; $R^1$ is optionally substituted $C_{1-8}$ alkyl; $R^2$ is optionally substituted $C_{1-8}$ alkyl; $R^3$ is hydrogen; $R^4$ is hydrogen; $R^5$ is halogen; $R^6$ is hydrogen; $R^7$ is halogen; $R^8$ is hydrogen; $R^9$ is halogen; $R^{10}$ is halogen; $R^{11}$ is hydrogen; $R^{12}$ is hydrogen or halogen; $R^{13}$ is hydrogen; $R^{14}$ is halogen; $R^{15}$ is halogen; $R^{16}$ is hydrogen; $R^{17}$ is hydrogen or together with $R^{18}$ forms an optionally substituted naphtyl or phenantryl ring; $R^{18}$ is halogen or together with $R^{17}$ forms an optionally substituted naphtyl or phenantryl ring; $R^{19}$ is optionally substituted $C_{1-8}$ alkyl; $R^{20}$ is hydrogen; $R^{21}$ is hydrogen; $R^{22}$ is hydrogen; $R^{23}$ is hydrogen; and $R^{24}$ is hydrogen.

In one embodiment, the invention provides a catalyst represented by Formula (I) wherein: X is S; Y is S; Z is N; W is O; $R^1$ is hydrogen; $R^2$ is hydrogen; $R^3$ is hydrogen; $R^4$ is hydrogen; $R^5$ is hydrogen, F, methyl or i-Pr; $R^6$ is hydrogen or t-Bu; $R^7$ is hydrogen or methyl; $R^8$ is hydrogen or t-Bu; $R^9$ is hydrogen, F, methyl or i-Pr; $R^{10}$ is hydrogen, F, methyl or i-Pr; $R^{11}$ is hydrogen or t-Bu; $R^{12}$ is hydrogen or methyl; $R^{13}$ is hydrogen or t-Bu; $R^{14}$ is F, methyl, i-Pr or hydrogen; $R^{15}$ is hydrogen, methyl or Cl, or together with $R^{16}$ forms 2-phenyl-naphthyl or phenanthryl; $R^{16}$ is hydrogen, or together with $R^{15}$ forms 2-phenyl-naphthyl or phenanthryl; $R^{17}$ is hydrogen or together with $R^{18}$ forms 2-phenyl-naphthyl, phenanthryl, or methylphenantryl; $R^{18}$ is Cl, 3,5-dichloro-phenyl, phenyl, t-Bu or together with $R^{17}$ forms 2-phenyl-naphthyl, phenanthryl or methylphenantryl; $R^{19}$ is i-Pr; $R^{20}$ is hydrogen or phenyl; $R^{21}$ is hydrogen; $R^{22}$ is hydrogen; $R^{23}$ is hydrogen; and $R^{24}$ is hydrogen.

In one embodiment, the invention provides a catalyst represented by Formula (I) wherein: X is S; Y is S; Z is N; W is O; $R^1$ is methyl; $R^2$ is methyl; $R^3$ is hydrogen; $R^4$ is hydrogen; $R^5$ is F; $R^6$ is hydrogen; $R^7$ is hydrogen or F; $R^8$ is hydrogen; $R^9$ is F; $R^{10}$ is F; $R^{11}$ is hydrogen; $R^{12}$ is hydrogen or F; $R^{13}$ is hydrogen; $R^{14}$ is F; $R^{15}$ is Cl; $R^{16}$ is hydrogen; $R^{17}$ is hydrogen or together with $R^{18}$ forms naphtyl or phenanthryl; $R^{18}$ is hydrogen, Cl, or together with $R^{17}$ forms naphtyl or phenanthryl; $R^{19}$ is i-Pr; $R^{20}$ is hydrogen; $R^{21}$ is hydrogen; $R^{22}$ is hydrogen; $R^{23}$ is hydrogen; and $R^{24}$ is hydrogen.

In one embodiment, the invention provides a catalyst represented by Formula (I) wherein: X is S; Y is S; Z is N; W is O; $R^1$ is Me; $R^2$ is Me; $R^3$ is hydrogen; $R^4$ is hydrogen; $R^5$ is Me or F; $R^6$ is hydrogen; $R^7$ is hydrogen or F; $R^8$ is hydrogen; $R^9$ is hydrogen or F; $R^{10}$ is Me or F; $R^{11}$ is hydrogen; $R^{12}$ is hydrogen or F; $R^{13}$ is hydrogen; $R^{14}$ is hydrogen or F; $R^{15}$ is hydrogen or Cl; $R^{16}$ is hydrogen; $R^{17}$ is hydrogen or together with $R^{18}$ forms naphtyl or phenantryl; $R^{18}$ is Cl, phenyl or together with $R^{17}$ forms naphtyl or phenantryl; $R^{19}$ is i-Pr; $R^{20}$ is hydrogen; $R^{21}$ is hydrogen; $R^{22}$ is hydrogen; $R^{23}$ is hydrogen; and $R^{24}$ is hydrogen.

In one embodiment, the invention provides a catalyst represented by Formula (I) wherein: X is S; Y is S; Z is N; W is O; $R^1$ is hydrogen; $R^2$ is hydrogen; $R^3$ is hydrogen; $R^4$ is hydrogen; $R^5$ is Me, F or i-Pr; $R^6$ is hydrogen or t-Bu; $R^7$ is hydrogen or Me; $R^8$ is hydrogen or t-Bu; $R^9$ is hydrogen, Me, t-Bu, F or i-Pr; $R^{10}$ is hydrogen, Me, F or i-Pr; $R^{11}$ is hydrogen or t-Bu; $R^{12}$ is hydrogen or Me; $R^{13}$ is hydrogen or t-Bu; $R^{14}$ is hydrogen, Me, F or i-Pr; $R^{15}$ is hydrogen, methyl or Cl, or together with $R^{16}$ forms 2-phenyl-naphthyl or phenanthryl; $R^{16}$ is hydrogen, or together with $R^{15}$ forms 2-phenyl-naphthyl or phenanthryl; $R^{17}$ is hydrogen or together with $R^{18}$ forms 2-phenyl-naphthyl, naphtyl, phenanthryl, or methylphenantryl; $R^{18}$ is Cl, 3,5-dichloro-phenyl, phenyl, t-Bu or together with $R^{17}$ forms 2-phenyl-naphthyl, naphtyl, phenanthryl or methylphenantryl; $R^{15}$ is hydrogen or Cl; $R^{16}$ is hydrogen; $R^{17}$ is hydrogen or together with $R^{18}$ form an optionally substituted naphthyl or an optionally substituted phenanthryl ring; $R^{18}$ is Cl, phenyl or together with $R^{17}$ form an optionally substituted naphthyl or an optionally substituted phenanthryl ring; $R^{19}$ is i-Pr; $R^{20}$ is hydrogen is phenyl; $R^{21}$ is hydrogen; $R^{22}$ is hydrogen; $R^{23}$ is hydrogen; and $R^{24}$ is hydrogen.

In one embodiment, the invention provides a compound wherein the moiety

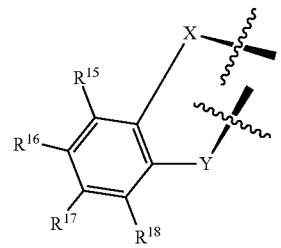

of Formula (I) is

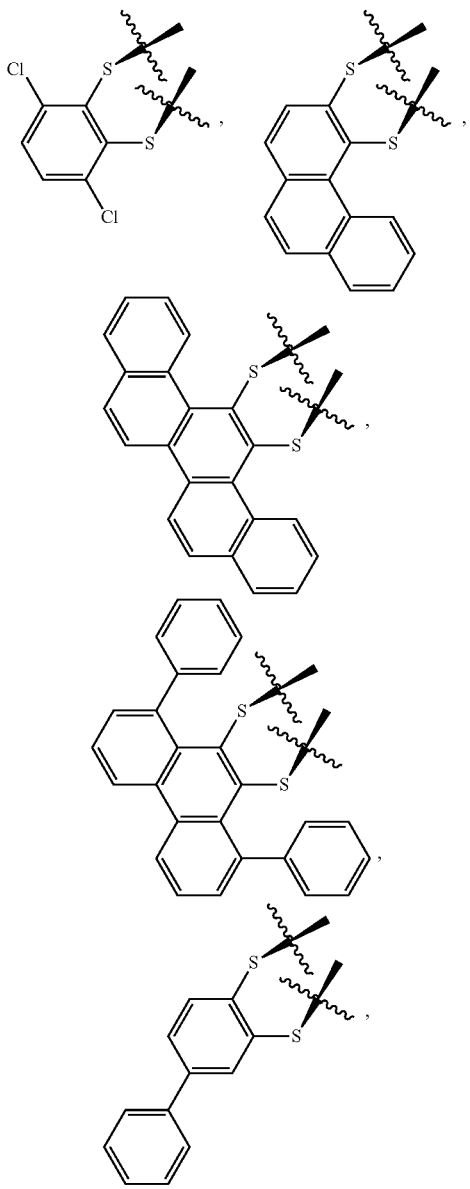

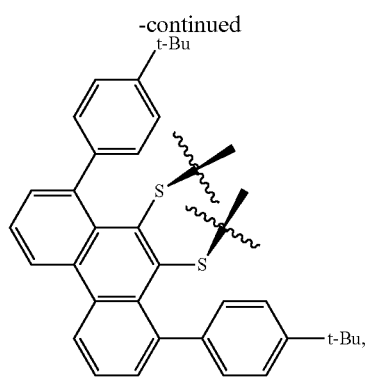
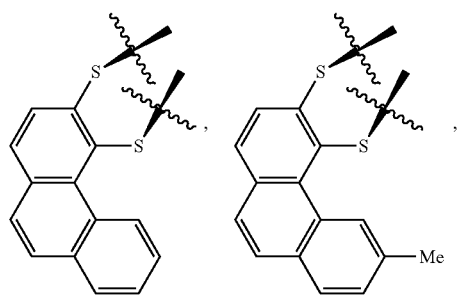
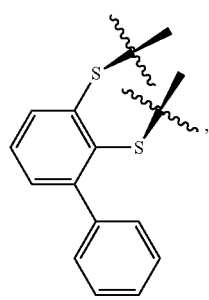
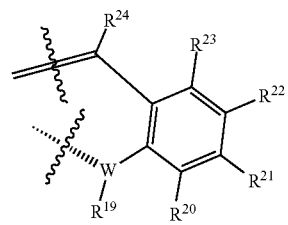
of Formula (I) is
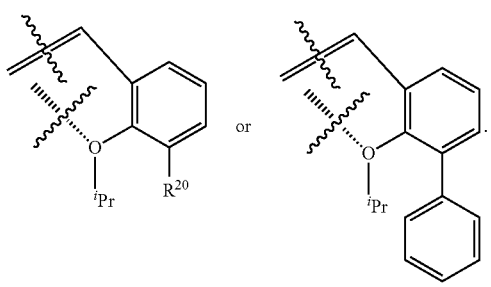
In one embodiment, the invention provides a compound wherein the moiety
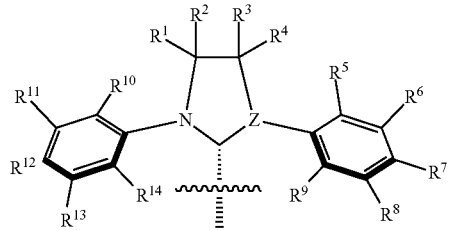
of Formula (I) is
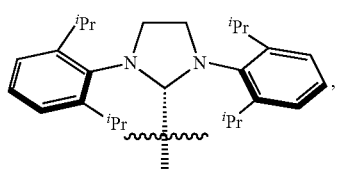
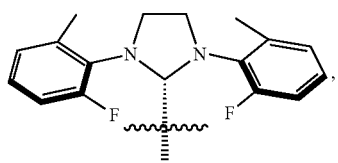
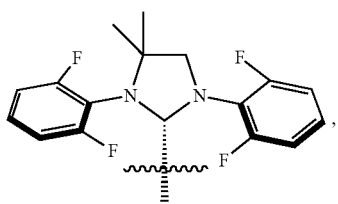
In one embodiment, the invention provides a compound wherein the moiety

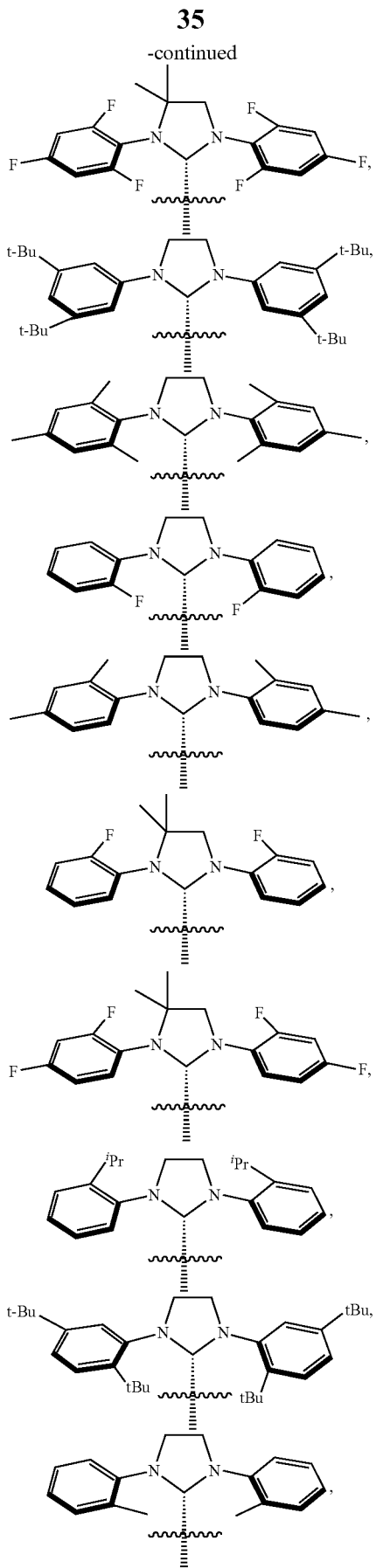
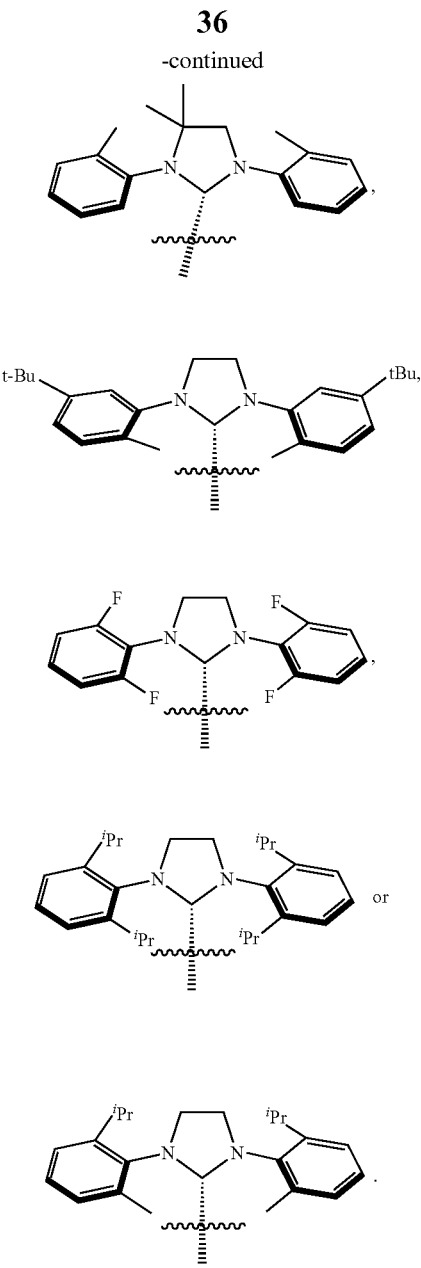
In one embodiment, the invention provides a compound of Formula (I) is selected from:
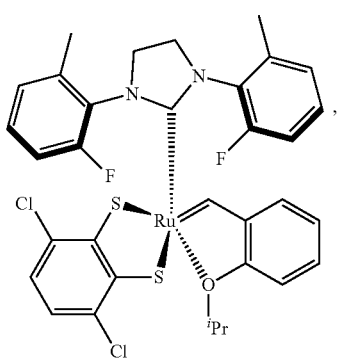
C745

-continued
C765
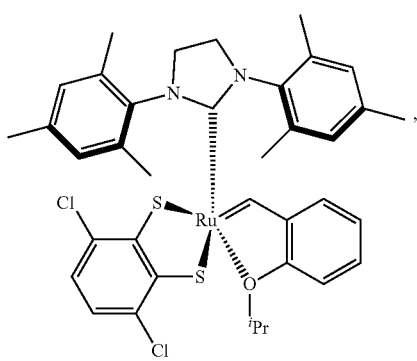
C781
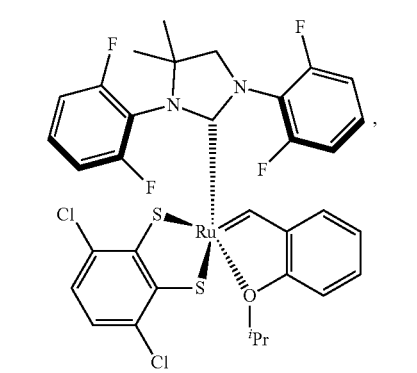
C817
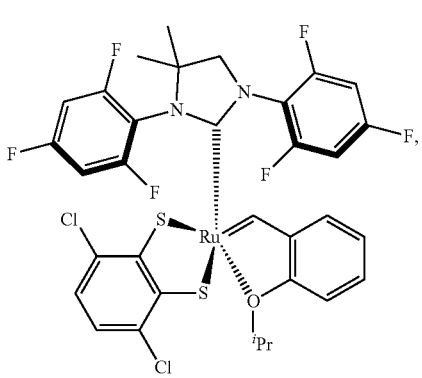
C849z
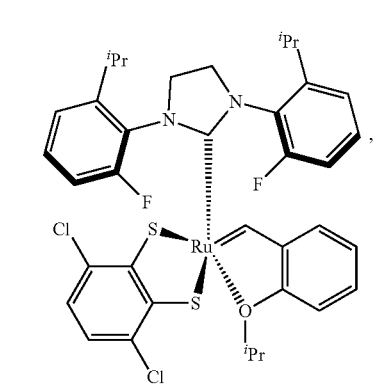
-continued
C905
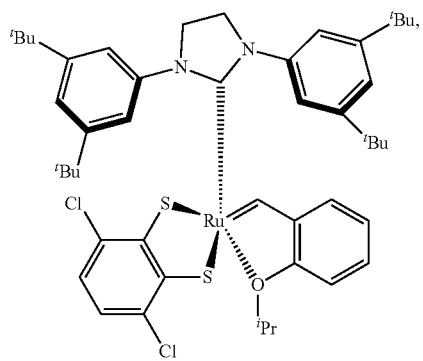
C773
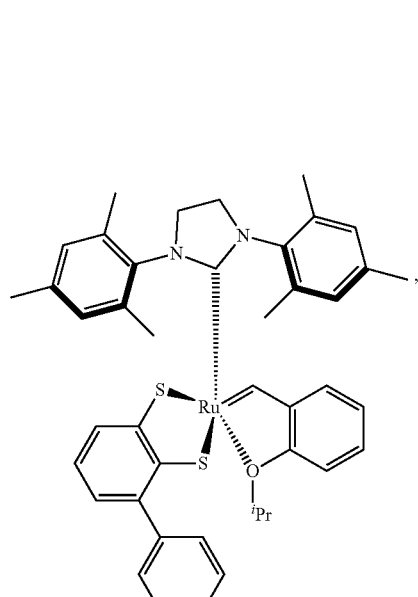
C747
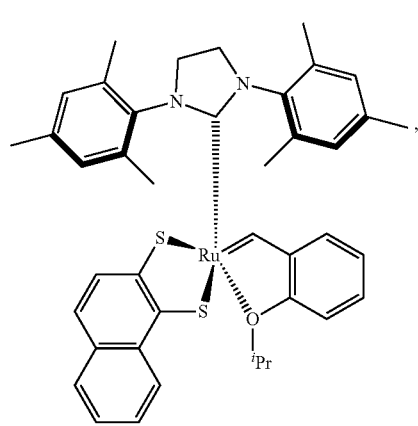

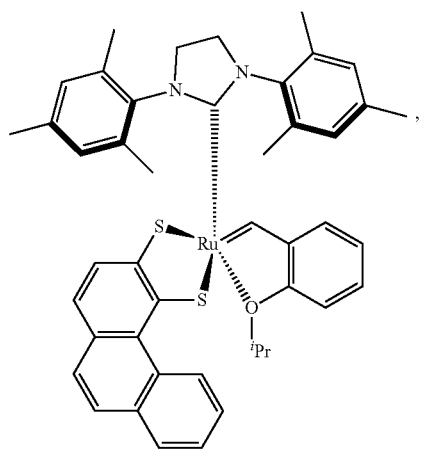 C797
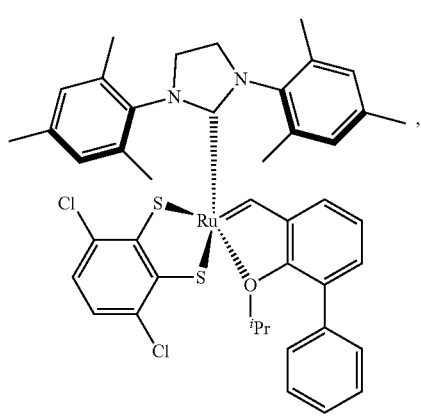 C841
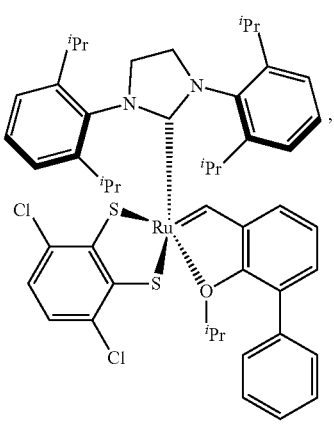 C925
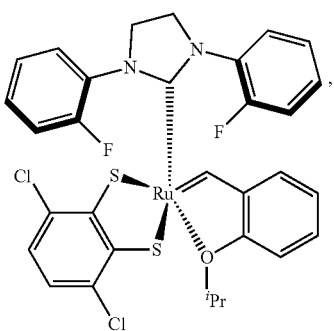 C718
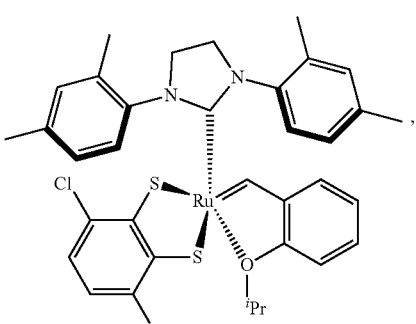 C738
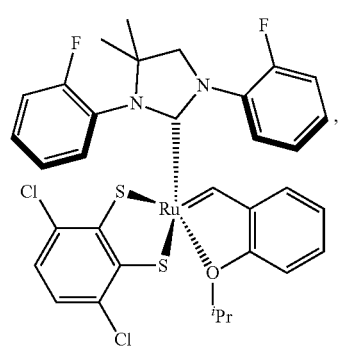 C746
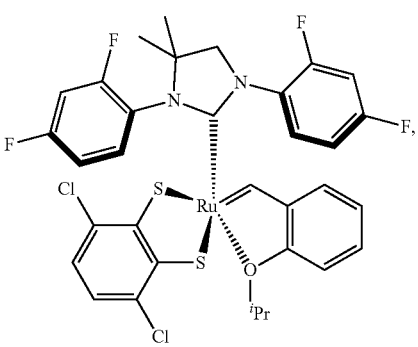 C782
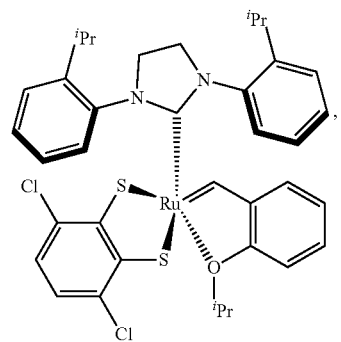 C766

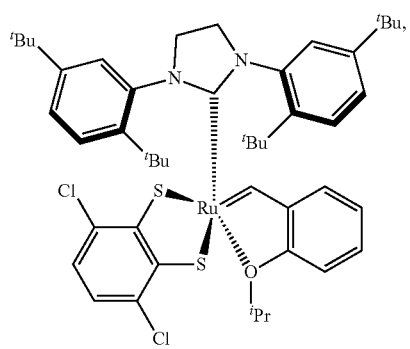
C905v2
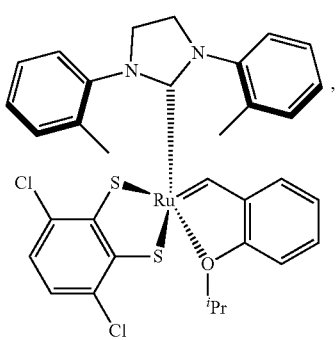
C710
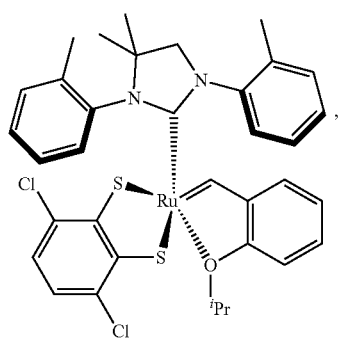
C738dm
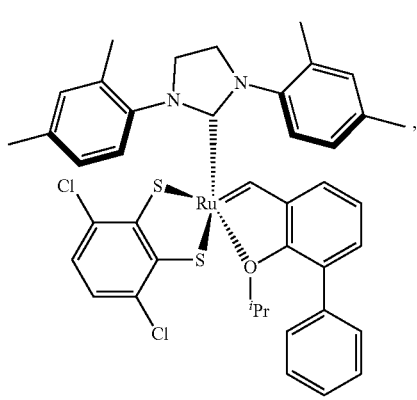
C814
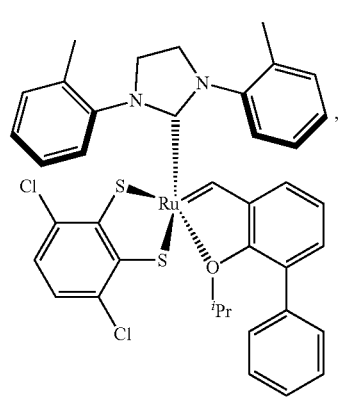
C786
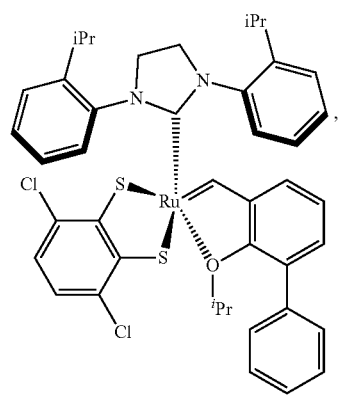
C842
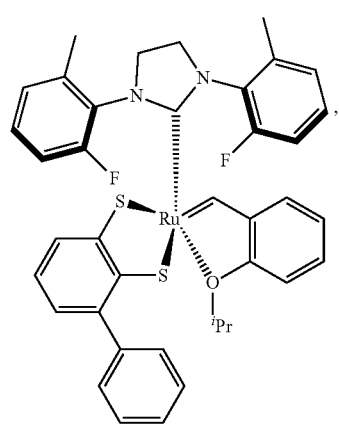
C753
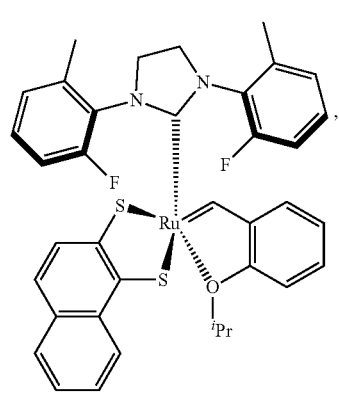
C727

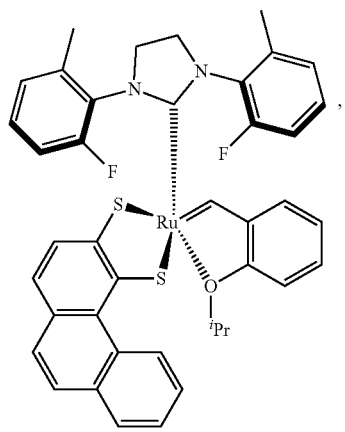 C777
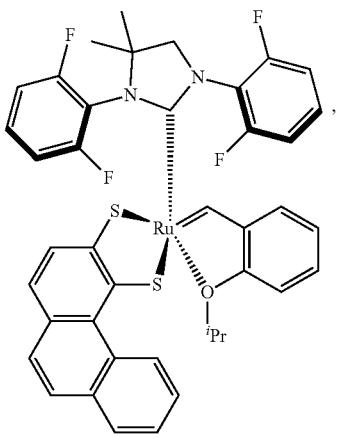 C813
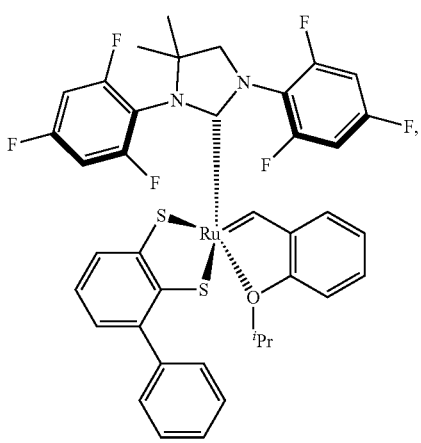 C789
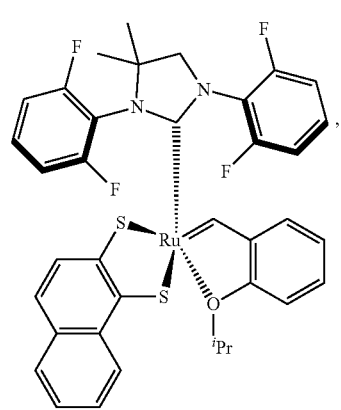 C825
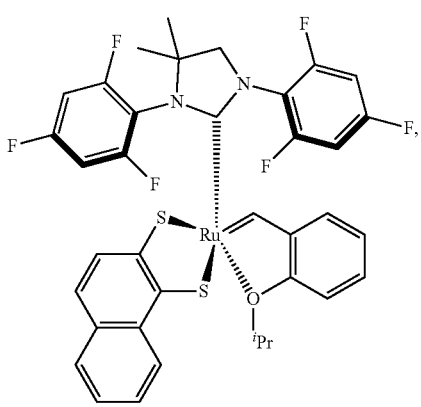 C763
C799

-continued
C849f
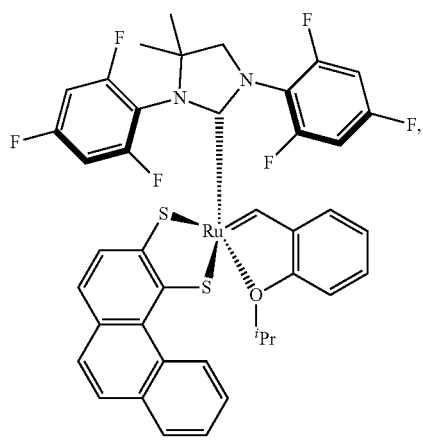
C912
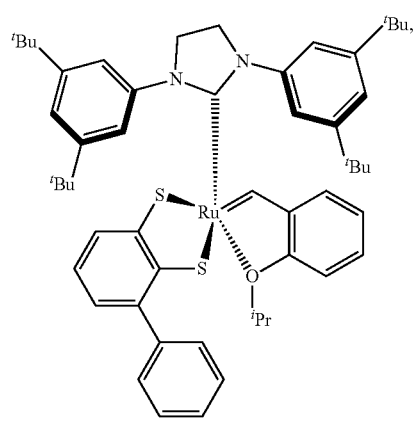
C886
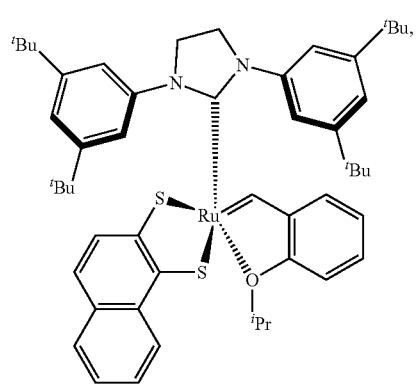
C936
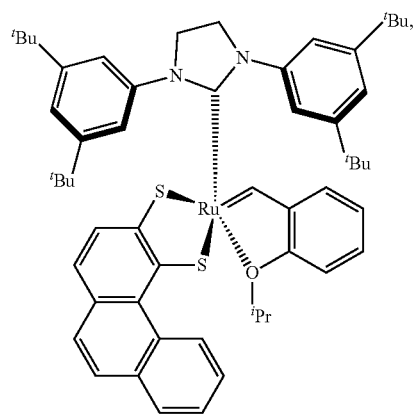
-continued
C857
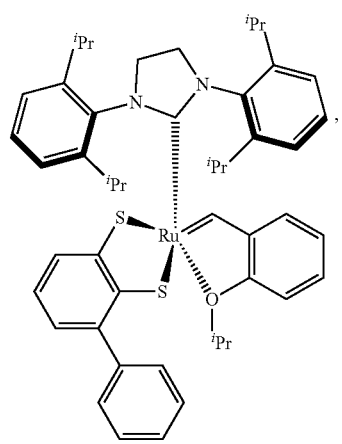
C831c
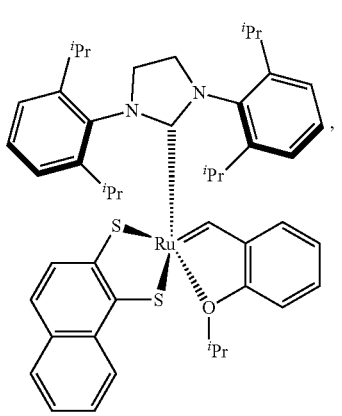
C881
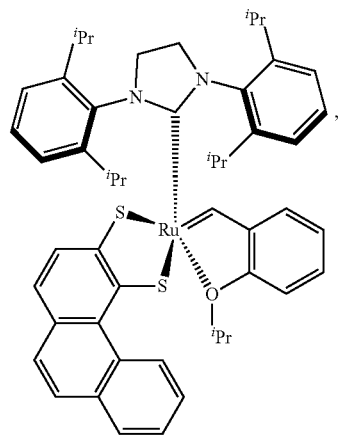

-continued
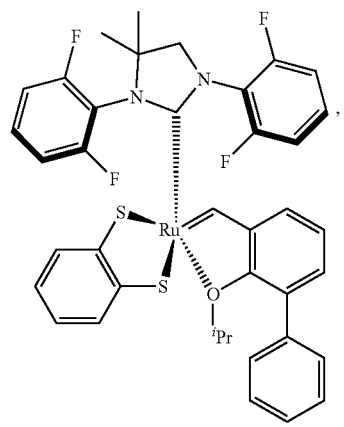
C789
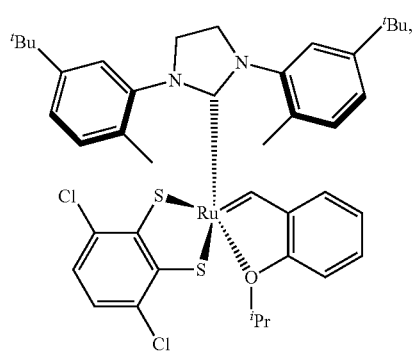
C820
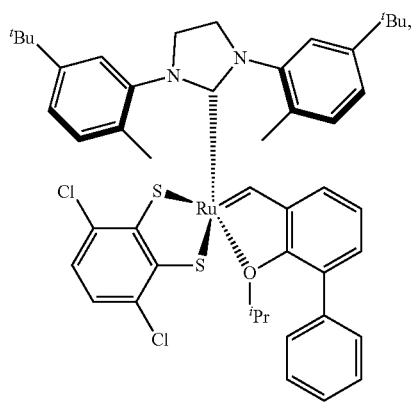
C896z
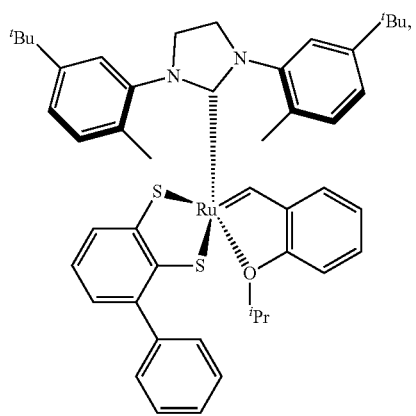
C827z
-continued
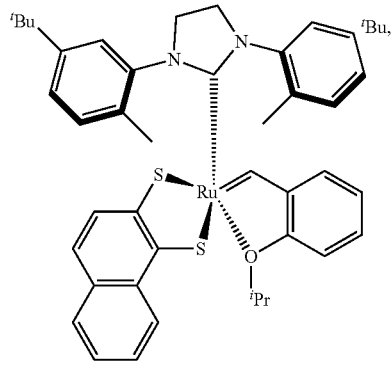
C801z
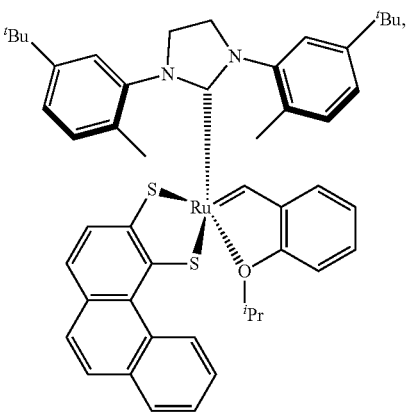
C853
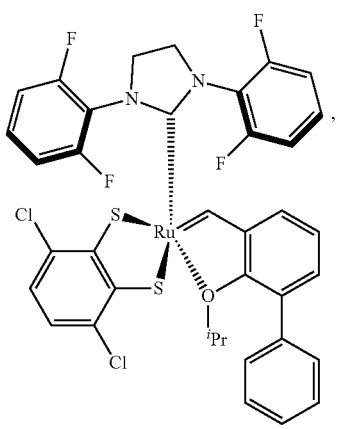
C830
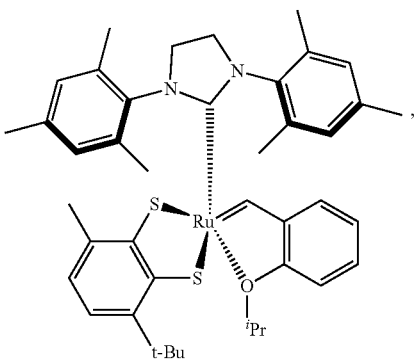
C767

-continued
C761
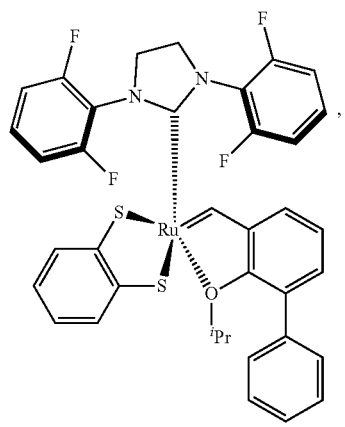
C811
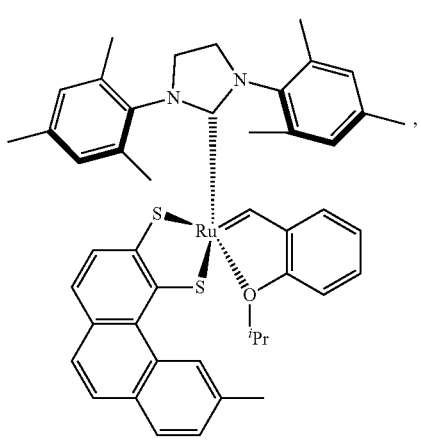
C858
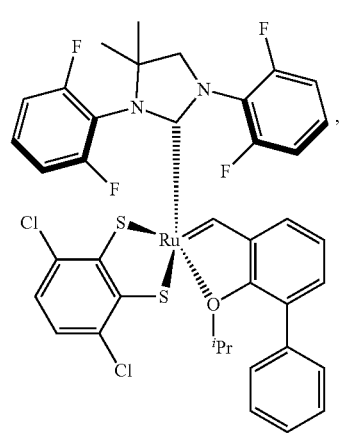
-continued
C897
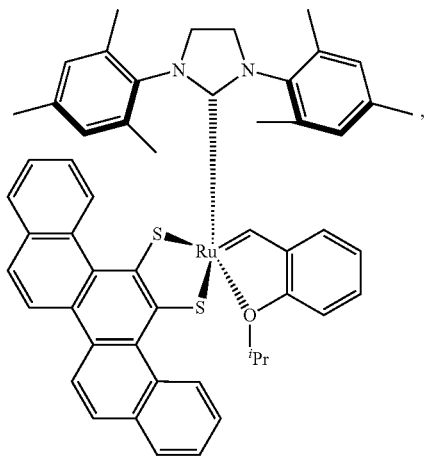
C797
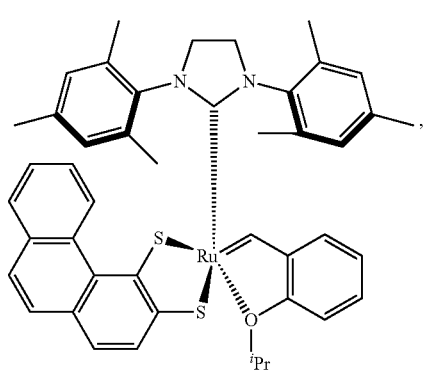
C949
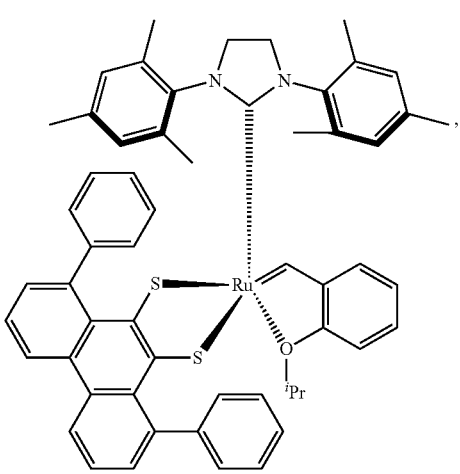

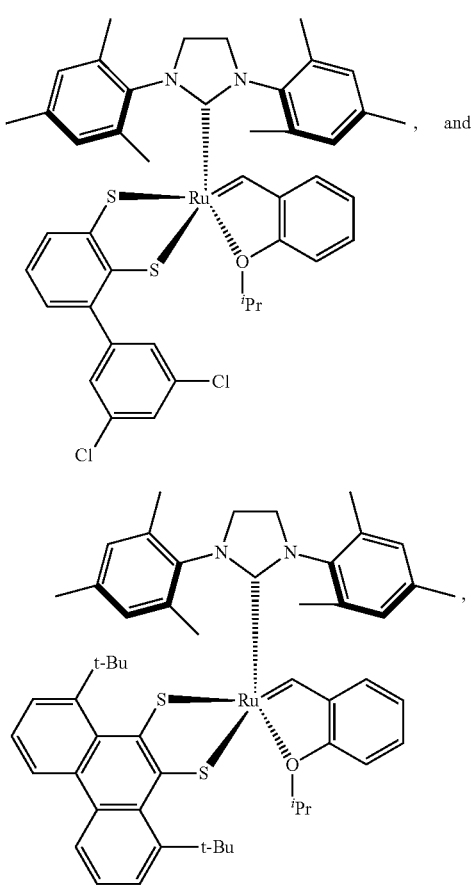

In one embodiment, a compound of Formula (I) is an olefin metathesis catalyst. In one embodiment, a compound of Formula (I) is a Z-selective olefin metathesis catalyst.

In one embodiment, a compound of Formula (I) is an olefin metathesis catalyst. In one embodiment, a compound of Formula (I) is an E-selective olefin metathesis catalyst.

Olefin Reactants

In one embodiment, an olefin reactant comprises a reactant internal olefin, wherein the reactant internal olefin is in a Z-configuration.

In one embodiment, an olefin reactant comprises a reactant internal olefin, wherein the reactant internal olefin is di-substituted and is in a Z-configuration.

In one embodiment, an olefin reactant comprising a reactant internal olefin is represented by the structure of Formula (1):

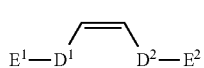

Formula (1)

wherein, $D^1$ and $D^2$ are identical or are independently selected from nil, $CH_2$, O, or S; and $E^1$ and $E^2$ are identical or are independently selected from hydrogen, hydrocarbyl (e.g., $C_1$-$C_{20}$ alkyl, $C_5$-$C_{20}$ aryl, $C_5$-$C_{30}$ aralkyl, or $C_5$-$C_{30}$ alkaryl), substituted hydrocarbyl (e.g., substituted $C_1$-$C_{20}$ alkyl, $C_5$-$C_{20}$ aryl, $C_5$-$C_{30}$ aralkyl, or $C_5$-$C_{30}$ alkaryl), heteroatom-containing hydrocarbyl (e.g., $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl), and substituted heteroatom-containing hydrocarbyl (e.g., substituted $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl) and, if substituted hydrocarbyl or substituted heteroatom-containing hydrocarbyl, wherein the substituents may be functional groups ("Fn") such as halo, hydroxyl, sulfhydryl, $C_1$-$C_{24}$ alkoxy, $C_5$-$C_{24}$ aryloxy, $C_6$-$C_{24}$ aralkyloxy, $C_6$-$C_{24}$ alkaryloxy, acyl (including $C_2$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl (—(CO)—O-alkyl), $C_6$-$C_{24}$ aryloxycarbonyl (—(CO)—O-aryl), halocarbonyl (—(CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO$^-$), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_1$-$C_{24}$ haloalkyl)-substituted carbamoyl (—(CO)—NH($C_1$-$C_{24}$ haloalkyl)), di-($C_1$-$C_{24}$ haloalkyl)-substituted carbamoyl (—(CO)—N($C_1$-$C_{24}$ haloalkyl)$_2$), mono-($C_5$-$C_{24}$ aryl)-substituted carbamoyl (—(CO)—NH-aryl), di-($C_5$-$C_{24}$ aryl)-substituted carbamoyl (—(CO)—N($C_5$-$C_{24}$ aryl)$_2$), di-N—($C_1$-$C_{24}$ alkyl), N—($C_5$-$C_{24}$ aryl)-substituted carbamoyl (—(CO)—N($C_1$-$C_{24}$ alkyl)($C_5$-$C_{24}$ aryl), thiocarbamoyl (—(CS)—NH$_2$), mono-($C_1$-$C_{24}$ alkyl)-substituted thiocarbamoyl (—(CS)—NH($C_1$-$C_{24}$ alkyl)), di-($C_1$-$C_{24}$ alkyl)-substituted thiocarbamoyl (—(CS)—N($C_1$-$C_{24}$ alkyl)$_2$), mono-($C_5$-$C_{24}$ aryl)-substituted thiocarbamoyl (—(CS)—NH-aryl), di-($C_5$-$C_{24}$ aryl)-substituted thiocarbamoyl (—(CS)—N($C_5$-$C_{24}$ aryl)$_2$), di-N—($C_1$-$C_{24}$ alkyl), N—($C_5$-$C_{24}$ aryl)-substituted thiocarbamoyl (—(CS)—N($C_1$-$C_{24}$ alkyl)($C_5$-$C_{24}$ aryl), carbamido (—NH—(CO)—NH$_2$), cyano (—C≡N), cyanato (—O—C≡N), thiocyanato (—S—C≡N), isocyanate (—NisCisO), thioisocyanate (—NisCisS), formyl (—(CO)—H), thioformyl (—(CS)—H), amino (—NH$_2$), mono-($C_1$-$C_{24}$ alkyl)-substituted amino (—NH($C_1$-$C_{24}$ alkyl), di-($C_1$-$C_{24}$ alkyl)-substituted amino (—N($C_1$-$C_{24}$ alkyl)$_2$), mono-($C_5$-$C_{24}$ aryl)-substituted amino (—NH($C_5$-$C_{24}$ aryl), di-($C_5$-$C_{24}$ aryl)-substituted amino (—N($C_5$-$C_{24}$ aryl)$_2$), $C_2$-$C_{24}$ alkylamido (—NH—(CO)-alkyl), $C_6$-$C_{24}$ arylamido (—NH—(CO)-aryl), imino (—CRisNH where R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), $C_2$-$C_{20}$ alkylimino (—CRisN(alkyl), where R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CRisN(aryl), where R includes without limitation hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—NO$_2$), nitroso (—NO), sulfo (—SO$_2$—OH), sulfonato (—SO$_2$—O—), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—SO$_{02}$-alkyl), $C_1$-$C_{24}$ monoalkylaminosulfonyl (—SO$_2$—N(H) alkyl), $C_1$-$C_{24}$ dialkylaminosulfonyl (—SO$_2$—N(alkyl)$_2$), $C_5$-$C_{24}$ arylsulfonyl (—SO$_{02}$-aryl), boryl (—BH$_2$), borono (—B(OH)$_2$), boronato (—B(OR)$_2$ where R is alkyl or aryl), phosphono (—P(O)(OH)$_2$), phosphonato (—P(O)(O—)$_2$), phosphinato (—P(O)(O—)), phospho (—PO$_2$), and phosphino (—PH$_2$); and the hydrocarbyl moieties $C_1$-$C_{24}$ alkyl (preferably $C_1$-$C_{12}$ alkyl, more preferably $C_1$-$C_6$ alkyl), $C_5$-$C_{24}$ aryl (preferably $C_5$-$C_{14}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl), with the proviso that if $E^1$ is hydrogen, then $D^1$ cannot be nil; and where if $E^2$ is hydrogen, then $D^2$ cannot be nil.

In one embodiment, there is a first internal olefin reactant and a second internal olefin reactant, where the first internal olefin reactant and the second internal olefin reactant may be the same or different, wherein the first internal olefin reactant and the second internal olefin reactant are each in a Z-configuration.

In one embodiment, there is a first internal olefin reactant and a second internal olefin reactant, where the first internal olefin reactant and the second internal olefin reactant may be the same or different, wherein the first olefin reactant and the second olefin reactant each comprise a reactant internal olefin.

In one embodiment, there is a first internal olefin reactant and a second internal olefin reactant, where the first internal olefin reactant and the second internal olefin reactant may be the same or different, wherein the first internal olefin reactant and the second internal olefin reactant each comprise a reactant internal olefin, wherein the reactant internal olefin is di-substituted and in a Z-configuration.

In one embodiment, there is a first internal olefin reactant and a second internal olefin reactant, where the first internal olefin reactant is of Formula (1) and the second internal olefin reactant is of Formula (1), wherein the first internal olefin reactant and the second internal olefin reactant may be the same or different.

In one embodiment, an olefin reactant comprises a reactant internal olefin, wherein the reactant internal olefin is in an E-configuration.

In one embodiment, an olefin reactant comprises a reactant internal olefin, wherein the reactant internal olefin is di-substituted and is in an E-configuration.

In one embodiment, an olefin reactant comprising a reactant internal olefin is represented by the structure of Formula (2):

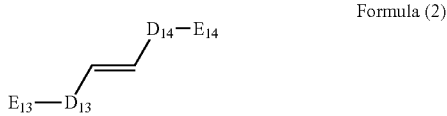

Formula (2)

wherein $D^{13}$ and $D^{14}$ are identical or are independently selected from nil, $CH_2$, O, or S; and $E^{13}$ and $E^{14}$ are identical or are independently selected from hydrogen, hydrocarbyl (e.g., $C_1$-$C_{20}$ alkyl, $C_5$-$C_{20}$ aryl, $C_5$-$C_{30}$ aralkyl, or $C_5$-$C_{30}$ alkaryl), substituted hydrocarbyl (e.g., substituted $C_1$-$C_{20}$ alkyl, $C_5$-$C_{20}$ aryl, $C_5$-$C_{30}$ aralkyl, or $C_5$-$C_{30}$ alkaryl), heteroatom-containing hydrocarbyl (e.g., $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl), and substituted heteroatom-containing hydrocarbyl (e.g., substituted $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl) and, if substituted hydrocarbyl or substituted heteroatom-containing hydrocarbyl, wherein the substituents may be functional groups ("Fn") such as halo, hydroxyl, sulfhydryl, $C_1$-$C_{24}$ alkoxy, $C_5$-$C_{24}$ aryloxy, $C_6$-$C_{24}$ aralkyloxy, $C_6$-$C_{24}$ alkaryloxy, acyl (including $C_2$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl (—(CO)—O-alkyl), $C_6$-$C_{24}$ aryloxycarbonyl (—(CO)—O-aryl), halocarbonyl (—CO)—X where X is halo, $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO$^-$), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_1$-$C_{24}$ haloalkyl)-substituted carbamoyl (—(CO)—NH($C_1$-$C_{24}$ haloalkyl)), di-($C_1$-$C_{24}$ haloalkyl)-substituted carbamoyl (—(CO)—N($C_1$-$C_{24}$ haloalkyl)$_2$), mono-($C_5$-$C_{24}$ aryl)-substituted carbamoyl (—(CO)—NH-aryl), di-($C_5$-$C_{24}$ aryl)-substituted carbamoyl (—(CO)—N($C_5$-$C_{24}$ aryl)$_2$), di-N—($C_1$-$C_{24}$ alkyl), N—($C_5$-$C_{24}$ aryl)-substituted carbamoyl (—(CO)—N($C_1$-$C_{24}$ alkyl)($C_5$-$C_{24}$ aryl), thiocarbamoyl (—(CS)—NH$_2$), mono-($C_1$-$C_{24}$ alkyl)-substituted thiocarbamoyl (—(CS)—NH($C_1$-$C_{24}$ alkyl)), di-($C_1$-$C_{24}$ alkyl)-substituted thiocarbamoyl (—(CS)—N($C_1$-$C_{24}$ alkyl)$_2$), mono-($C_5$-$C_{24}$ aryl)-substituted thiocarbamoyl (—(CS)—NH-aryl), di-($C_5$-$C_{24}$ aryl)-substituted thiocarbamoyl (—(CS)—N($C_5$-$C_{24}$ aryl)$_2$), di-N—($C_1$-$C_{24}$ alkyl), N—($C_5$-$C_{24}$ aryl)-substituted thiocarbamoyl (—(CS)—N($C_1$-$C_{24}$ alkyl)($C_5$-$C_{24}$ aryl), carbamido (—NH—(CO)—NH$_2$), cyano (—C≡N), cyanato (—O—C≡N), thiocyanato (—S—C≡N), isocyanate (—N=C=O), thioisocyanate (—N=C=S), formyl (—(CO)—H), thioformyl (—(CS)—H), amino (—NH$_2$), mono-($C_1$-$C_{24}$ alkyl)-substituted amino (—NH($C_1$-$C_{24}$ alkyl), di-($C_1$-$C_{24}$ alkyl)-substituted amino (—N($C_1$-$C_{24}$ alkyl)$_2$), mono-($C_5$-$C_{24}$ aryl)-substituted amino (—NH($C_5$-$C_{24}$ aryl), di-($C_5$-$C_{24}$ aryl)-substituted amino (—N($C_5$-$C_{24}$ aryl)$_2$), $C_2$-$C_{24}$ alkylamido (—NH—(CO)-alkyl), $C_6$-$C_{24}$ arylamido (—NH—(CO)-aryl), imino (—CR=NH where R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), $C_2$-$C_{20}$ alkylimino (—CR=N(alkyl), where R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CR=N(aryl), where R includes without limitation hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—NO$_2$), nitroso (—NO), sulfo (—SO$_2$—OH), sulfonato (—SO$_2$—O—), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—SO$_2$-alkyl), $C_1$-$C_{24}$ monoalkylaminosulfonyl (—SO$_2$—N(H) alkyl), $C_1$-$C_{24}$ dialkylaminosulfonyl (—SO$_2$—N(alkyl)$_2$), $C_5$-$C_{24}$ arylsulfonyl (—SO$_2$-aryl), boryl (—BH$_2$), borono (—B(OH)$_2$), boronato (—B(OR)$_2$ where R is alkyl or aryl), phosphono (—P(O)(OH)$_2$), phosphonato (—P(O)(O—)$_2$), phosphinato (—P(O)(O—)), phospho (—PO$_2$), and phosphino (—PH$_2$); and the hydrocarbyl moieties $C_1$-$C_{24}$ alkyl (preferably $C_1$-$C_{12}$ alkyl, more preferably $C_1$-$C_6$ alkyl), $C_5$-$C_{24}$ aryl (preferably $C_5$-$C_{14}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl).

In one embodiment, there is a first internal olefin reactant and a second internal olefin reactant, where the first internal olefin reactant and the second internal olefin reactant may be the same or different, wherein the first internal olefin reactant and the second internal olefin reactant are each in an E-configuration.

In one embodiment, there is a first internal olefin reactant and a second internal olefin reactant, where the first internal olefin reactant and the second internal olefin reactant may be the same or different, wherein the first internal olefin reactant and the second internal olefin reactant each comprise a reactant internal olefin, wherein the reactant internal olefin is di-substituted and is in an E-configuration.

In one embodiment, there is a first internal olefin reactant and a second internal olefin reactant, where the first internal olefin reactant is of Formula (2) and the second internal olefin reactant is of Formula (2), wherein the first internal olefin reactant and the second internal olefin reactant may be the same or different.

In general the second olefin reactant comprising a terminal olefin may be represented by the structure of Formula (3):

Formula (3)

wherein $U^\alpha$ is selected from the group comprising nil, $CH_2$, O, or S and $T^\alpha$ is selected from the group consisting of hydrogen, hydrocarbyl (e.g., $C_1$-$C_{20}$ alkyl, $C_5$-$C_{20}$ aryl, $C_5$-$C_{30}$ aralkyl, or $C_5$-$C_{30}$ alkaryl), substituted hydrocarbyl (e.g., substituted $C_1$-$C_{20}$ alkyl, $C_5$-$C_{20}$ aryl, $C_5$-$C_{30}$ aralkyl, or $C_5$-$C_{30}$ alkaryl), heteroatom-containing hydrocarbyl (e.g., $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl), and substituted heteroatom-containing hydrocarbyl (e.g., substituted $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl) and, if substituted hydrocarbyl or substituted heteroatom-containing hydrocarbyl, wherein the substituents may be functional groups ("Fn") such as phosphonato, phosphoryl, phosphanyl, phosphino, sulfonato, $C_1$-$C_{20}$ alkylsulfanyl, $C_5$-$C_{20}$ arylsulfanyl, $C_1$-$C_{20}$ alkylsulfonyl, $C_5$-$C_{20}$ arylsulfonyl, $C_1$-$C_{20}$ alkylsulfinyl, $C_5$-$C_{20}$ arylsulfinyl, sulfonamido, amino, amido, imino, nitro, nitroso, hydroxyl, $C_1$-$C_{20}$ alkoxy, $C_5$-$C_{20}$ aryloxy, $C_2$-$C_{20}$ alkoxycarbonyl, $C_5$-$C_{20}$ aryloxycarbonyl, carboxyl, carboxylato, mercapto, formyl, $C_1$-$C_{20}$ thioester, cyano, cyanato, carbamoyl, epoxy, styrenyl, silyl, silyloxy, silanyl, siloxazanyl, boronato, boryl, or halogen, or a metal-containing or metalloid-containing group (wherein the metal may be, for example, Sn or Ge).

In one embodiment, there is a first internal olefin reactant and a second terminal olefin reactant, wherein the first internal olefin reactant is in an E-configuration.

In one embodiment, there is a first internal olefin reactant and a second terminal olefin reactant, wherein the first internal olefin reactant is in a Z-configuration.

In one embodiment, there is a first internal olefin reactant and a second terminal olefin reactant, where the first internal olefin reactant is of Formula (1) and the second terminal olefin reactant is of Formula (3).

In one embodiment, there is a first internal olefin reactant and a second terminal olefin reactant, where the first internal olefin reactant is of Formula (2) and the second terminal olefin reactant is of Formula (3).

Olefin Products

In one embodiment, the olefin product is at least one cross metathesis product, wherein the at least one cross metathesis product is in a Z-configuration.

In one embodiment, the olefin product is at least one cross metathesis product, wherein the at least one cross metathesis product is di-substituted and is in a Z-configuration.

In one embodiment, an at least one cross metathesis product comprises a product internal olefin, wherein the product internal olefin is in a Z-configuration.

In one embodiment, an at least one cross metathesis product comprises a product internal olefin, wherein the product internal olefin is di-substituted and is in a Z-configuration.

In one embodiment, the olefin product is at least one cross metathesis product, wherein the at least one cross metathesis product is in an E-configuration.

In one embodiment, the olefin product is at least one cross metathesis product, wherein the at least one cross metathesis product is di-substituted and is in an E-configuration.

In one embodiment, an at least one cross metathesis product comprises a product internal olefin, wherein the product internal olefin is in an E-configuration.

In one embodiment, an at least one cross metathesis product comprises a product internal olefin, wherein the product internal olefin is di-substituted and is in an E-configuration.

In some embodiments, the invention provides a method that produces a compound (i.e., a product, olefin product; e.g., cross metathesis product) having a carbon-carbon double bond (e.g., a product internal olefin) in a Z:E ratio greater than about 1:1, greater than about 2:1, greater than about 3:1, greater than about 4:1, greater than about 5:1, greater than about 6:1, greater than about 7:1, greater than about 8:1, greater than about 9:1, greater than about 95:5, greater than about 96:4, greater than about 97:3, greater than about 98:2, or in some cases, greater than about 99:1. In some cases, about 100% of the carbon-carbon double bond produced in the metathesis reaction may have a Z configuration. The Z or cis selectivity may also be expressed as a percentage of product formed (e.g., cross metathesis product). In some cases, the product (e.g., cross metathesis product) may be greater than about 50% Z, greater than about 60% Z, greater than about 70% Z, greater than about 80% Z, greater than about 90% Z, greater than about 95% Z, greater than about 96% Z, greater than about 97% Z, greater than about 98% Z, greater than about 99% Z, or in some cases greater than about 99.5% Z.

In another embodiment, an at least one cross metathesis product comprising a product internal olefin is represented by the structure of Formula (4):

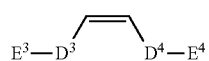

Formula (4)

wherein, $D^3$ and $D^4$ are identical or are independently selected from nil, $CH_2$, O, or S; and $E^3$ and $E^4$ are identical or are independently selected from hydrogen, hydrocarbyl (e.g., $C_1$-$C_{20}$ alkyl, $C_5$-$C_{20}$ aryl, $C_5$-$C_{30}$ aralkyl, or $C_5$-$C_{30}$ alkaryl), substituted hydrocarbyl (e.g., substituted $C_1$-$C_{20}$ alkyl, $C_5$-$C_{20}$ aryl, $C_5$-$C_{30}$ aralkyl, or $C_5$-$C_{30}$ alkaryl), heteroatom-containing hydrocarbyl (e.g., $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl), and substituted heteroatom-containing hydrocarbyl (e.g., substituted $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl) and, if substituted hydrocarbyl or substituted heteroatom-containing hydrocarbyl, wherein the substituents may be functional groups ("Fn") such as halo, hydroxyl, sulfhydryl, $C_1$-$C_{24}$ alkoxy, $C_5$-$C_{24}$ aryloxy, $C_6$-$C_{24}$ aralkyloxy, $C_6$-$C_{24}$ alkaryloxy, acyl (including $C_2$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl (—(CO)—O-alkyl), $C_6$-$C_{24}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO$^-$), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_1$-$C_{24}$ haloalkyl)-substituted carbamoyl (—(CO)—NH($C_1$-$C_{24}$ haloalkyl)), di-($C_1$-$C_{24}$ haloalkyl)-substituted carbamoyl (—(CO)—N($C_1$-$C_{24}$ haloalkyl)$_2$), mono-($C_5$-$C_{24}$ aryl)-substituted carbamoyl (—(CO)—NH-aryl), di-($C_5$-$C_{24}$ aryl)-substituted carbamoyl (—(CO)—N($C_5$-$C_{24}$ aryl)$_2$), di-N—($C_1$-$C_{24}$ alkyl), N—($C_5$-$C_{24}$ aryl)-substituted carbamoyl (—(CO)—N($C_1$-$C_{24}$ alkyl)($C_5$-$C_{24}$ aryl), thiocarbamoyl (—(CS)—NH$_2$), mono-($C_1$-$C_{24}$ alkyl)-substituted thiocarbamoyl (—(CS)—NH($C_1$-$C_{24}$ alkyl)), di-($C_1$-$C_{24}$ alkyl)-substituted thiocarbamoyl (—(CS)—N($C_1$-$C_{24}$ alkyl)$_2$), mono-($C_5$-$C_{24}$ aryl)-substituted thiocarbamoyl (—(CS)—NH-aryl), di-($C_5$-$C_{24}$ aryl)-substituted thiocarbamoyl (—(CS)—N($C_5$-$C_{24}$ aryl)$_2$), di-N—($C_1$-$C_{24}$ alkyl), N—($C_5$-$C_{24}$ aryl)-substituted thiocarbamoyl (—(CS)—N($C_1$-$C_{24}$ alkyl)($C_5$-$C_{24}$ aryl), carbamido (—NH—(CO)—NH$_2$), cyano (—C≡N), cyanato (—O—C—N), thiocyanato (—S—C≡N), isocyanate (—NisCisO), thioisocyanate (—NisCisS), formyl (—(CO)—H), thioformyl (—(CS)—H), amino (—NH$_2$), mono-($C_1$-$C_{24}$ alkyl)-substituted amino (—NH($C_1$-$C_{24}$ alkyl), di-($C_1$-$C_{24}$ alkyl)-substituted amino (—N($C_1$-$C_{24}$ alkyl)$_2$), mono-($C_5$-$C_{24}$ aryl)-substituted amino (—NH($C_5$-$C_{24}$ aryl), di-($C_5$-$C_{24}$ aryl)-substituted amino (—N($C_5$-$C_{24}$ aryl)$_2$), $C_2$-$C_{24}$ alkylamido (—NH—(CO)-alkyl), $C_6$-$C_{24}$ arylamido (—NH—(CO)-aryl), imino (—CRisNH where R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), $C_2$-$C_{20}$ alkylimino (—CRisN (alkyl), where R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CRisN(aryl), where R includes without limitation hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—NO$_2$), nitroso (—NO), sulfo (—SO$_2$—OH), sulfonato (—SO$_2$—O—), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—SO$_2$-alkyl), $C_1$-$C_{24}$ monoalkylaminosulfonyl (—SO$_2$—N(H) alkyl), $C_1$-$C_{24}$ dialkylaminosulfonyl (—SO$_2$—N(alkyl)$_2$), $C_5$-$C_{24}$ arylsulfonyl (—SO$_2$-aryl), boryl (—BH$_2$), borono (—B(OH)$_2$), boronato (—B(OR)$_2$ where R is alkyl or aryl), phosphono (—P(O)(OH)$_2$), phosphonato (—P(O)(O$^-$)$_2$), phosphinato (—P(O)(O—)), phospho (—PO$_2$), and phosphino (—PH$_2$); and the hydrocarbyl moieties $C_1$-$C_{24}$ alkyl (preferably $C_1$-$C_{12}$ alkyl, more preferably $C_1$-$C_6$ alkyl), $C_5$-$C_{24}$ aryl (preferably $C_5$-$C_{14}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl), with the proviso that if $E^3$ is hydrogen, then $D^3$ cannot be nil; and where if $E^4$ is hydrogen, then $D^4$ cannot be nil.

In some embodiments, the invention provides a method that produces a compound (i.e., a product, olefin product; e.g., cross metathesis product) having a carbon-carbon double bond (e.g., a product internal olefin) in an E:Z ratio greater than about 1:1, greater than about 2:1, greater than about 3:1, greater than about 4:1, greater than about 5:1, greater than about 6:1, greater than about 7:1, greater than about 8:1, greater than about 9:1, greater than about 95:5, greater than about 96:4, greater than about 97:3, greater than about 98:2, or in some cases, greater than about 99:1. In some cases, about 100% of the carbon-carbon double bond produced in the metathesis reaction may have an E configuration. The E or trans selectivity may also be expressed as a percentage of product formed (e.g., cross metathesis product). In some cases, the product (e.g., cross metathesis product) may be greater than about 50% E, greater than about 60% E, greater than about 70% E, greater than about 80% E, greater than about 90% E, greater than about 95% E, greater than about 96% E, greater than about 97% E, greater than about 98% E, greater than about 99% E, or in some cases greater than about 99.5% E.

In another example an at least one cross metathesis product comprising a product internal olefin, wherein the product internal olefin is in the E-configuration may be represented by the structure of Formula (5):

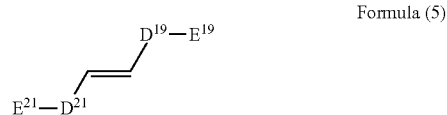

Formula (5)

wherein, $D^{19}$ and $D^{21}$ are identical or are independently selected from nil, CH$_2$, O, or S; and $E^{19}$ and $E^{21}$ are identical or are independently selected from hydrogen, hydrocarbyl (e.g., $C_1$-$C_{20}$ alkyl, $C_5$-$C_{20}$ aryl, $C_5$-$C_{30}$ aralkyl, or $C_5$-$C_{30}$ alkaryl), substituted hydrocarbyl (e.g., substituted $C_1$-$C_{20}$ alkyl, $C_5$-$C_{20}$ aryl, $C_5$-$C_{30}$ aralkyl, or $C_5$-$C_{30}$ alkaryl), heteroatom-containing hydrocarbyl (e.g., $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl), and substituted heteroatom-containing hydrocarbyl (e.g., substituted $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl) and, if substituted hydrocarbyl or substituted heteroatom-containing hydrocarbyl, wherein the substituents may be functional groups ("Fn") such as halo, hydroxyl, sulfhydryl, $C_1$-$C_{24}$ alkoxy, $C_5$-$C_{24}$ aryloxy, $C_6$-$C_{24}$ aralkyloxy, $C_6$-$C_{24}$ alkaryloxy, acyl (including $C_2$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl (—(CO)—O-alkyl), $C_6$-$C_{24}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_1$-$C_{24}$ haloalkyl)-substituted carbamoyl (—(CO)—NH($C_1$-$C_{24}$ haloalkyl)), di-($C_1$-$C_{24}$ haloalkyl)-substituted carbamoyl (—(CO)—N($C_1$-$C_{24}$ haloalkyl)$_2$), mono-($C_5$-$C_{24}$ aryl)-substituted carbamoyl (—(CO)—NH-aryl), di-($C_5$-$C_{24}$ aryl)-substituted carbamoyl (—(CO)—N($C_5$-$C_{24}$ aryl)$_2$), di-N—($C_1$-$C_{24}$ alkyl), N—($C_5$-$C_{24}$ aryl)-substituted carbamoyl (—(CO)—N(C$_1$-C$_{24}$ alkyl)(C$_5$-C$_{24}$ aryl), thiocarbamoyl (—(CS)—NH$_2$), mono-(C$_1$-C$_{24}$ alkyl)-substituted thiocarbamoyl (—(CS)—NH(C$_1$-C$_{24}$ alkyl)), di-(C$_1$-C$_{24}$ alkyl)-substituted thiocarbamoyl (—(CS)—N(C$_1$-C$_{24}$ alkyl)$_2$), mono-(C$_5$-C$_{24}$ aryl)-substituted thiocarbamoyl (—(CS)—NH-aryl), di-(C$_5$-C$_{24}$ aryl)-substituted thiocarbamoyl (—(CS)—N(C$_5$-C$_{24}$ aryl)$_2$), di-N—(C$_1$-C$_{24}$ alkyl), N—(C$_5$-C$_{24}$ aryl)-substituted thiocarbamoyl (—(CS)—N(C$_1$-C$_{24}$ alkyl)(C$_5$-C$_{24}$ aryl), carbamido (—NH—(CO)—NH$_2$), cyano (—C≡N), cyanato (—O—C≡N), thiocyanato (—S—C≡N), isocyanate (—N=C=O), thioisocyanate (—N=C=S), formyl (—(CO)—H), thioformyl (—(CS)—H), amino (—NH$_2$), mono-(C$_1$-C$_{24}$ alkyl)-substituted amino (—NH(C$_1$-C$_{24}$ alkyl), di-(C$_1$-C$_{24}$ alkyl)-substituted amino (—N(C$_1$-C$_{24}$ alkyl)$_2$), mono-(C$_5$-C$_{24}$ aryl)-substituted amino (—NH(C$_5$-C$_{24}$ aryl), di-(C$_5$-C$_{24}$ aryl)-substituted amino (—N(C$_5$-C$_{24}$ aryl)$_2$), C$_2$-C$_{24}$ alkylamido (—NH—(CO)-alkyl), C$_6$-C$_{24}$ arylamido (—NH—(CO)-aryl), imino (—CR=NH where R includes without limitation hydrogen, C$_1$-C$_{24}$ alkyl, C$_5$-C$_{24}$ aryl, C$_6$-C$_{24}$ alkaryl, C$_6$-C$_{24}$ aralkyl, etc.), C$_2$-C$_{20}$ alkylimino (—CR=N(alkyl), where R includes without limitation hydrogen, C$_1$-C$_{24}$ alkyl, C$_5$-C$_{24}$ aryl, C$_6$-C$_{24}$ alkaryl, C$_6$-C$_{24}$ aralkyl, etc.), arylimino (—CR=N(aryl), where R includes without limitation hydrogen, C$_1$-C$_{20}$ alkyl, C$_5$-C$_{24}$ aryl, C$_6$-C$_{24}$ alkaryl, C$_6$-C$_{24}$ aralkyl, etc.), nitro (—NO$_2$), nitroso (—NO), sulfo (—SO$_2$—OH), sulfonato (—SO$_2$—O), C$_1$-C$_{24}$ alkylsulfanyl (—S-alkyl; also termed "alkylthio"), C$_5$-C$_{24}$ arylsulfanyl (—S-aryl; also termed "arylthio"), C$_1$-C$_{24}$ alkylsulfinyl (—(SO)-alkyl), C$_5$-C$_{24}$ arylsulfinyl (—(SO)-aryl), C$_1$-C$_{24}$ alkylsulfonyl (—SO$_2$-alkyl), C$_1$-C$_{24}$ monoalkylaminosulfonyl (—SO$_2$—N(H) alkyl), C$_1$-C$_{24}$ dialkylaminosulfonyl (—SO$_2$—N(alkyl)$_2$), C$_5$-C$_{24}$ arylsulfonyl (—SO$_2$-aryl), boryl (—BH$_2$), borono (—B(OH)$_2$), boronato (—B(OR)$_2$ where R is alkyl or aryl), phosphono (—P(O)(OH)$_2$), phosphonato (—P(O)(O)$_2$), phosphinato (—P(O)(O)), phospho (—PO$_2$), and phosphino (—PH$_2$); and the hydrocarbyl moieties C$_1$-C$_{24}$ alkyl (preferably C$_1$-C$_{12}$ alkyl, more preferably C$_1$-C$_6$ alkyl), C$_5$-C$_{24}$ aryl (preferably C$_5$-C$_{14}$ aryl), C$_6$-C$_{24}$ alkaryl (preferably C$_6$-C$_{16}$ alkaryl), and C$_6$-C$_{24}$ aralkyl (preferably C$_6$-C$_{16}$ aralkyl); with the proviso that if E$^{21}$ is hydrogen, then D$^{21}$ cannot be nil; and where if E$^{19}$ is hydrogen, then D$^{19}$ cannot be nil.

EXPERIMENTAL

In the following examples, efforts have been made to ensure accuracy with respect to numbers used (e.g., amounts, temperature, etc.) but some experimental error and deviation should be accounted for. Unless indicated otherwise, temperature is in degrees Celsius and pressure is at or near atmospheric. The examples are to be considered as not being limiting of the invention as described herein and are instead provided as representative examples of the catalyst compounds of the invention, of the methods that may be used in their preparation, and of the methods of using the inventive catalysts.

All manipulations were carried out under an inert atmosphere using an argon-filled glovebox or standard Schlenk techniques. All glassware was oven dried prior to use. All solvents were anhydrous grade and sparged with argon before use. All reagents, unless specified, were obtained from commercial sources and used without further purification. Other reagents, including catalysts C711, C767, C643, C627 and C823 were prepared according to previously reported literature procedures. Trans-methyl-9-octadecenoate (>97%) and Cis-methyl-9-octadecenoate (>99%) were purchased from TCI.

$^1$HNMR spectra were obtained at 400 MHz respectively. [1]H were recorded relative to residual protio-solvent.

GC Methods: Volatile products were analyzed using an Agilent 6850 gas chromatography (GC) instrument with a flame ionization detector (FID). The following conditions and equipment were used:

Method 1: Column: DB-225, 30 m×0.25 mm (ID)×0.25 μm film thickness.

Manufacturer: Agilent

GC and column conditions: Injector temperature: 220° C., Detector temperature: 220° C.

Oven temperature: Starting temperature: 35° C., hold time: 0.5 minutes.

Ramp rate 10° C./min to 130° C., hold time: 0 minutes.

Ramp rate 20° C./min to 220° C., hold time: 5 minutes.

Carrier gas: Helium

Mean gas velocity: 25 cm/sec

Split ratio: 20:1

Method 2: Column: HP-5, 30 m×0.25 mm (ID)×0.25 μm film thickness.

Manufacturer: Agilent

GC and column conditions: Injector temperature: 250° C., Detector temperature: 280° C.

Oven temperature: Starting temperature: 100° C., hold time: 1 minute

Ramp rate 10° C./min to 270° C., hold time: 12 minutes.

Carrier gas: Helium

Average velocity: 30 cm/sec

Split ratio: 40.8:1

The following abbreviations are used herein:

| | |
|---|---|
| RT or r.t. | room temperature |
| mL | milliliter |
| μL | microliter |
| CD$_2$Cl$_2$ | deuterated dichloromethane |
| ° C. | degrees Celsius |
| h | hour |
| g | gram |
| mg | milligram |
| THF | tetrahydrofuran |
| THF-d$_8$ | deuterated tetrahydrofuran |
| DMSO-d$_6$ | deuterated dimethylsulfoxide |
| iPr | isopropyl (—CH(CH$_3$)$_2$) |
| Zn(OAc)$_2$ • 2 H$_2$O | zinc acetate dehydrate |
| HC(OEt)$_3$ | triethyl orthoformate |
| HCl | hydrochloric acid |
| PhCl | chlorobenzene |
| NaBF$_4$ | sodium tetrafluoroborate |
| NaOtBu | sodium tert-butoxide |
| NaOH | sodium hydride |
| LiAlH$_4$ | lithium aluminum hydride |
| KHMDS | potassium bis(trimethylsilyl)amide |
| 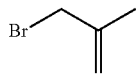 | 3-bromo-2-methylpropene |

Example 1

Preparation of (3,6-dichlorobenzene-1,2-dithiolato)(ethylenediamine)zinc(II)

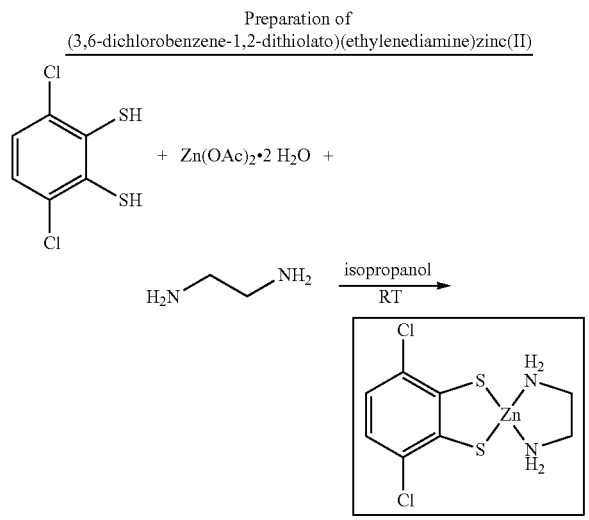

To a 250 mL round bottom flask equipped with a magnetic stir bar was added 3,6-dichlorobenzene-1,2-dithiol (2.00 g, 9.47 mmol), Zn(OAc)$_2$·2H$_2$O (8.32 g, 37.9 mmol), ethylenediamine (3.80 mL, 56.8 mmol), and isopropanol (100 mL). The resulting suspension was rapidly stirred for 24 h at room temperature. The resulting precipitate was isolated by filtration, washed with methanol (50 mL), hot chloroform (50 mL), then dried under vacuum overnight affording (3,6-dichlorobenzene-1,2-dithiolato)(ethylenediamine)zinc (II) as an light yellow solid (2.78 g, 87.9%).

$^1$H NMR (400 MHz, DMSO-d$_6$) δ 6.78 (br s, 2H), 4.06 (br s, 4H), 2.65 (br s, 4H).

Example 2

General procedure for the preparation of a Compound of Formula (I): C849z

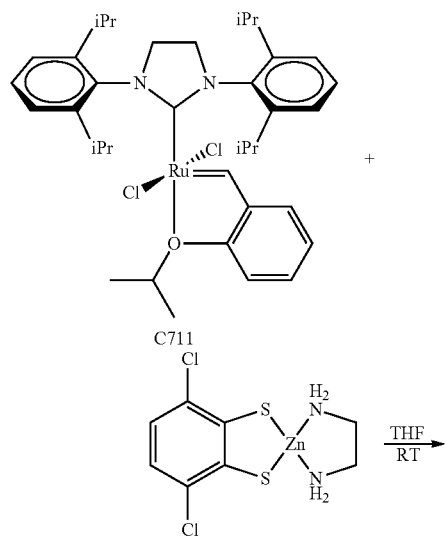

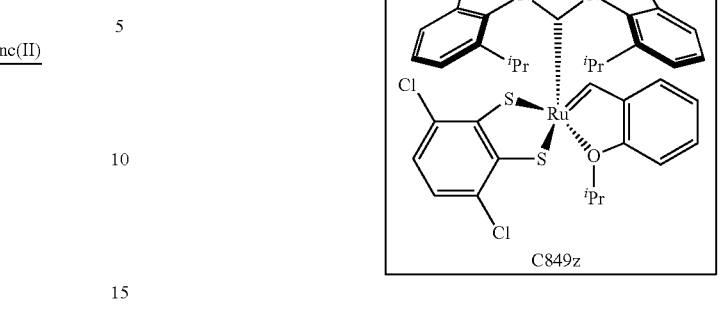

In an argon filled glovebox, a 40 mL scintillation vial equipped with a magnetic stir bar was charged with C711 (0.500 g, 0.703 mmol), (3,6-dichlorobenzene-1,2-dithiolato)(ethylenediamine)zinc(II) (259 mg, 0.774 mmol), and 15 mL THF. The resulting suspension was stirred for 6 h at room temperature then devolatilized. The resulting residue was dissolved in a minimal amount of dichloromethane, filtered through a pad of celite, recrystallized from dichloromethane/diethyl ether at −30° C. The red/brown crystals were isolated by filtration and dried under vacuum to afford C849z (462 mg, 77.4%).

$^1$H NMR (400 MHz, CD$_2$Cl$_2$) δ 14.52 (s, 1H), 7.52-7.34 (m, 4H), 7.31 (d, J=6.8 Hz, 1H), 7.20 (d, J=6.4 Hz, 1H), 6.86-6.97 (m, 2H), 6.82 (t, J i=7.3 Hz, 2H), 6.74 (d, J=7.0 Hz, 1H), 6.55 (d, J=6.3 Hz, 1H), 4.97 (hept, J=5.6 Hz, 1H), 4.36 (dd, J=20.2, 10.5 Hz, 1H), 4.18 (dd, J=19.1, 9.4 Hz, 1H), 4.02 (dd, J=17.6, 9.5 Hz, 1H), 3.96-3.80 (m, 3H), 3.21-2.99 (m, 1H), 2.54-2.34 (m, 1H), 1.91 (d, J=5.5 Hz, 3H), 1.43 (d, J=5.8 Hz, 3H), 1.38 (d, J=5.9 Hz, 3H), 1.20-1.35 (m, 6H), 1.00-1.10 (m, 6H), 0.94 (d, J=5.9 Hz, 3H), 0.54 (d, J=5.6 Hz, 3H), 0.04 (d, J=5.4 Hz, 3H).

Example 3

Preparation of C905

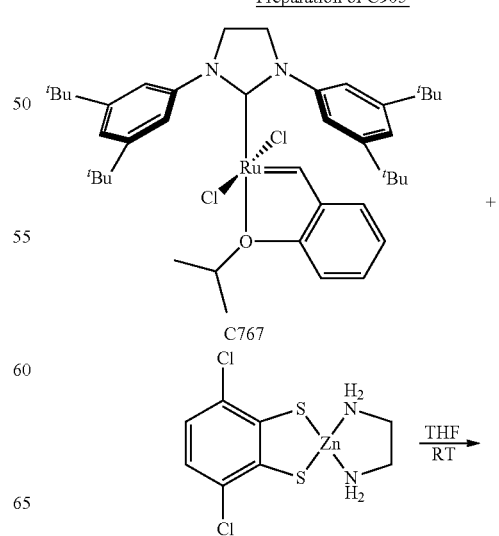

-continued

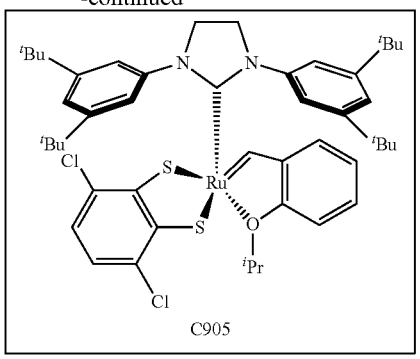

C905

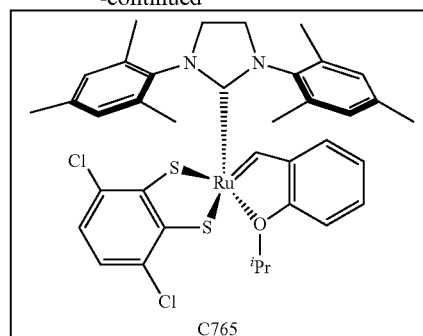

C765

In an argon filled glovebox, a 40 mL scintillation vial equipped with a magnetic stir bar was charged with C767 (0.150 g, 0.196 mmol), (3,6-dichlorobenzene-1,2-dithiolato)(ethylenediamine)zinc(II) (0.072 g, 0.22 mmol), and tetrahydrofuran (10 mL). The resulting suspension was stirred for 1 hour at ambient temperature then devolatilized. The residue was dissolved in dichloromethane (10 mL), filtered through a pad of celite, diluted with hexanes (10 mL) then concentrated under vacuum. Reducing the volume to ~5 mL afforded a yellow/brown microcrystalline solid which was isolated by filtration, washed with cold hexanes (2×3 mL) and dried under vacuum to afford C905 (0.142 g, 80.4%).

$^1$H NMR (400 MHz, CD$_2$Cl$_2$) δ 14.39 (s, 1H), 7.66 (br s, 1H), 7.55 (d, J=1.7 Hz, 2H), 7.44 (t, J=1.8 Hz, 1H), 7.38-7.30 (m, 2H), 6.96 (d, J=8.7 Hz, 1H), 6.94 (d, J=8.1 Hz, 1H), 6.86 (d, J=8.1 Hz, 1H), 6.76 (t, J=7.4 Hz, 1H), 6.56 (dd, J=7.5, 1.5 Hz, 1H), 6.26 (br s, 1H), 5.05 (septet, J=6.3 Hz, 1H), 4.49-4.38 (m, 1H), 4.08-3.97 (m, 3H), 1.59 (br s, 9H), 1.28 (d, J=6.2 Hz, 3H), 1.15 (s, 18H), 1.06 (br s, 9H), 1.02 (d, J=6.4 Hz, 3H).

Example 4

Preparation of C765

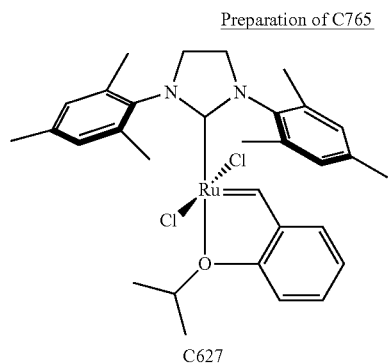

C627

C765 was synthesized according to the procedure described in US 2014/0371454. C765 was isolated as red/brown crystals in 97.1% yield.

Example 5

Preparation of N$^1$,N$^2$-bis(2-fluoro-6-methylphenyl)oxalamide

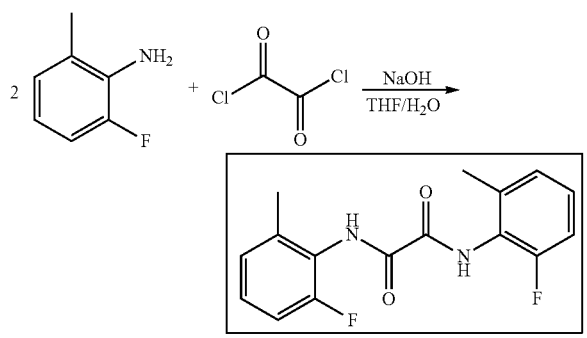

To a 500 mL round bottom flask equipped with a magnetic stir bar was added 2-methyl-6-fluoroaniline (15.0 mL, 130 mmol), tetrahydrofuran/water (1:1, 200 mL), NaOH (5.19 g, 130 mmol), and triethylamine (0.90 mL, 6.5 mmol). The suspension was stirred vigorously at 0° C. and oxalyl chloride (6.58 mL, 77.8 mmol) was added dropwise. After complete addition, the reaction was stirred for 1 hour while warming to ambient temperature. The resulting solid was isolated by filtration, washed with 1M HCl (50 mL), water (3×50 mL), and diethyl ether (2×50 mL) then dried under vacuum to afford N$^1$,N$^2$-bis(2-fluoro-6-methylphenyl)oxalamide (7.05 g, 35.7% yield). $^1$H NMR (400 MHz, DMSO-d$_6$) δ 10.52 (s, 1H), 7.32-7.24 (m, 2H), 7.19-7.11 (m, 4H), 2.24 (s, 6H).

Example 6

Preparation of 1,3-bis(2-fluoro-6-methylphenyl)-4,5-dihydro-1H-imidazol-3-ium-chloride

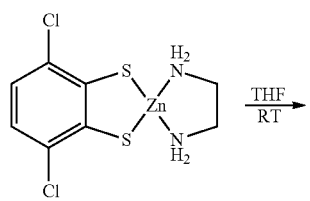

1. LiAlH$_4$, THF/toluene, 50° C., 12 h
2. HCl
3. CH(OEt)$_3$, 130° C., 1 h

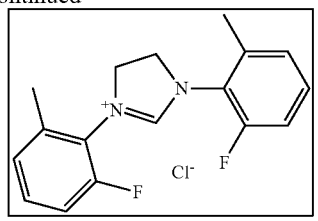

In an argon filled glovebox, lithium aluminum hydride (3.74 g, 98.6 mmol) and tetrahydrofuran/toluene (1:1, 100 mL) were combined in a 500 mL round bottom flask equipped with a magnetic stir bar. $N^1,N^2$-bis(2-fluoro-6-methylphenyl)oxalamide (6.00 g, 19.7 mmol) was subsequently added to the suspension in small portions with stirring. The reaction vessel was sealed, removed from the glovebox, fitted with a reflux condenser and heated to 50° C. under argon for 12 h. After cooling to ambient temperature the reaction was quenched by slowly adding water (3.8 mL), followed by aqueous sodium hydroxide (15 wt %, 3.8 mL), then an additional portion of water (11.4 mL). The reaction was stirred rapidly for 2 hours then decanted away from solid residues and dried over magnesium sulfate. Filtration through a pad of celite afforded a clear solution which was combined with hydrochloric acid (2.0 M in ether, 30 mL, 60 mmol). The resulting precipitate was isolated by filtration then combined with triethyl orthoformate (30 mL) and heated to 130° C. for 1 hour. After cooling the reaction to ambient temperature, the precipitate was isolated by filtration, washed with diethyl ether (2×25 mL), hexanes (2×50 mL), then dried under vacuum to afford 1,3-bis(2-fluoro-6-methylphenyl)-4,5-dihydro-1H-imidazol-3-ium chloride (4.56 g, 71.7% yield).

$^1$H NMR (400 MHz, DMSO-d$_6$) δ 9.63 (s, 1H), 7.55-7.47 (m, 2H), 7.38 (t, J=9.2 Hz, 2H), 7.31 (d, J=7.8 Hz, 2H), 4.57 (s, 4H), 2.48 (s, 6H).

Example 7

Preparation of C829

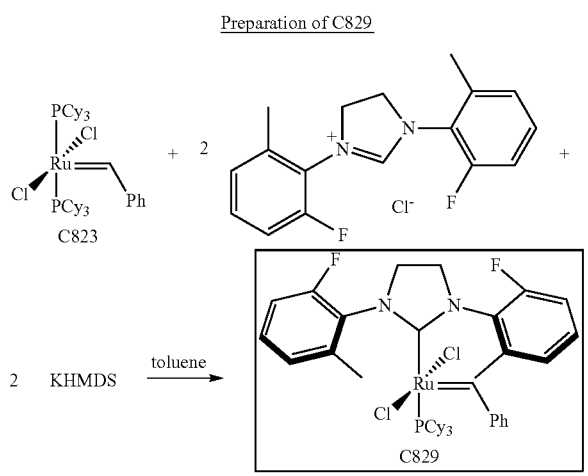

In an argon filled glovebox, C823 (0.676 g, 0.822 mmol), 1,3-bis(2-fluoro-6-methylphenyl)-4,5-dihydro-1H-imidazol-3-ium chloride (0.500 g, 1.64 mmol) and toluene (50 mL) were combined in a 250 mL round bottom flask equipped with a magnetic stir bar. A solution of potassium bis(trimethylsilyl)amide (0.328 g, 1.64 mmol) in toluene (20 mL) was subsequently added and the solution stirred at ambient temperature for 2 hours. All volatiles were subsequently removed in vacuum. The resulting residue was dissolved in dichloromethane (10 mL), filtered through a pad of celite, and devolatilized. The crude product was triturated with hexanes (2×20 mL) then recrystallized from toluene/hexanes at ambient temperature. The crystalline complex was isolated by filtration and dried under vacuum to afford C829 (0.454 g, 66.7% yield).

$^1$H NMR (400 MHz, CD$_2$Cl$_2$) δ 19.28 (s, 1H), 9.4-8.0 (br s 1H), 7.41-7.30 (m, 2H). 7.20 (d, J=7.6 Hz, 1H), 7.16-7.04 (m, 3H), 6.90-5.80 (br s, 3H), 6.72-6.62 (m, 1H), 4.22-3.75 (m, 4H), 2.75 (pseudo d, J=16.5 Hz, 3H), 2.55-2.05 (br s, 3H), 2.11 (pseudo dd, J=22.7, 11.9 Hz, 3H), 1.65-1.23 (m, 15H), 1.10-0.72 (m, 15H)

Example 8

Preparation of C745

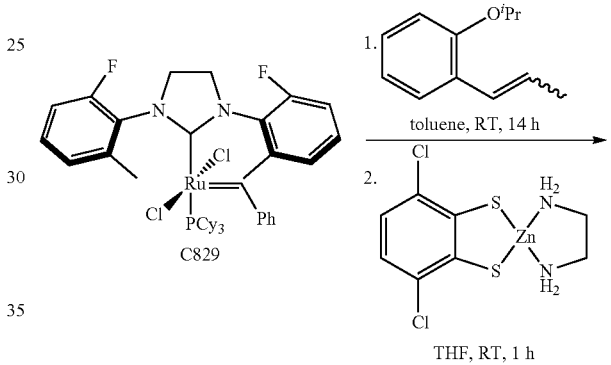

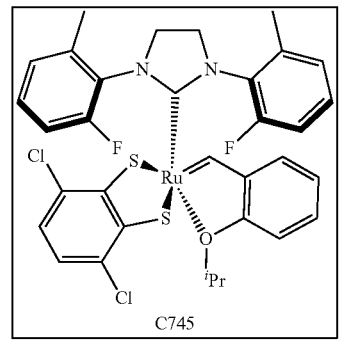

In an argon filled glovebox, C829 (0.300 g, 0.362 mmol), 1-isopropoxy-2-(prop-1-en-1-yl)benzene (0.638 g, 3.62 mmol) and toluene (10 mL) were combined in a 40 mL scintillation vial equipped with a magnetic stir bar. The reaction was stirred at ambient temperature for 14 hours then directly adsorbed onto silica gel. Purification by column chromatography (silica gel, 2 to 6% gradient of ethyl acetate/hexanes) afforded 0.190 g (90% pure) of crude intermediate. The crude intermediate was subsequently combined with (3,6-dichlorobenzene-1,2-dithiolato)(ethylenediamine)zinc(II) (0.115 g, 0.345 mmol) and tetrahydrofuran (5 mL) in a 20 mL scintillation vial equipped with a magnetic stir bar. After 4 hours of stirring at ambient temperature, all volatiles were removed, the residue dissolved in dichloromethane, filtered through celite, devolatilized and recrystallized from dichloromethane/diethyl ether at −35° C. The resulting yellow/brown crystals were isolated by filtration, washed with cold diethyl ether (2×5 mL) then dried under vacuum to afford C745 (0.116 g, 35.7% yield).

$^1$H NMR (400 MHz, CD$_2$Cl$_2$) [three conformers in solution, 8:25:67] δ 14.42 (s, 0.08H), 14.39 (s, 0.25H), 14.36 (s, 0.67H), 7.37-7.27 (m, 1H), 7.26-7.02 (m, 2.7H), 7.02-6.62 (m, 7.3H), 6.41 (s, 0.4H), 6.10 (t, J=9.0 Hz, 0.6H), 5.47-5.38 (m, 1H), 4.13-3.86 (m, 4H), 2.61-2.40 (m, 5H), 1.85-1.65 (m, 7H).

Example 9

Preparation of N,N'-bis(2,6-difluorophenyl)formimidamide

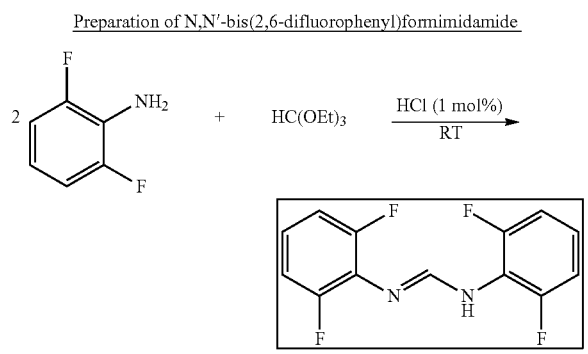

To a 100 mL round bottom flask equipped with a magnetic stir bar was added 2,6-difluoroaniline (10.0 mL, 95.9 mmol) and triethyl orthoformate (8.11 mL, 48.8 mmol). To the stirring solution was added hydrochloric acid (0.040 mL, 12 M, 0.48 mmol) and the reaction stirred at ambient temperature for 10 minutes. The reaction solidified and was subsequently sonicated for an additional 10 minutes. The resulting precipitate was subsequently isolated by filtration, washed with hexanes (2×30 mL) then dried under vacuum to afford N,N'-bis(2,6-difluorophenyl)formimidamide (8.47 g, 67.9% yield).

$^1$H NMR (400 MHz, DMSO-d$_6$) δ 9.47 (br s, 1H), 8.03 (s, 1H), 7.10 (br s, 6H).

Example 10

Preparation of 1,3-bis(2,6-difluorophenyl)-4,4-dimethyl-4,5-dihydro-1H-imidazol-3-ium tetrafluoroborate

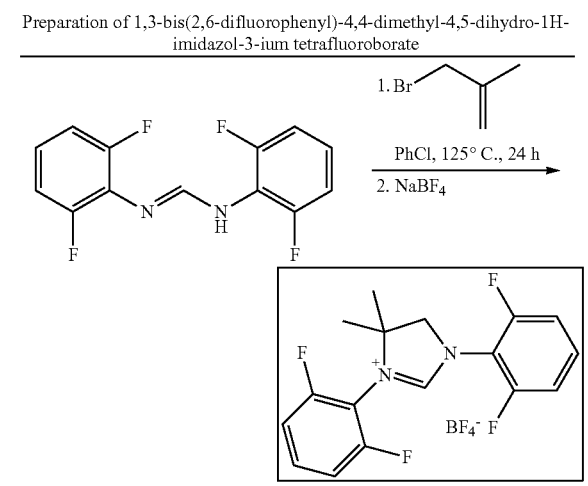

To a 20 mL scintillation vial equipped with a magnetic stir bar was added N,N'-bis(2,6-difluorophenyl)formimidamide (4.00 g, 14.9 mmol), 3-bromo-2-methylpropene (1.65 mL, 16.4 mmol), and chlorobenzene (120 mL). The reaction was heated to 125° C. for 24 h. After cooling the resulting precipitate was isolated by filtration and washed with diethyl ether (2×20 mL). The crude product was then partitioned between dichloromethane and an aqueous sodium tetrafluoroborate solution (100 mL, 1:1, 2.0 g NaBF$_4$/50 mL). The organic layer was separated, dried over magnesium sulfate, filtered through celite and all volatiles were removed by rotary evaporation. The resulting reside was recrystallized from dichloromethane/diethyl ether to afford 1,3-bis(2,6-difluorophenyl)-4,4-dimethyl-4,5-dihydro-1H-imidazol-3-ium tetrafluoroborate (3.25 g, 53.1% yield).

$^1$H NMR (400 MHz, DMSO-d$_6$) δ 9.59 (s, 1H), 7.79 (m, 1H), 7.70-7.60 (m, 1H), 7.55-7.42 (m, 4H), 4.55 (s, 2H), 1.54 (s, 6H).

Example 11

Preparation of C642

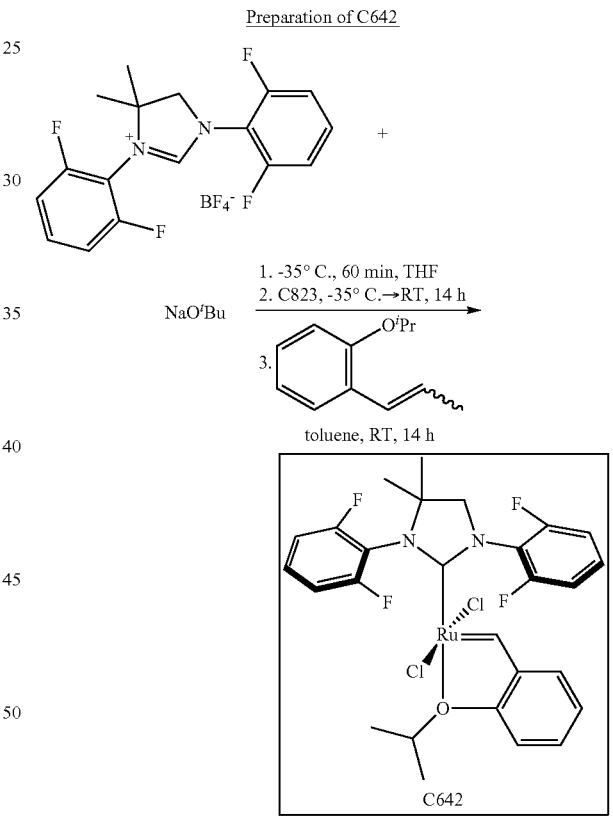

In an argon filled glovebox, 1,3-bis(2,6-difluorophenyl)-4,4-dimethyl-4,5-dihydro-1H-imidazol-3-ium tetrafluoroborate (0.500 g, 1.22 mmol), NaOtBu (0.117 g, 1.22 mmol), and C823 (0.502 g, 0.610 mmol) were weighed into separate 40 mL scintillation vials equipped with magnetic stir bars and each dissolved/suspended in tetrahydrofuran (10 mL). The solutions/suspensions were cooled to −35° C. then the solution of NaOtBu was added to the solution of 1,3-bis(2,6-difluorophenyl)-4,4-dimethyl-4,5-dihydro-1H-imidazol-3-ium tetrafluoroborate over 2 minutes. The reaction was stirred at −35° C. for 1 h then combined with the chilled suspension of C823 and stirred for an additional hour at −35° C. before allowing the reaction to slowly warm to ambient temperature overnight. The reaction was subsequently devolatilized, triturated with hexanes (2×40 mL), dissolved in toluene (10 mL), and filtered through celite. The crude solution was combined with a solution of 1-isopropoxy-2-(prop-1-en-1-yl)benzene (0.400 g, 2.27 mmol) in toluene (2 mL) and stirred overnight at ambient temperature. The resulting green precipitate was isolated by filtration, washed with toluene/hexanes (1:3, 2×10 mL) then dried under vacuum to afford C642 (0.221 g, 56.4% yield).

$^1$H NMR (400 MHz, CD$_2$Cl$_2$) δ 16.76 (s, 1H), 7.59-7.54 (m, 1H), 7.53-7.41 (m, 2H), 7.17-7.07 (m, 5H), 6.98-6.90 (m, 2H), 5.07-4.96 (sept, J=6.2 Hz, 1H), 4.06 (s, 2H), 1.49 (s, 3H), 1.48 (s, 3H), 1.42 (d, J=6.1 Hz, 6H).

Example 12

Preparation of C781

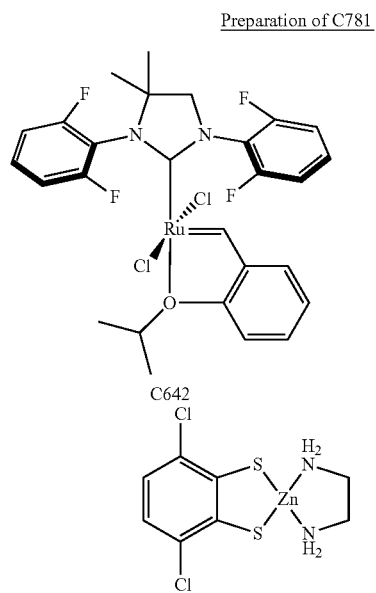

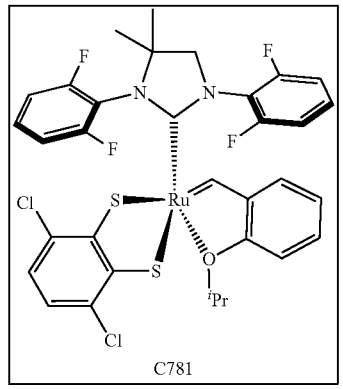

In an argon filled glovebox, C642 (0.150 g, 0.234 mmol) and (3,6-dichlorobenzene-1,2-dithiolato)(ethylenediamine)zinc(II) (0.086 g, 0.26 mmol) were combined in a 20 mL scintillation vial equipped with a magnetic stir bar and dissolved in tetrahydrofuran (10 mL). The reaction was stirred for 60 minutes then devolatilized, dissolved in dichloromethane, filtered, and recrystallized from dichloromethane/diethyl ether at −35° C. The resulting yellow/brown crystals were washed with cold diethyl ether (2×3 mL) then dried under vacuum to afford C781 (0.128 g, 70.2% yield). $^1$H NMR (400 MHz, CD$_2$Cl$_2$) [two conformers in solution, 40:60] δ 14.52 br s (0.4H), 14.43 (br s, 0.6H), 7.33 (t, J=7.4 Hz, 1H), 7.08 (d, J=8.4 Hz, 1H), 7.05-6.67 (m, 9H), 6.13 (br s, 1H), 5.42 (br s, 1H), 3.94 (br q, J=8.0 Hz, 1.2H), 3.78 (br s, 0.8H), 1.88-1.74 (m, 6H), 1.50-1.28 (m, 6H).

Example 13

Preparation of N,N'-bis(2,4,6-trifluorophenyl)formimidamide

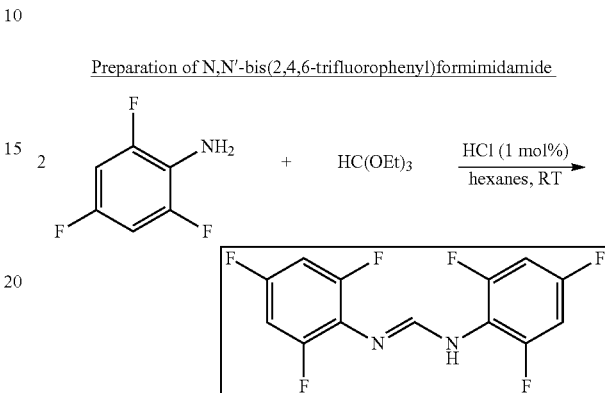

To a 100 mL round bottom flask equipped with a magnetic stir bar was added 2,4,6-difluoroaniline (10.0 g, 68.0 mmol), hexanes (25 mL), and triethyl orthoformate (5.94 mL, 35.7 mmol). To the stirring solution was added hydrochloric acid (0.180 mL, 2 M in diethyl ether, 0.36 mmol) and the reaction stirred at ambient temperature for 60 minutes. The resulting precipitate was subsequently isolated by filtration, washed with hexanes (2×10 mL) then dried under vacuum to afford N,N-bis(2,4,6-difluorophenyl)formimidamide (7.73 g, 74.8% yield).

$^1$H NMR (400 MHz, DMSO-d$_6$) δ 9.27 (br s, 1H), 7.98 (s, 1H), 7.19 (br s, 4H).

Example 14

Preparation of 1,3-bis(2,4,6-difluorophenyl)-4,4-dimethyl-4,5-dihydro-1H-imidazol-3-ium tetrafluoroborate

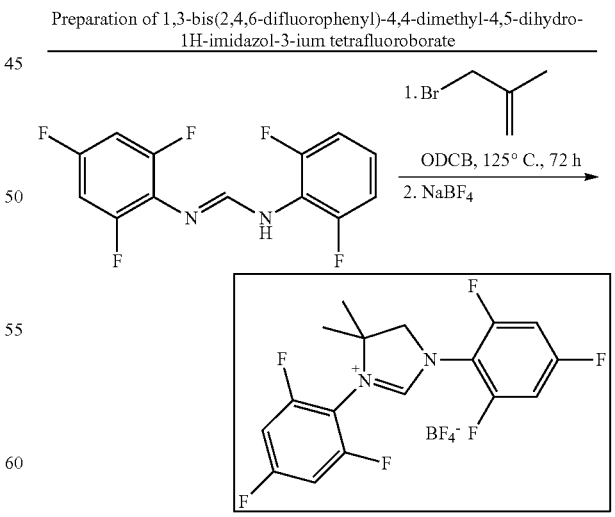

To a 40 mL scintillation vial equipped with a magnetic stir bar was added N,N'-bis(2,4,6-trifluorophenyl)formimidamide (0.511 g, 1.68 mmol), 3-bromo-2-methylpropene (0.200 mL, 1.97 mmol), and ortho-dichlorobenzene (4 mL).

The reaction was heated to 120° C. for 60 h. After cooling to 0° C. the resulting precipitate was isolated by filtration and washed with hexanes (3×15 mL). The crude product was then partitioned between dichloromethane and an aqueous sodium tetrafluoroborate solution (30 mL, 1:1, 0.75 g NaBF$_4$/15 mL). The organic layer was separated and all volatiles were removed by rotary evaporation affording 1,3-bis(2,6-difluorophenyl)-4,4-dimethyl-4,5-dihydro-1H-imidazol-3-ium tetrafluoroborate (0.339 g, 45.2% yield).

$^1$H NMR (400 MHz, DMSO-d$_6$) δ 9.49 (s, 1H), 7.71-7.59 (m, 4H), 4.48 (s, 2H), 1.52 (s, 6H).

Example 15

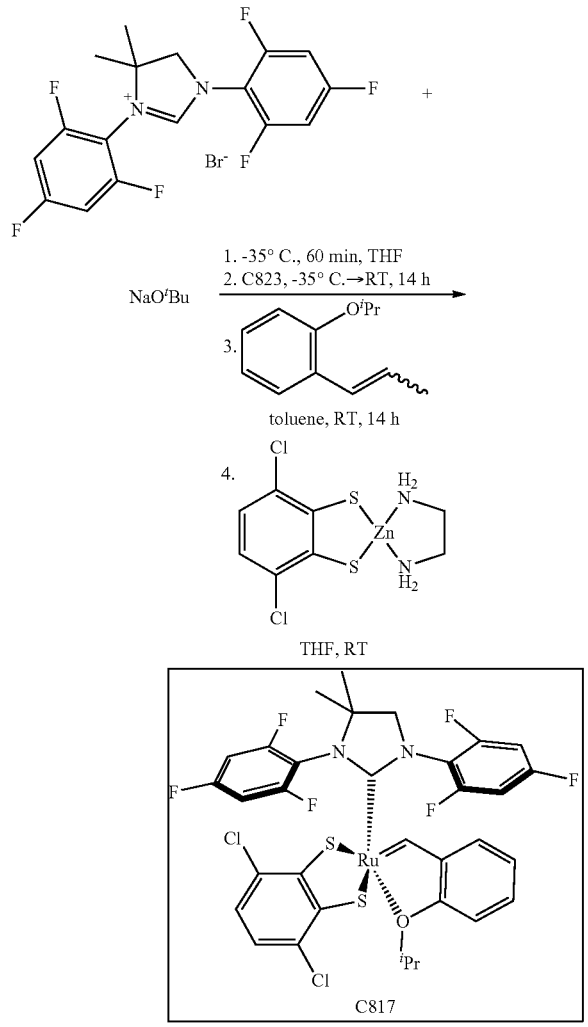

Preparation of C817

In an argon filled glovebox, 1,3-bis(2,4,6-difluorophenyl)-4,4-dimethyl-4,5-dihydro-1H-imidazol-3-ium bromide (0.300 g, 0.683 mmol), sodium tert-butoxide (0.0656 g, 0.683 mmol), and C823 (0.281 g, 0.342 mmol) were weighed into separate 40 mL scintillation vials equipped with magnetic stir bars and each dissolved/suspended in tetrahydrofuran (10 mL). The solutions/suspensions were cooled to −35° C. then the solution of sodium tert-butoxide was added to the solution of 1,3-bis(2,4,6-difluorophenyl)-4,4-dimethyl-4,5-dihydro-1H-imidazol-3-ium bromide over 2 minutes. The reaction was stirred at −35° C. for 30 minutes then combined with the chilled suspension of C823 and stirred for an additional 30 minutes at −35° C. before allowing the reaction to slowly warm to ambient temperature overnight. The reaction was subsequently devolatilized, triturated with hexanes (2×40 mL), dissolved in toluene (10 mL), and filtered through celite. The crude solution was combined with a solution of 1-isopropoxy-2-(prop-1-en-1-yl)benzene (0.301 g, 1.71 mmol) in toluene (2 mL) and stirred overnight at ambient temperature. The resulting solution was diluted with hexanes (15 mL) to afford a green precipitate which was isolated by filtration and washed with toluene/hexanes (1:10, 2×10 mL). The precipitate was dissolved in tetrahydrofuran (5 mL) and combined with (3,6-dichlorobenzene-1,2-dithiolato)(ethylenediamine)zinc(II) (0.086 g, 0.26 mmol) in a 20 mL scintillation vial equipped with a magnetic stir bar. The resulting reaction was stirred at ambient temperature for 60 minutes then devolatilized, dissolved in dichloromethane, filtered, and recrystallized from dichloromethane/diethyl ether at −35° C. The resulting yellow/brown crystals were washed with cold diethyl ether (2×3 mL) then dried under vacuum to afford C817 (0.0462 g, 16.5% yield overall).

$^1$H NMR (400 MHz, CD$_2$Cl$_2$) [two conformers in solution, 40:60] δ 14.54 br s (0.4H), 14.44 (br s, 0.6H), 7.43-7.34 (m, 1H), 7.11 (d, J=8.6 Hz, 1H), 6.97-6.89 (m, 2H), 6.88-6.81 (m, 2H), 6.77-6.67 (m, 1H), 6.40-6.64 (m, 2H), 5.95-5.82 (m, 1H), 5.52-5.35 (m, 1H), 3.90 (br s, 1.2H), 3.75 (br s, 0.8H), 1.88-1.74 (m, 6H), 1.45-1.29 (m, 6H).

Stereoretentive Self-Metathesis of Internal Olefins

Example 16

Self-Metathesis of cis or trans-5-Tetradecene (5C14)

In an argon filled glovebox, a 20 mL scintillation vial equipped with a magnetic stir bar was charged with C765 (4.5 mg, 0.0059 mmol) and tetrahydrofuran (1 mL). 5-Tetradecene (cis or trans) (0.150 mL, 0.588 mmol) was subsequently added, the vial sealed and heated to 40° C. for 2 hours. Yields and stereoselectivies were determined by gas chromatography (method 1).

TABLE 1

$$5C14 \xrightarrow[\text{THF [0.5 M], 2 h, 40° C.}]{\text{1.0 mol \% C765}} 5C10 + \% 9C18$$

| 5C14 (cis:trans) | % 5C14 (Z/E) | % 5C10 (Z/E) | % 9C18 |
|---|---|---|---|
| cis > 98% | 50 (97/3) | 25 (97/3) | 25 |
| trans > 98% | 54 (4/96) | 23 (5/95) | 23 |

Unexpectedly, after 2 hours at 40° C., reactions of either cis or trans-5C14 (>98% stereoisomerically pure) catalyzed by 1 mol % C765 reached a near equilibrium distribution of products while retaining the stereochemistry of the starting material in high fidelity.

Example 17

Self-Metathesis of Various Ratios of cis and trans-5-Tetradecene (5C14)

In an argon filled glovebox, a 20 mL scintillation vial equipped with a magnetic stir bar was charged with C765

(4.5 mg, 0.0059 mmol) and tetrahydrofuran (1 mL). 5-Tetradecene (cis/trans) (0.150 mL total, 0.588 mmol) in an appropriate ratio was subsequently added, the vial sealed and stirred at ambient temperature. Reactions were sampled at 2 and 4 hour time points and yields/stereoselectives were determined by gas chromatography (method 1).

TABLE 2

$$5C14 \xrightleftharpoons[\text{THF [0.5 M], RT}]{0.5 \text{ mol \% C765}} 5C10 + 9C18$$

| entry | 5C14 (cis:trans) | time (h) | % 5C14 (Z/E) | % 5C10 (Z/E) | % 9C18 |
|---|---|---|---|---|---|
| 1 | cis > 98% | 2 | 54 (95/5) | 23 (95/5) | 23 |
|   |           | 4 | 52 (94/6) | 24 (94/6) | 24 |
| 2 | 90:10     | 2 | 54 (74/26) | 23 (90/10) | 23 |
|   |           | 4 | 53 (72/28) | 23 (87/13) | 24 |
| 3 | 50:50     | 2 | 64 (36/64) | 18 (73/27) | 18 |
|   |           | 4 | 63 (36/64) | 19 (68/32) | 18 |
| 4 | 10:90     | 2 | 86 (9/91) | 7 (49/51) | 7 |
|   |           | 4 | 84 (8/92) | 8 (47/53) | 8 |
| 5 | trans > 98% | 2 | 82 (2/98) | 9 (11/89) | 9 |
|   |           | 4 | 80 (2/98) | 10 (10/90) | 10 |

Table 2 summarizes a series of reactions where C765 (0.5 mol %) was exposed to various ratios of cis and trans-5C14. While good stereoretention is attainable when isomerically pure starting material is used (entries 1 and 5), product distributions from reactions with mixtures of cis and trans-5C14 were complicated by the difference in reactivity of cis and trans stereoisomers.

Example 18

Self-Metathesis of cis-5-Tetradecene (5C14)

In an argon filled glovebox, a 20 mL scintillation vial equipped with a magnetic stir bar was charged with C849z (10-5000 ppm) and tetrahydrofuran (1 mL). cis-5-Tetradecene (0.150 mL, 0.588 mmol) was subsequently added, the vials sealed and stirred at ambient temperature. Reactions were sampled at appropriate time intervals and yields/stereoselectivies were determined by gas chromatography (method 1).

TABLE 3

$$5C14 \xrightleftharpoons[\text{THF [0.5 M], RT}]{x \text{ ppm C849z}} 5C10 + 9C18$$

| entry | C849z (ppm) | time (min) | % 5C14 (Z/E) | % 5C10 (Z/E) | % 9C18 | % isomers |
|---|---|---|---|---|---|---|
| 1 | 5000 | 30 | 47 (92/8) | 23 (91/9) | 24 | 6 |
|   |      | 60 | 42 (90/10) | 21 (88/12) | 22 | 15 |
|   |      | 120 | 36 (81/19) | 18 (81/19) | 18 | 28 |
| 2 | 1000 | 30 | 50 (95/5) | 25 (95/5) | 24 | 1 |
|   |      | 60 | 49 (94/6) | 25 (94/6) | 24 | 2 |
| 3 | 500  | 30 | 49 (95/5) | 25 (96/4) | 25 | 1 |
|   |      | 60 | 50 (95/5) | 25 (95/5) | 24 | 1 |
| 4 | 100  | 30 | 52 (96/4) | 24 (96/4) | 24 | <1 |
|   |      | 60 | 52 (96/4) | 24 (96/4) | 24 | <1 |
| 5 | 50   | 30 | 51 (95/5) | 25 (96/4) | 24 | <1 |
|   |      | 60 | 51 (94/6) | 25 (96/4) | 24 | <1 |

We increased the steric bulk of the NHC ligand and prepared C849z. Reactions of C849z with cis-5C14 were initially hindered by high catalyst activity (entry 1), as a loading of 5000 ppm (0.5 mol %) afforded a significant amount of isomers and eroded the stereoselectivity of the transformation rapidly. Reducing the catalytic charge (1000 to 50 ppm; entries 2-5) afforded equilibrium distributions within 1 hour with good stereoretention.

Example 19

Self-Metathesis of Various Ratios of cis and trans-5-Tetradecene (5C14)

In an argon filled glovebox, a 20 mL scintillation vial equipped with a magnetic stir bar was charged with C849z (500 ppm) and tetrahydrofuran (1 mL). 5-Tetradecene (cis/trans) (0.150 mL total, 0.588 mmol) in an appropriate ratio was subsequently added, the vial sealed and stirred at ambient temperature. Reactions were sampled at appropriate time intervals and yields/stereoselectivies were determined by gas chromatography (method 1).

TABLE 4

$$5C14 \xrightleftharpoons[\text{RT}]{500 \text{ ppm C849z}} 5C10 + 9C18$$

| entry | 5C14 (cis:trans) | time (min) | % 5C14 (Z/E) | % 5C10 (Z/E) | % 9C18 |
|---|---|---|---|---|---|
| 1 | cis > 98% | 30 | 63 (95/5) | 19 (95/5) | 18 |
|   |           | 60 | 56 (94/6) | 22 (95/5) | 22 |
|   |           | 120 | 54 (93/7) | 23 (95/5) | 23 |
|   |           | 240 | 54 (93/7) | 24 (95/5) | 23 |
| 2 | 90:10     | 30 | 60 (77/23) | 20 (96/4) | 20 |
|   |           | 60 | 57 (76/24) | 21 (96/4) | 21 |
|   |           | 120 | 57 (75/25) | 22 (96/4) | 21 |
|   |           | 240 | 57 (75/25) | 22 (96/4) | 21 |
| 3 | 50:50     | 30 | 74 (33/67) | 13 (92/8) | 13 |
|   |           | 60 | 73 (33/67) | 14 (90/10) | 13 |
|   |           | 120 | 73 (33/67) | 14 (88/12) | 14 |
|   |           | 240 | 73 (33/67) | 14 (88/12) | 14 |
| 4 | 10:90     | 30 | 91 (7/93) | 4 (80/20) | 4 |
|   |           | 60 | 91 (8/92) | 5 (74/26) | 5 |
|   |           | 120 | 91 (8/92) | 5 (72/28) | 5 |
|   |           | 240 | 91 (8/92) | 5 (72/28) | 5 |
| 5 | trans > 98% | 30 | 98 (2/98) | 1 (64/36) | <1 |
|   |           | 60 | 97 (2/98) | 1 (61/39) | 1 |
|   |           | 120 | 97 (2/98) | 1 (59/41) | 1 |
|   |           | 240 | 97 (2/98) | 1 (58/42) | 1 |

Using an optimized catalyst loading, Table 4 summarizes a series of reactions where C849z (500 ppm) was exposed to various ratios of cis and trans-5C14. Unlike C765, C849z afforded product distributions that approach theoretical, when the trans-5-tetradecene is considered an unreactive stereoisomer.

Example 20

Self-Metathesis of cis or trans-Methyl-9-octadecenoate (MO)

In an argon filled glovebox, a 20 mL scintillation vial equipped with a magnetic stir bar was charged with either C765 (0.5-7.5 mol %) or C849z (100 ppm) and tetrahydrofuran (1 mL). Methyl-9-octadecenoate (cis or trans) (0.150 mL, 0.442 mmol) was subsequently added, the vial sealed and stirred at ambient temperature. Reactions were sampled at appropriate time intervals and yields/stereoselectivies were determined by gas chromatography (method 2). DE is 1,18-dimethyl ester of 9-octadecene and 9C18 is 9-octadecene.

TABLE 5

| entry | Ru (mol %) | MO (cis:trans) | time (h) | % MO (Z/E) | % DE (Z/E) | % 9C18 (Z/E) |
|---|---|---|---|---|---|---|
| 1 | C849z (0.01) | cis > 99% | 0.5 | 64 (>99/1) | 18 (>99/1) | 18 (>99/1) |
|   |   |   | 1.5 | 53 (>99/1) | 23 (>99/1) | 24 (>99/1) |
|   |   |   | 2 | 52 (>99/1) | 24 (>99/1) | 24 (>99/1) |
| 2 | C849z (0.01) | trans > 97% | 0.5 | 100 (<1/99) | ND[a] | ND[a] |
|   |   |   | 1.5 | 100 (<1/99) | ND[a] | ND[a] |
|   |   |   | 2 | 100 (<1/99) | ND[a] | ND[a] |
| 3 | C765 (0.5) | cis > 99% | 0.5 | 90 (>99/1) | 5 (>99/1) | 5 (>99/1) |
|   |   |   | 1.5 | 84 (>99/1) | 8 (>99/1) | 8 (>99/1) |
|   |   |   | 2 | 80 (>99/1) | 10 (>99/1) | 10 (>99/1) |
| 4 | C765 (0.5) | trans > 97% | 2 | 100 (<1/99) | ND[a] | ND[a] |
| 5 | C765 (2.5) | trans > 97% | 4 | 98 (<1/99) | 1 (<1/99) | 1 (<1/99) |
|   |   |   | 20 | 92 (<1/99) | 4 (<1/99) | 4 (<1/99) |
| 6 | C765 (5.0) | trans > 97% | 4 | 93 (<1/99) | 3 (<1/99) | 3 (<1/99) |
|   |   |   | 20 | 72 (1/99) | 14 (3/97) | 14 (3/97) |
| 7 | C765 (7.5) | trans > 97% | 4 | 80 (<1/99) | 10 (<1/99) | 10 (<1/99) |
|   |   |   | 20 | 52 (4/96) | 24 (4/96) | 24 (4/96) |

[a] not detected

The self-metathesis of methyl-9-octadecenoate (MO) was subsequently examined to determine the effect of modest functionality on the transformation (Table 5). Exposing cis-methyl-9-octadecenoate to C849z (0.1 mol %) afforded an equilibrium distribution of product within 2 hours with excellent stereoretention (>99% Z) (entry 1). At this same loading, no reaction was observed with trans-methyl-9-octadecenoate (entry 2). A higher catalyst loading of C765 (0.5 mol %) afforded 20% conversion of cis-methyl-9-octadecenoate while failing to afford any reaction with trans-methyl-9-octadecenoate after 2 hours (entries 3 and 4). Increasing the catalyst loading of C765 restored reactivity with trans-methyl-9-octadecenoate (entries 5-7) and after 20 hours, C765 (7.5 mol %) afforded a near equilibrium distribution of products with good stereoretention (96% E).

Example 21

Self-Metathesis of Various Ratios of cis and trans-Methyl-9-octadecenoate (MO)

In an argon filled glovebox, a 20 mL scintillation vial equipped with a magnetic stir bar was charged with C849z (1000 ppm) and tetrahydrofuran (1 mL). Methyl-9-octadecenoate (cis/trans) (0.150 mL total, 0.442 mmol) was subsequently added, the vial sealed and stirred at ambient temperature. Reactions were sampled at appropriate time intervals and yields/stereoselectivies were determined by gas chromatography (method 2).

TABLE 6

| entry | MO (cis:trans) | time (min) | % MO (Z/E) | % DE | % 9C18 (Z/E) |
|---|---|---|---|---|---|
| 1 | cis > 99% | 30 | 50 (>99/1) | 25 | 25 (>99/1) |
|   |   | 60 | 50 (>99/1) | 25 | 25 (>99/1) |
|   |   | 120 | 50 (>99/1) | 25 | 25 (>99/1) |
|   |   | 240 | 50 (>99/1) | 25 | 25 (98/2) |
| 2 | 80:20 | 30 | 80 (75/25) | 10 | 10 (>99/1) |
|   |   | 60 | 72 (72/27) | 14 | 14 (97/3) |

TABLE 6-continued

| entry | MO (cis:trans) | time (min) | % MO (Z/E) | % DE | % 9C18 (Z/E) |
|---|---|---|---|---|---|
|   |   | 120 | 68 (70/30) | 16 | 16 (97/3) |
|   |   | 240 | 66 (68/32) | 17 | 17 (96/4) |
| 3 | 50:50 | 30 | 91 (46/54) | 5 | 5 (>99/1) |
|   |   | 60 | 88 (44/56) | 6 | 6 (>99/1) |
|   |   | 120 | 86 (42/58) | 7 | 7 (>99/1) |
|   |   | 240 | 85 (42/58) | 7 | 7 (>99/1) |
| 4 | 20:80 | 30 | 100 (20/80) | ND$^a$ | ND$^a$ |
|   |   | 60 | 99 (20/80) | <1 | <1 (>99/1) |
|   |   | 120 | 99 (20/80) | 1 | 1 (>99/1) |
|   |   | 240 | 99 (20/80) | 1 | 1 (>99/1) |
| 5 | trans > 97% | 30 | 100 (<1/99) | ND$^a$ | ND$^a$ |
|   |   | 60 | 100 (<1/99) | ND$^a$ | ND$^a$ |
|   |   | 120 | 100 (<1/99) | ND$^a$ | ND$^a$ |
|   |   | 240 | 100 (<1/99) | ND$^a$ | ND$^a$ |

$^a$not detected

Table 6 summarizes a series of reactions where C849z (1000 ppm) was exposed to various ratios of cis and trans-methyl-9-octadecenoate. Reactions with 80 or 100% cis-methyl-9-octadecenoate (entries 1 and 2) afforded near theoretical product distributions after 4 hours with excellent stereoretention. Reactions conducted with an increased trans-methyl-9-octadecenoate content (entries 3-5) afforded very little reactivity although products maintained high fidelity.

Example 22

Self-Metathesis of Cis or Trans-2-Hexene

In an argon filled glovebox, a 40 mL scintillation vial equipped with a magnetic stir bar was charged with catalyst and tetrahydrofuran (1 mL). 2-Hexene (cis or trans) (0.100 mL, 0.815 mmol) was subsequently added, the vial sealed and stirred at ambient temperature. Reactions were sampled at appropriate time intervals and yields/stereoselectivies were determined by gas chromatography (method 1).

TABLE 7

| entry | Ru (mol %) | cis/trans | time (h) | % conv | % yield | Z/E |
|---|---|---|---|---|---|---|
| 1 | C849z (0.05) | cis | 1 | 48 | 44 | 98/2 |
|   |   |   | 2 | 49 | 44 | 97/3 |
|   |   |   | 6 | 50 | 44 | 96/4 |
| 2 |   | trans | 1 | NR$^a$ | NR$^a$ | ND$^b$ |
|   |   |   | 2 | NR$^a$ | NR$^a$ | ND$^b$ |
|   |   |   | 6 | NR$^a$ | NR$^a$ | ND$^b$ |
| 3 | C765 (0.5) | cis | 1 | 48 | 44 | 98/2 |
|   |   |   | 2 | 49 | 44 | 97/3 |
|   |   |   | 6 | 51 | 44 | 92/8 |
| 4 |   | trans | 1 | <1 | <1 | ND$^b$ |
|   |   |   | 2 | 2 | 2 | 36/64 |
|   |   |   | 6 | 4 | 4 | 25/75 |
| 5 | C745 (0.5) | cis | 1 | 46 | 44 | 99/1 |
|   |   |   | 2 | 48 | 44 | 97/3 |
|   |   |   | 6 | 50 | 45 | 94/6 |
| 6 |   | trans | 1 | 1 | 1 | <1/99 |
|   |   |   | 2 | 4 | 4 | <1/99 |
|   |   |   | 6 | 23 | 23 | <1/99 |

$^a$no reaction observed
$^b$not determined

While C849z, in comparison with C765, afforded a greater disparity in the reactivity of cis and trans substrates, we sought to identify a catalyst with an improved rate of reactivity with trans substrates. Reducing the steric bulk of the ortho-substituents of the NHC ligand afforded C745. C849z, C765 and C745 were subsequently screened as catalysts for the self-metathesis of 2-hexene (Table 7). Reactions of cis-2-hexene (entries 1, 3, and 5) reached maximum conversion/yield within 1 hour with excellent stereoretention (>98% Z). Under the same conditions, trans-2-hexene afforded little to no conversion (<4%) after 6 hours when exposed to C765 (0.5 mol %) or C849z (0.05 mol %) (entries 2 and 4). Gratifyingly, C745 (0.5 mol %) afforded 23% yield after 6 hours with excellent stereoretention (>99% E) (entry 6).

Stereoretentive Cross Metathesis of Internal Olefins

Example 23

Cross Metathesis of 4-Octene (4C8) with 1,4-Diacetoxy-2-butene (1,4-DAB)

In an argon filled glovebox, a 20 mL scintillation vial equipped with a magnetic stir bar was charged with catalyst and tetrahydrofuran (0.50 mL). 4-Octene (0.100 mL, 0.64 mmol) and 1,4-diacetoxy-2-butene (0.406 mL, 2.55 mmol) were subsequently added, the vial sealed and stirred at ambient temperature. Reactions were sampled at appropriate time intervals and yields/stereoselectivies were determined by gas chromatography (method 2).

TABLE 8

| entry | C765 (mol %) | 4C8/1,4-DAB | time (h) | % conv | % yield[a] | Z/E[a] |
|---|---|---|---|---|---|---|
| 1 | 3.0 | cis/cis | 0.25 | 54 | 49 | >99/1 |
|   |     |         | 1.5  | 94 | 91 | >99/1 |
|   |     |         | 2.5  | 95 | 91 | >99/1 |
|   |     |         | 5    | 95 | 91 | >99/1 |
| 2 | 5.0 | trans/trans | 1 | 9 | 6 | <1/99 |
|   |     |         | 2    | 15 | 11 | <1/99 |
|   |     |         | 4    | 19 | 17 | <1/99 |
|   |     |         | 5    | 22 | 20 | <1/99 |
|   |     |         | 72   | 33 | 31 | <1/99 |
| 3 | 7.5 | trans/trans | 1 | 15 | 11 | <1/99 |
|   |     |         | 2    | 21 | 19 | <1/99 |
|   |     |         | 4    | 30 | 27 | <1/99 |
|   |     |         | 5    | 33 | 31 | <1/99 |
|   |     |         | 72   | 50 | 47 | <1/99 |

[a]2-hexenyl acetate (2C6 OAc)

The cross metathesis of 4-octene and 1,4-diacetoxy-2-butene was examined (Table 8). Contacting a mixture of cis-1,4-diacetoxy-2-butene and cis-4-octene (4:1) with C765 (3.0 mol %) afforded cis-2-hexenyl acetate in 91% yield (>99% Z) (entry 1). Reactions between trans-1,4-diacetoxy-2-butene and trans-4-octene were considerably slower (entries 2 and 3) but after 3 days, a mixture of trans-1,4-diacetoxy-2-butene and trans-4-octene (4:1) with C765 (7.5 mol %) afforded trans-2-hexenyl acetate in 47% yield (>99% E).

Example 24

Cross Metathesis of trans-4-Octene with trans-1,4-Diacetoxy-2-butene

In an argon filled glovebox, a 4 mL scintillation vial equipped with a magnetic stir bar was charged with catalyst and tetrahydrofuran (1 mL). Trans-4-octene (0.050 mL, 0.32 mmol) and trans-1,4-diacetoxy-2-butene (0.203 mL, 1.27 mmol) were subsequently added, the vial was sealed and stirred at ambient temperature. Reactions were sampled at appropriate time intervals and yields/stereoselectivies were determined by gas chromatography (method 2).

TABLE 9

| entry | Ru | time (h) | % yield[a] | Z/E[a] |
|---|---|---|---|---|
| 1 | C765 | 1 | 0 | ND[b] |
|   |      | 2 | 2 | <1/99 |
|   |      | 4 | 4 | <1/99 |
|   |      | 72 | 13 | <1/99 |
| 2 | C745 | 1 | 2 | <1/99 |
|   |      | 2 | 5 | <1/99 |
|   |      | 4 | 11 | <1/99 |
|   |      | 72 | 24 | <1/99 |
| 3 | C781 | 1 | 4 | <1/99 |
|   |      | 2 | 7 | <1/99 |
|   |      | 4 | 14 | <1/99 |
|   |      | 72 | 28 | <1/99 |
| 4 | C817 | 1 | 3 | <1/99 |
|   |      | 2 | 6 | <1/99 |
|   |      | 4 | 11 | <1/99 |
|   |      | 72 | 27 | <1/99 |
| 5 | C905 | 1 | 2 | <1/99 |
|   |      | 2 | 2 | <1/99 |
|   |      | 4 | 4 | <1/99 |
|   |      | 48 | 4 | <1/99 |

[a]2C6 OAc
[b]not determined

Focusing our efforts on identifying catalysts with improved reactivity toward trans substrates, C781, C817 and C905 were prepared. Contacting a mixture of trans-1,4-diacetoxy-2-butene and trans-4-octene (4:1) with ruthenium catalyst (3.0 mol %) afforded trans-2-hexenyl acetate (Table 9). After 3 days, C765 afforded 13% yield of trans-2-hexenyl acetate (entry 1) whereas C745, C781 and C817 afforded 24-28% yield (entries 2-4). C905 performed poorly affording <5% yield (entry 5).

Stereoretentive Cross Metathesis of Terminal Olefins with Internal Olefins

Example 25

Cross Metathesis of Allyl Acetate with Cis or Trans-4-Octene

In an argon filled glovebox, a 20 mL scintillation vial equipped with a magnetic stir bar was charged with catalyst and tetrahydrofuran (1 mL). 4-Octene (cis or trans) (0.120 mL, 0.75 mmol) and allyl acetate (0.050 mL, 0.38 mmol) were subsequently added, the vial sealed and stirred at 30° C. Reactions were sampled at appropriate time intervals and yields/stereoselectivies were determined by gas chromatography (method 2).

TABLE 10

AcO allyl acetate 2 4C8 → 3 mol % Ru / 30° C., THF → AcO 2C6 OAc

| entry | cis/trans | Ru | time (h) | % conv | % yield$^a$ | Z/E$^a$ |
|---|---|---|---|---|---|---|
| 1 | cis | C765 | 2 | 28 | 28 | >99/1 |
|   |   |   | 4 | 28 | 28 | >99/1 |
|   |   |   | 22 | 28 | 28 | >99/1 |
| 2 | trans | C765 | 2 | ND$^b$ | ND$^b$ | ND$^b$ |
|   |   |   | 4 | ND$^b$ | ND$^b$ | ND$^b$ |
|   |   |   | 22 | ND$^b$ | ND$^b$ | ND$^b$ |
| 3 | cis | C849z | 2 | 22 | 22 | >99/1 |
|   |   |   | 4 | 22 | 22 | >99/1 |
|   |   |   | 22 | 22 | 22 | >99/1 |
| 4 | trans | C849z | 2 | ND$^b$ | ND$^b$ | ND$^b$ |
|   |   |   | 4 | ND$^b$ | ND$^b$ | ND$^b$ |
|   |   |   | 22 | ND$^b$ | ND$^b$ | ND$^b$ |

$^a$2C6 OAc
$^b$not detected

A mixture of allyl acetate and cis or trans-4-octene was combined with C849z or C765 (3 mol %) (Table 10). After 22 hours, reactions of cis-4-octene and C849z or C765 afforded 22 and 28% yield of cis-2-hexenyl acetate (>99% Z), respectively (entries 1 and 3). No reactions were observed with trans-4-octene under these conditions (entries 2 and 4).

Example 26

Cross Metathesis of Allyl Benzene with Cis or Trans-4-Octene

In an argon filled glovebox, a 20 mL scintillation vial equipped with a magnetic stir bar was charged with catalyst and tetrahydrofuran (1 mL). 4-Octene (cis or trans) (0.120 mL, 0.75 mmol) and allyl benzene (0.059 mL, 0.38 mmol) were subsequently added, the vial sealed and stirred at ambient temperature. Reactions were sampled at appropriate time intervals and yields/stereoselectivies were determined by gas chromatography (method 2).

TABLE 11

Ph allyl benzene +

2 4C8 → 3 mol % Ru / THF, RT → Ph 1Ph2C6

| entry | Ru | cis/trans | time (h) | % conv | % yield$^a$ | Z/E$^a$ |
|---|---|---|---|---|---|---|
| 1 | C849z | cis | 2 | 91 | 77 | 99/1 |
|   |   |   | 4 | 92 | 77 | 99/1 |
| 2 |   | trans | 2 | 31 | 2 | <1/99 |
|   |   |   | 4 | 33 | 2 | <1/99 |
| 3 | C765 | cis | 2 | 55 | 45 | 93/7 |
|   |   |   | 4 | 61 | 46 | 88/12 |
| 4 |   | trans | 2 | 23 | 9 | 8/92 |
|   |   |   | 4 | 31 | 9 | 10/90 |
| 5 | C745 | cis | 2 | 81 | 61 | 96/4 |
|   |   |   | 4 | 82 | 62 | 95/5 |
| 6 |   | trans | 2 | 60 | 32 | 3/97 |
|   |   |   | 4 | 64 | 32 | 3/97 |

$^a$1-phenyl-2-hexene 1Ph2C6

A mixture of allyl benzene and cis or trans-4-octene was combined with C849z, C765 or C745 (3 mol %) (Table 11). After 4 hours, reactions with cis-4-octene and C849z, C765 or C745 afforded 77, 46, and 62% yield respectively (entries 1, 3, and 5) with good stereoretention. Conversions were 10-20% higher than the observed yields with the major byproduct resulting from secondary self-metathesis of 1-phenyl-2-hexene to afford 1,4-diphenyl-2-butene. Reactions were conducted in the same fashion with trans-4-octene and C849z, C765 or C745 afforded 2, 9, and 32% yield respectively (entries 2, 4, and 6) with good to excellent stereoretention. Conversions were 20-30% higher than the observed yields with the major byproduct resulting from isomerization of allyl benzene to (3-methylstyrene.

Example 27

Cross Metathesis of 1-Decene (1C10) with Cis or Trans-4-Octene

In an argon filled glovebox, a 20 mL scintillation vial equipped with a magnetic stir bar was charged with catalyst and tetrahydrofuran (1 mL). 4-Octene (cis or trans) (0.083 mL, 0.53 mmol) and 1-decene (0.050 mL, 0.26 mmol) were subsequently added, the vial sealed and stirred at ambient temperature. Reactions were sampled at appropriate time intervals and yields/stereoselectivies were determined by gas chromatography (method 1).

TABLE 12

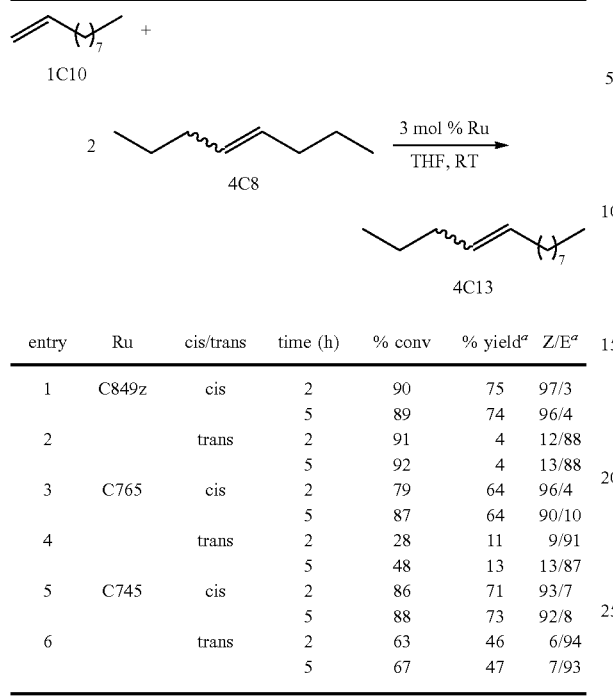

| entry | Ru | cis/trans | time (h) | % conv | % yield[a] | Z/E[a] |
|---|---|---|---|---|---|---|
| 1 | C849z | cis | 2 | 90 | 75 | 97/3 |
|   |   |   | 5 | 89 | 74 | 96/4 |
| 2 |   | trans | 2 | 91 | 4 | 12/88 |
|   |   |   | 5 | 92 | 4 | 13/88 |
| 3 | C765 | cis | 2 | 79 | 64 | 96/4 |
|   |   |   | 5 | 87 | 64 | 90/10 |
| 4 |   | trans | 2 | 28 | 11 | 9/91 |
|   |   |   | 5 | 48 | 13 | 13/87 |
| 5 | C745 | cis | 2 | 86 | 71 | 93/7 |
|   |   |   | 5 | 88 | 73 | 92/8 |
| 6 |   | trans | 2 | 63 | 46 | 6/94 |
|   |   |   | 5 | 67 | 47 | 7/93 |

[a]4C13

A mixture of 1-decene and cis or trans-4-octene was combined with C849z, C765 or C745 (3.0 mol %) in tetrahydrofuran (1.0 mL) (Table 12). After 5 hours, reactions with cis-4-octene and C849z, C765 or C745 afforded 74, 64, and 73% yield of cis-4-tridecene (4C13), respectively, with good stereoretention (entries 1, 3, and 5). Conversions were 15-23% higher than the observed yields with the major byproduct (9-octadecene) resulting from secondary self-metathesis. Exchanging cis-4-octene with trans-4-octene afforded less productive reactions as C849z, C765 or C745 afforded 4, 13, and 47% yield of trans-4-tridecene, respectively, with good stereoretention (entries 2, 4, and 6). Conversions for all transformations were significantly higher than the yields observed (20-88%) and can be attributed to undesired isomerization of 1-decene to 2-decene and 4-octene to 3-octene. The isomerized products also form cis-trans isomers which are proposed to attribute to the 4% product in entry 2. 9-Octadecene is observed which results for the product 4-tetradecene undergoing additional metathesis to yield 9-octadecene and 4-octene.

Example 28

Cross Metathesis of 1-Decene with Cis or Trans-4-Octene

In an argon filled glovebox, a 4 mL scintillation vial equipped with a magnetic stir bar was charged with catalyst and tetrahydrofuran (2 mL). 4-Octene (cis or trans) (0.125 mL, 0.79 mmol) and 1-decene (0.050 mL, 0.26 mmol) were subsequently added, the vial sealed and stirred at ambient temperature. Reactions were sampled at appropriate time intervals and yields/stereoselectivies were determined by gas chromatography (method 1).

TABLE 13

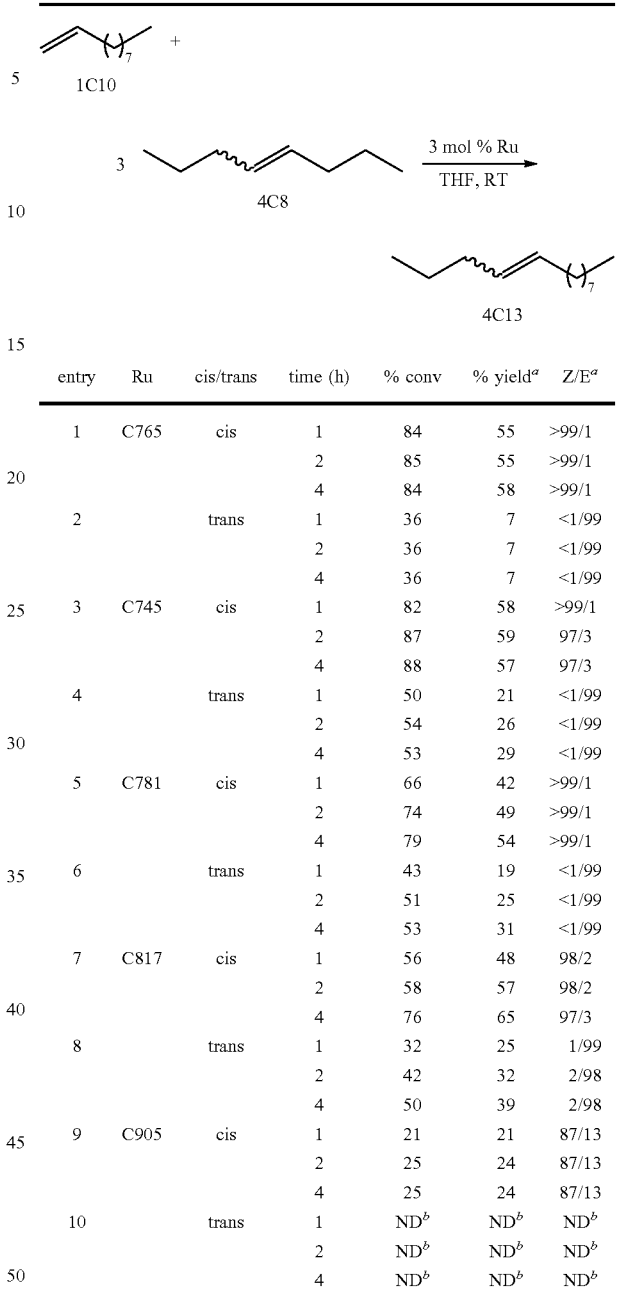

| entry | Ru | cis/trans | time (h) | % conv | % yield[a] | Z/E[a] |
|---|---|---|---|---|---|---|
| 1 | C765 | cis | 1 | 84 | 55 | >99/1 |
|   |   |   | 2 | 85 | 55 | >99/1 |
|   |   |   | 4 | 84 | 58 | >99/1 |
| 2 |   | trans | 1 | 36 | 7 | <1/99 |
|   |   |   | 2 | 36 | 7 | <1/99 |
|   |   |   | 4 | 36 | 7 | <1/99 |
| 3 | C745 | cis | 1 | 82 | 58 | >99/1 |
|   |   |   | 2 | 87 | 59 | 97/3 |
|   |   |   | 4 | 88 | 57 | 97/3 |
| 4 |   | trans | 1 | 50 | 21 | <1/99 |
|   |   |   | 2 | 54 | 26 | <1/99 |
|   |   |   | 4 | 53 | 29 | <1/99 |
| 5 | C781 | cis | 1 | 66 | 42 | >99/1 |
|   |   |   | 2 | 74 | 49 | >99/1 |
|   |   |   | 4 | 79 | 54 | >99/1 |
| 6 |   | trans | 1 | 43 | 19 | <1/99 |
|   |   |   | 2 | 51 | 25 | <1/99 |
|   |   |   | 4 | 53 | 31 | <1/99 |
| 7 | C817 | cis | 1 | 56 | 48 | 98/2 |
|   |   |   | 2 | 58 | 57 | 98/2 |
|   |   |   | 4 | 76 | 65 | 97/3 |
| 8 |   | trans | 1 | 32 | 25 | 1/99 |
|   |   |   | 2 | 42 | 32 | 2/98 |
|   |   |   | 4 | 50 | 39 | 2/98 |
| 9 | C905 | cis | 1 | 21 | 21 | 87/13 |
|   |   |   | 2 | 25 | 24 | 87/13 |
|   |   |   | 4 | 25 | 24 | 87/13 |
| 10 |   | trans | 1 | ND[b] | ND[b] | ND[b] |
|   |   |   | 2 | ND[b] | ND[b] | ND[b] |
|   |   |   | 4 | ND[b] | ND[b] | ND[b] |

[a]4-tridecene 4C13
[b]not detected

A mixture of 1-decene and cis-4-octene was combined with C765, C745, C781, C817, or C905 (3.0 mol %) in tetrahydrofuran (2.0 mL) (Table 13). After 4 hours, C765, C745, C781 and C817 afforded 54-65% yield of cis-4-tridecene with excellent stereoretention (>97% Z) (entries 1, 3, 5, and 7). Exchanging cis-4-octene with trans-4-octene afforded less productive reactions as C765, C745, C781 and C817 afforded 7-39% yield of trans-4-tridecene with excellent stereoretention (>98% E) (entries 2, 3, 6, and 8). C905 performed poorly affording only 24% for the cross metathesis of 1-decene and cis-4-octene and no reaction was observed with trans-4-octene.

Example 29

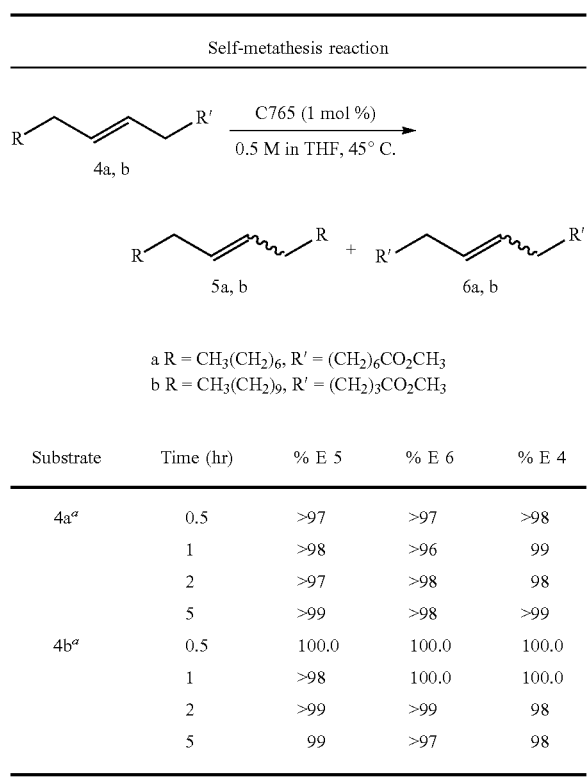

| Substrate | Time (hr) | % E 5 | % E 6 | % E 4 |
|---|---|---|---|---|
| 4a[a] | 0.5 | >97 | >97 | >98 |
|  | 1 | >98 | >96 | 99 |
|  | 2 | >97 | >98 | 98 |
|  | 5 | >99 | >98 | >99 |
| 4b[a] | 0.5 | 100.0 | 100.0 | 100.0 |
|  | 1 | >98 | 100.0 | 100.0 |
|  | 2 | >99 | >99 | 98 |
|  | 5 | 99 | >97 | 98 |

[a]Quantitative data determined by gas chromatography.

Example 30

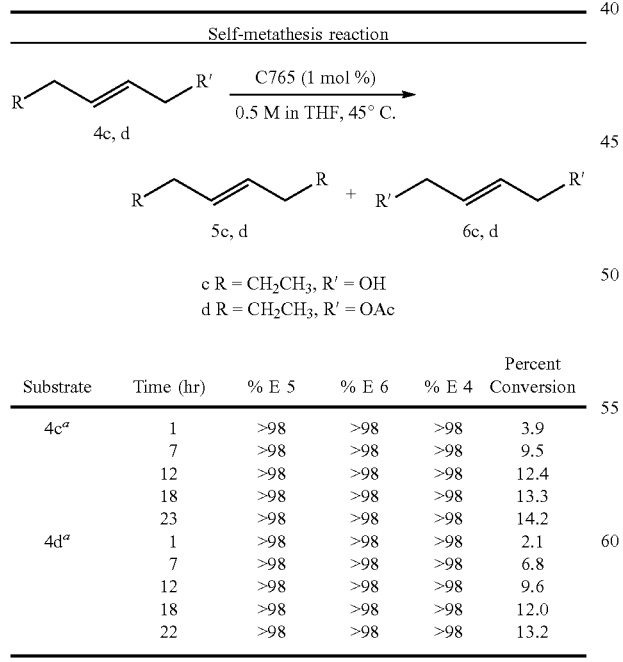

| Substrate | Time (hr) | % E 5 | % E 6 | % E 4 | Percent Conversion |
|---|---|---|---|---|---|
| 4c[a] | 1 | >98 | >98 | >98 | 3.9 |
|  | 7 | >98 | >98 | >98 | 9.5 |
|  | 12 | >98 | >98 | >98 | 12.4 |
|  | 18 | >98 | >98 | >98 | 13.3 |
|  | 23 | >98 | >98 | >98 | 14.2 |
| 4d[a] | 1 | >98 | >98 | >98 | 2.1 |
|  | 7 | >98 | >98 | >98 | 6.8 |
|  | 12 | >98 | >98 | >98 | 9.6 |
|  | 18 | >98 | >98 | >98 | 12.0 |
|  | 22 | >98 | >98 | >98 | 13.2 |

[a]Quantitative data determined by $^1$H NMR.
Reactions were ran in a J. Young tube in THF-$d_8$.

Example 31

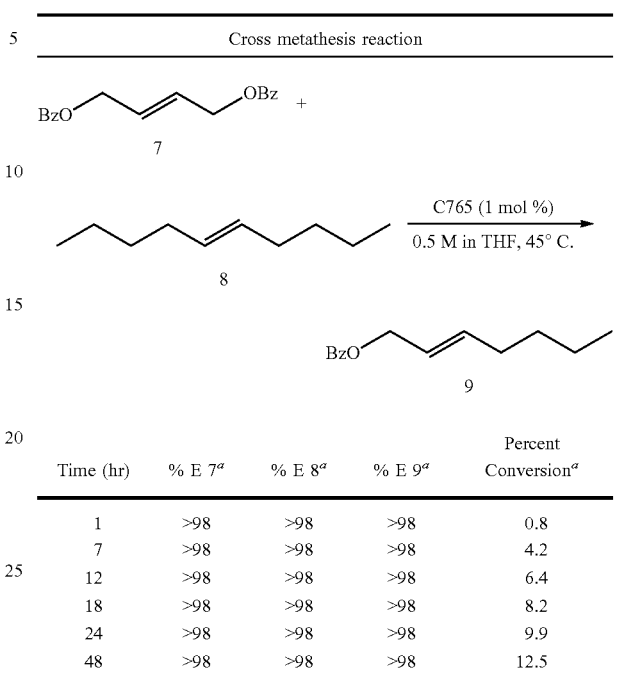

| Time (hr) | % E 7[a] | % E 8[a] | % E 9[a] | Percent Conversion[a] |
|---|---|---|---|---|
| 1 | >98 | >98 | >98 | 0.8 |
| 7 | >98 | >98 | >98 | 4.2 |
| 12 | >98 | >98 | >98 | 6.4 |
| 18 | >98 | >98 | >98 | 8.2 |
| 24 | >98 | >98 | >98 | 9.9 |
| 48 | >98 | >98 | >98 | 12.5 |

[a]Quantitative data determined by $^1$H NMR.
Reactions were ran in a J. Young tube in THF-$d_8$.

What is claimed is:

1. A compound selected from:

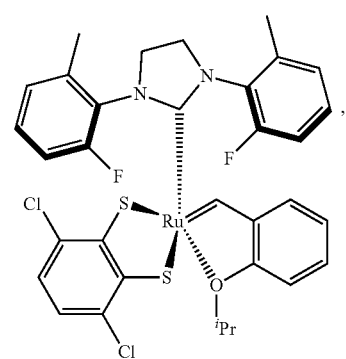

C745

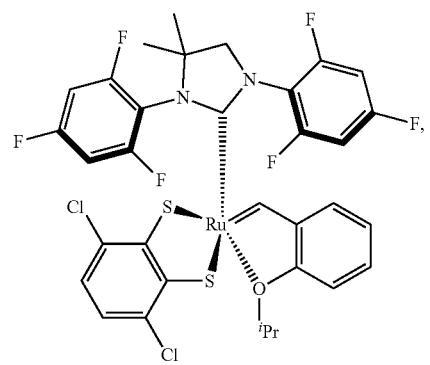

C817

C849z
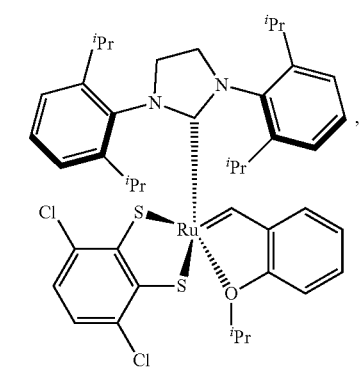
C925
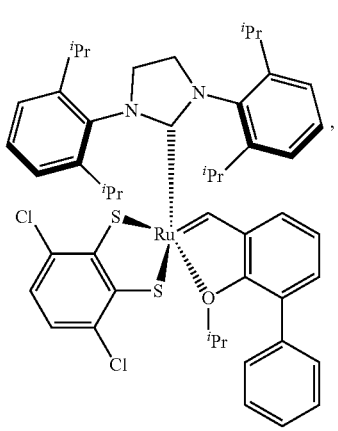
C746
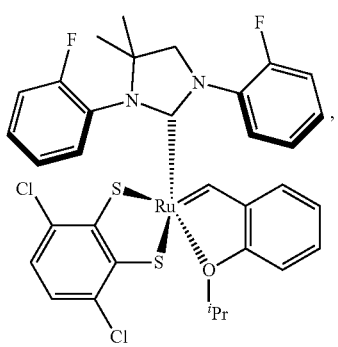
C782
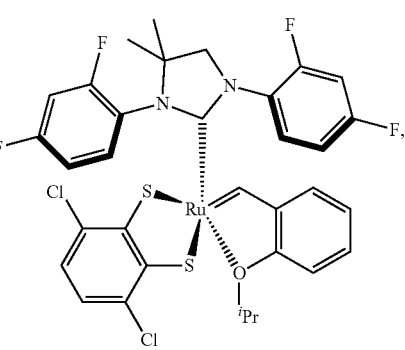
C766
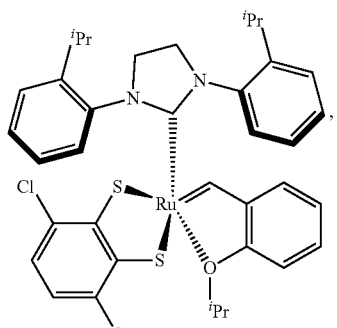
C842
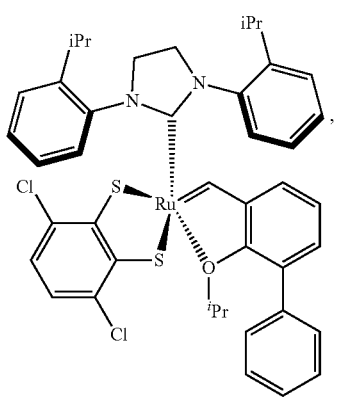
C753
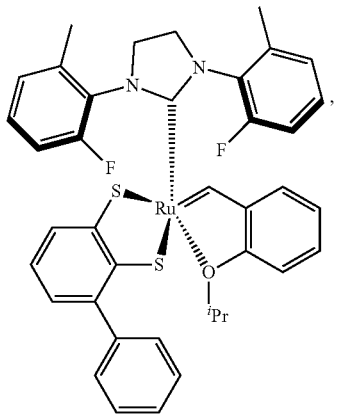
C727
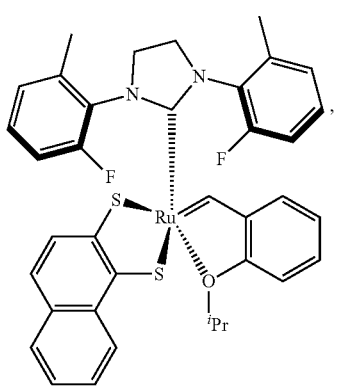

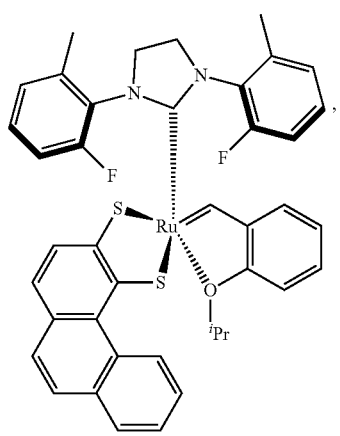
C777
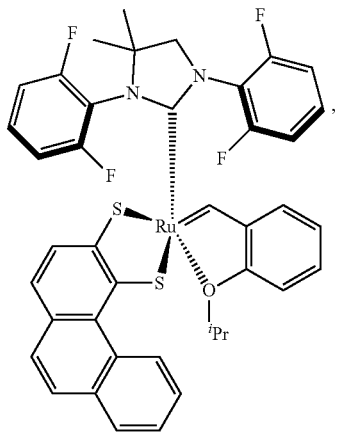
C813
C789
C825
C763
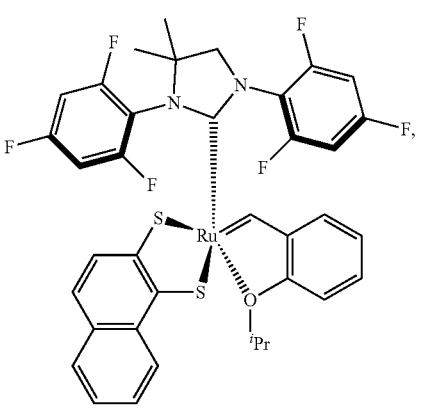
C799

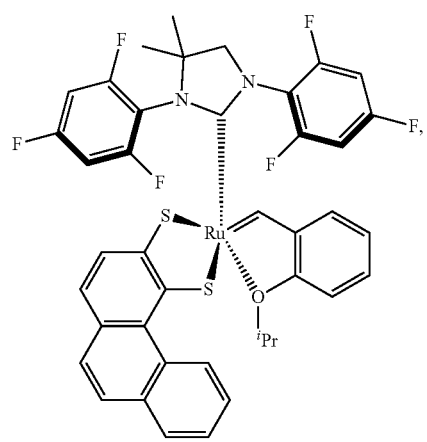
C849f
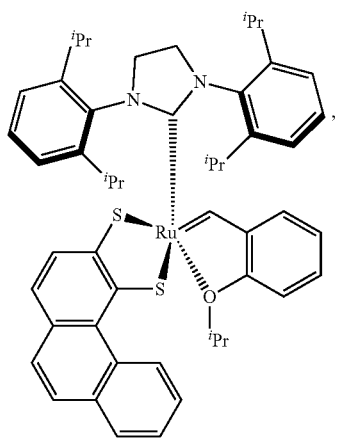
C881
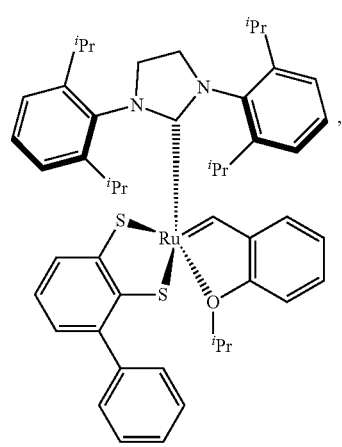
C857
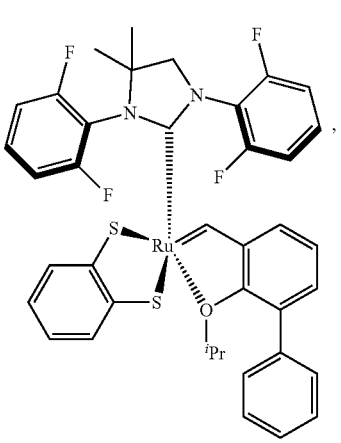
C789a
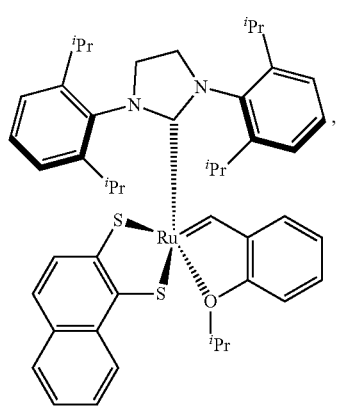
C831c
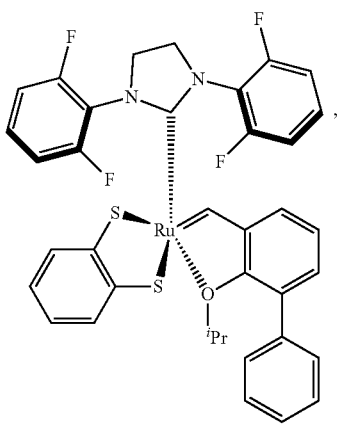
C761

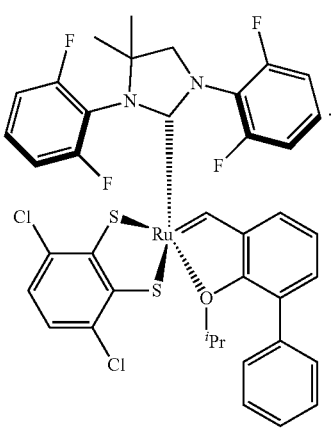

C858

2. The compound as claimed in claim 1, wherein the compound is C745, C817 or C849z.

3. The compound as claimed in claim 1, wherein the compound is C925, C746 or C782.

4. The compound as claimed in claim 1, wherein the compound is C766, C842 or C753.

5. The compound as claimed in claim 1, wherein the compound is C727, C777 or C789.

6. The compound as claimed in claim 1, wherein the compound is C789, C763 or C813.

7. The compound as claimed in claim 1, wherein the compound is C825, C799 or C849f.

8. The compound as claimed in claim 1, wherein the compound is C857, C831c or C881.

9. The compound as claimed in claim 1, wherein the compound is C789a, C761 or C858.

10. The compound as claimed in claim 1, wherein the compound is C849z.

11. A method for performing a cross metathesis reaction, comprising: contacting a first olefin reactant with a second olefin reactant in the presence of a compound according to claim 1, under conditions effective to promote the formation of at least one cross metathesis product.

12. The method according to claim 11, wherein the first olefin reactant and the second olefin reactant are the same.

13. The method according to claim 11 wherein the first olefin reactant and the second olefin reactant are different.

14. The method according to claim 11, wherein the first olefin reactant and the second olefin reactant are each in a Z-configuration.

15. The method according to claim 14, wherein the at least one cross metathesis product is greater than 80% Z.

16. The method according to claim 11, wherein the first olefin reactant and the second olefin reactant are each in an E-configuration.

17. The method according to claim 16, wherein the at least one cross metathesis product is greater than 80% E.

* * * * *